US008288403B2

(12) United States Patent
Baumann et al.

(10) Patent No.: US 8,288,403 B2
(45) Date of Patent: Oct. 16, 2012

(54) HETEROCYCLIC GAMMA SECRETASE MODULATORS

(75) Inventors: Karlheinz Baumann, Efringen-Kirchen (DE); Erwin Goetschi, Reinach BL (CH); Synese Jolidon, Blauen (CH); Anja Limberg, Basel (CH); Thomas Luebbers, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 359 days.

(21) Appl. No.: 12/612,002

(22) Filed: Nov. 4, 2009

(65) Prior Publication Data
US 2010/0120874 A1  May 13, 2010

(30) Foreign Application Priority Data

Nov. 10, 2008  (EP) .................................. 08168719

(51) Int. Cl.
| A61K 31/4025 | (2006.01) |
| A61K 31/4155 | (2006.01) |
| A61K 31/4178 | (2006.01) |
| A61K 31/4192 | (2006.01) |
| A61K 31/4196 | (2006.01) |
| A61K 31/422 | (2006.01) |
| A61K 31/4245 | (2006.01) |
| A61K 31/427 | (2006.01) |
| A61K 31/4439 | (2006.01) |
| A61K 31/506 | (2006.01) |
| C07D 401/02 | (2006.01) |
| C07D 403/02 | (2006.01) |
| C07D 413/02 | (2006.01) |
| C07D 417/02 | (2006.01) |

(52) U.S. Cl. ........ 514/275; 514/340; 514/362; 514/363; 514/364; 514/370; 514/372; 514/377; 514/380; 514/381; 514/382; 514/383; 514/397; 514/407; 544/333; 546/268.4; 548/127; 548/128; 548/133; 548/134; 548/138; 548/198; 548/206; 548/235; 548/247; 548/255; 548/264.8; 548/266.2; 548/311.1; 548/364.1; 548/518

(58) Field of Classification Search ........................ None
See application file for complete search history.

(56) References Cited

U.S. PATENT DOCUMENTS

| 5,686,070 | A | 11/1997 | Doerschuk et al. |
| 6,399,773 | B1 | 6/2002 | Liu et al. |
| 2003/0176454 | A1 | 9/2003 | Yamada et al. |
| 2004/0034008 | A1 | 2/2004 | Stamford et al. |
| 2005/0176772 | A1 | 8/2005 | Calabrese et al. |
| 2006/0004013 | A1 | 1/2006 | Kimura et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0280948 | A1 | 11/2008 | Baumann et al. |
| 2009/0163485 | A1 | 6/2009 | Knust et al. |
| 2009/0181965 | A1 | 7/2009 | Baumann et al. |
| 2009/0215759 | A1 | 8/2009 | Baumann et al. |

FOREIGN PATENT DOCUMENTS

| EP | 0233461 | 8/1987 |
| EP | 1201661 | 5/2002 |
| EP | 1479397 | 11/2004 |
| EP | 1950211 | 7/2008 |
| EP | 2019093 | 1/2009 |
| WO | WO 94/04487 | 3/1994 |
| WO | 97/21704 | 6/1997 |
| WO | 99/65884 | 12/1999 |
| WO | WO 99/65884 | 12/1999 |
| WO | 00/27842 | 5/2000 |
| WO | WO 00/25780 | 5/2000 |
| WO | WO 00/78731 | 12/2000 |
| WO | 01/47897 | 7/2001 |
| WO | 01/87845 | 11/2001 |
| WO | 02/057240 | 7/2002 |
| WO | 03/002561 | 1/2003 |
| WO | WO 03/040141 | 5/2003 |
| WO | 03/047512 | 6/2003 |
| WO | 03/053939 | 7/2003 |
| WO | WO 2004/046118 | 6/2004 |
| WO | 2004/069185 | 8/2004 |
| WO | WO 2004/087699 | 10/2004 |
| WO | WO 2004/110350 | 12/2004 |

(Continued)

OTHER PUBLICATIONS

Dhar, et al. Bioorg. Med. Chem. Lett. 12:3125 (2002).*
Weggen et al., Nature, 414 (2001) pp. 212-216.
Morihara et al., J. Neurochem. 83 (2002) pp. 1009-1012.
Jantzen et al., J. Neuroscience 22 (2002) pp. 226-254.
Takahashi et al., J. Biol. Chem. 278 (2003) pp. 18644-18670.
Beher et al., J. Biol. Chem. 279 (2004) pp. 43419-43426.
Lleo et al., Nature Med. 10 (2004) pp. 1065-1066.
Kukar et al., Nature Med. 11 (2005) pp. 545-550.
Perretto et al., J. Med. Chem. 48 (2005) pp. 5705-5720.
Clarke et al., J. Biol. Chem. 281 (2006) pp. 31279-31289.
Stock et al., Bioorg. Med. Chem. Lett. vol. 16 (2006) pp. 2219-2223.

(Continued)

Primary Examiner — Michael Barker
(74) Attorney, Agent, or Firm — George W. Johnston; Patricia S. Rocha-Tramaloni; Kimberly J. Prior

(57) ABSTRACT

The invention relates to methods for the treatment of Alzheimer's disease, cerebral amyloid angiopathy, hereditary cerebral hemorrhage with amyloidosis, Dutch-type (HCHWA-D), multi-infarct dementia, dementia pugilistica and Down syndrome which comprise administering a therapeutically effective amount of a compound of formula I

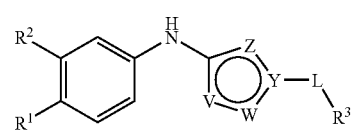

wherein
$R^1$, $R^2$, $R^3$, V, W, Y, and Z are as defined herein or a pharmaceutically active acid addition salt of such compounds. The invention also relates to a subgenus of such compounds and pharmaceutical compositions containing them, as well as methods for their manufacture.

24 Claims, No Drawings

FOREIGN PATENT DOCUMENTS

| | | |
|---|---|---|
| WO | 2005/003103 | 1/2005 |
| WO | WO 2005/013996 | 2/2005 |
| WO | 2005/040120 | 5/2005 |
| WO | WO 2005/044785 | 5/2005 |
| WO | 2005/063022 | 7/2005 |
| WO | WO 2005/115990 | 12/2005 |
| WO | WO 2006/040192 | 4/2006 |
| WO | WO 2006/058905 | 6/2006 |
| WO | 2006/111549 | 10/2006 |
| WO | WO 2006/112550 | 10/2006 |
| WO | WO 2006/112551 | 10/2006 |
| WO | 2007/051333 | 5/2007 |
| WO | 2007/076161 | 5/2007 |
| WO | WO 2007/053452 | 5/2007 |
| WO | WO 2007/054480 | 5/2007 |
| WO | WO 2007/058304 | 5/2007 |
| WO | WO 2007/058305 | 5/2007 |
| WO | WO 2007/060810 | 5/2007 |
| WO | WO 2007/060821 | 5/2007 |
| WO | WO 2007/102580 | 9/2007 |
| WO | WO 2007/120333 | 10/2007 |
| WO | WO 2007/131953 | 11/2007 |
| WO | WO 2007/135969 | 11/2007 |
| WO | WO 2007/135970 | 11/2007 |
| WO | WO 2007/139149 | 12/2007 |
| WO | WO 2008/006103 | 1/2008 |
| WO | WO 2008/013213 | 1/2008 |
| WO | 2008/065626 | 6/2008 |
| WO | WO 2008/097538 | 8/2008 |
| WO | WO 2008/099210 | 8/2008 |
| WO | 2008/107096 | 9/2008 |
| WO | WO 2008/107096 | 9/2008 |
| WO | WO 2008/138753 | 11/2008 |
| WO | WO 2008/156580 | 12/2008 |
| WO | 2009/032277 | 3/2009 |
| WO | WO 2009/032861 | 3/2009 |
| WO | 2009/076337 | 6/2009 |
| WO | 2009/103652 | 8/2009 |
| WO | WO 2008/100412 | 8/2009 |
| WO | 2009/155551 | 12/2009 |
| WO | 2010/010184 | 1/2010 |
| WO | 2010/010188 | 1/2010 |
| WO | 2010/027500 | 3/2010 |
| WO | 2010/098487 | 9/2010 |

OTHER PUBLICATIONS

Narlawar et al., J. Med. Chem. vol. 49 (2006) pp. 7588-7591.
McPhee et al. J. Med. Chem. Soc. vol. 66 pp. 1132-1136 (1944).
Yang et al., J. Org. Chem. vol. 67(21) pp. 7429-7431 (2002).
Dhar et al., Bioorganic & Medicinal Chemistry Letters, (2002) 12(12) pp. 3125-3128 XP002522864.
Paul et al., Jour. of Medicinal Chemistry (1999) 36(19) pp. 2716-2725 XP002522865.
Ringold et al., J. Am. Chem. Soc. 78 (1956) pp. 2477-2479.
Hirt et al., Helv. 33 (1950) pp. 1365-1369.
Grundmann et al., J. Am. Chem. Soc. vol. 79 (1957) pp. 944-948.
Schaeffer et al., J. Am. Chem. Soc. vol. 73 (1951) pp. 2990-2992.
Caubére et al., Bull. Soc. Chim. Fr. (1973) pp. 2112-2115.
Cooke et al., Tetrahedron Vo. 57 (2001) pp. 2787-2789.
Bessard et al., Tetrahedron vol. 55 (1999) pp. 405-412.
Albaneze-Walker et al., Tetrahedron Vo. 61 (2005) pp. 6330-6336.
Menicagli et al., Synth. Commun. vol. 24 (1994) pp. 2153-2158.
Iwanowicz et al., Bioorg. Med. Chem. Lett. vol. 13 (2003) pp. 2059-2063.
Schulte et al., Synlett, pp. 2331-2336 (2007).
Kidwai et al, Chemical Papers pp. 231-234 (2000).
Kumita et al., Nippon Noyaku Gakkaishi vol. 26(1) pp. 60-66 (2001).
Tilley et al, Helv. Chim. Acta, vol. 63, pp. 832-840 (1980).
Wu et al., Tet. Lett. vol. 49, pp. 2869-2871 (2008).
Delecea et al., Proc. Natl. Acad. Sci. USA 95:322-327 (1998).
Sakamoto et al., Regul. Pept. 118:183-191 (2004).
Suzuki et al., Brain Research 1044:116-121 (2005).
(Office Action in copending U.S. Appl. No. 12/114,852 Jun. 28, 2010).
Cai et al., Expert Opin. Ther. Patents 16(5):631-646 (2006).
Piper et al., Eur. J. Neuroscience 12:726-730 (2000).
Winsky Sommerer et al., J. Neuroscience 24:11439-11448 (2004).
Ida et al., Biochem. Biophys. Res. Comm. 270:318-323 (2000).
Sakurai et al., Cell 92:573-585 (1998).
Kuru et al., Neuroreport 11:1977-1980 (2000).
(International Search Report PCT/EP 2008/055290 Oct. 8, 2008).
Siegel, Annu. Rev. Psychol. 55:125-148 (2004).
Pitts et al., Bioorganic & Medicinal Chemistry Letters 12(16):2137-2140 (2002).
Chang et al., Neurosci. Res. 56:356-362 (2006).
Nishino et al., Lancet 355:39-40 (2000).
(International Search Report for PCT/EP2008/067273 May 15, 2009).
Chemelli et al., Cell 98:437-451 (1999).
Malherbe et al., Mol. Pharmacol. 64:823-832 (2003).
Bingham et al., Current Opinion in Drug Discovery & Development 9(5):551-559 (2006).
Lin et al., Cell 98:365-376 (1999).
(International Search Report for PCT/EP2009/062570 Dec. 4, 2009).
Dorwald F. A. Side Reactions in Organic Systhesis "1 & Preface"Wiley,:1-16 (2005).
Peyron et al., Nature Medicine 6:991-997 (2000).
Bourgin et al., J. Neurosci. 20(20):7760-7765 (2000).
(Office Action in copending U.S. Appl. No. 12/334,559 Sep. 30, 2009).
(International Search Report for PCT/EP2009/051613 Apr. 22, 2004).
Kubinyi 3D QSAR in Drug Design: Ligand Protein Interactions & Molecular SimilaritySpringer, vol. 2-3:243-244 (1998).
Mignot et al., Sleep 11:1012-1020 (1997).
Sakurai, Regulatory Peptides 126:3-10 (2005).
(Office Action in copending U.S. Appl. No. 12/334,559 May 20, 2010).
Peyron et al., Neurosci. 18:9996-10015 (1998).
Nambu et al., Brain Res. 18:243-260 (1999).
Smith et al., Neurosci. Lett. 341(3):256-258 (2003).
Digby et al., J. Endocrinol. 191:129-136 (2006).
Patrick, Graham An Introduction to Medicinal Chemistry "10.3.9"Oxford, vol. 3rd edition:210-212, (2005).
(EPO Communication in EP Appl. 09713519.8 Dec. 30, 2011).
Reinke, A. et al., Chem. Biol. Drug Des. 70:206-215 (2007).
Olson, R. et al., Current Topics in Medicinal Chemistry 8:17-33 (2008).
Wilkins et al., Science of Synthesis 13:277-295 (2004).
Nettekoven et al., Synthesis 11:1649-1652 (2003).
Maiti et al., JOC Note 75:1791-1794 (2010).
Nilsson et al., J. Med. Chem. 46:3985-4001 (2003).

* cited by examiner

HETEROCYCLIC GAMMA SECRETASE MODULATORS

PRIORITY TO RELATED APPLICATION(S)

This application claims the benefit of European Patent Application No. 08168719.6, filed Nov. 10, 2008, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed (β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in an increase of shorter Aβ isoforms, such as Aβ38, Aβ37 or others, which have reduced capability for aggregation and plaque formation, and hence less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention relates to methods of treating a disorder selected from the group consisting of Alzheimer's disease, cerebral amyloid angiopathy, hereditary cerebral hemorrhage with amyloidosis, Dutch-type (HCHWA-D), multi-infarct dementia, dementia pugilistica and Down syndrome, which comprises administering a compound of formula I

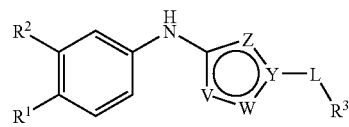

wherein
$R^1$ is a five or six membered heteroaryl group, optionally substituted by one or two R';
R' is lower alkyl;
$R^2$ is hydrogen, lower alkyl, lower alkoxy, hydroxy, halogen or cyano;
Z is N, C, O or S;
V is N, C(R"), O or S;
W is N, C(R"), O, or S;
Y is N or C;
with the proviso that only one of Z, V or W is O or S;
R" is hydrogen, lower alkyl, lower alkyl substituted by halogen or hydroxy, or —C(O)O—$R^4$;
L is a bond, —$(CR^4{}_2)_n$—, —C(O)N$R^4$—, —C(O)N$R^4$CH$_2$—, or —C(O)—;
each $R^4$ is the same or different and is hydrogen or lower alkyl;
$R^3$ is lower alkyl, lower alkoxy, lower alkyl substituted by hydroxy, cycloalkyl, or phenyl optionally substituted by one or more R'";
R'" is halogen, cyano, lower alkyl, lower alkyl substituted by halogen or hydroxy, lower alkoxy or C(O)O—$R^4$; and
n is 1, 2 or 3;
or to pharmaceutically active acid addition salts.

Some compounds of formula I, wherein $R^1$ is an oxazol group, L is a bond and $R^3$ is phenyl, are described in Bioorg. Med. Lett. 12, 2002, 3125-3228, which compounds are IMPDH inhibitors.

Furthermore, known compounds from formula I are further those, wherein the group Het is substituted by amino and the linking group L is —C(O). These compounds are described in WO2005063022 which compounds are useful for plant growth regulation.

WO2002057240 describes compounds for use as kinase inhibitors against tumor growth, in which the linking group L is —C(O)—.

The present compounds of formula I are modulators for amyloid beta and thus, they will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions for compounds of formula I are used: As used herein, the group

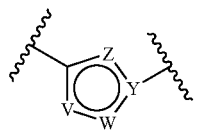

denotes the following 5-membered heteroaryl groups:

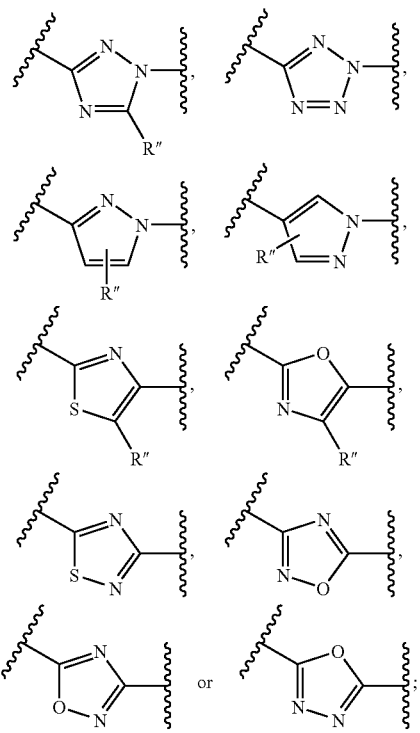

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group containing a lower alkyl residue as defined above and that is attached via an oxygen atom.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CF_2CHF_2$, $CH_2CF_2CF_3$ and the like.

As used herein, the term "lower alkyl substituted by hydroxy" denotes a lower alkyl group as defined above, wherein at least one hydrogen atom is replaced by hydroxy.

The term "halogen" denotes chlorine, iodine, fluorine and bromine.

The term "cycloalkyl" denotes a saturated alkyl ring with 3-7 carbon atoms.

The term "a five or six membered heteroaryl group optionally substituted by one or two R'" defined for $R^1$ is selected from the group consisting of

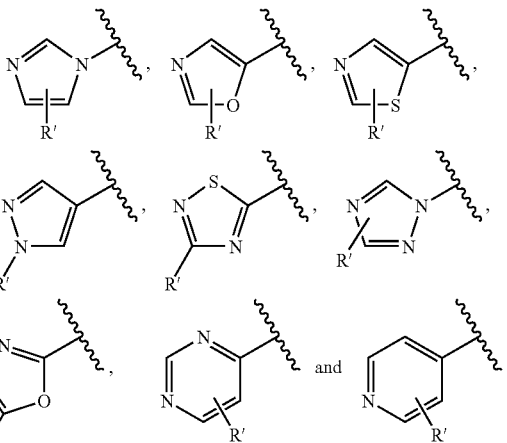

Especially preferred group for $R^1$ is

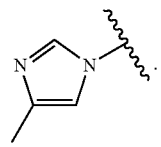

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

A further embodiment of the invention are novel compounds of formula I-A

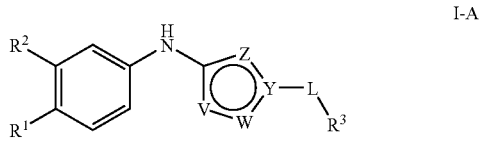

I-A wherein
$R^1$ is a five or six membered heteroaryl group optionally substituted by one or two R' selected from

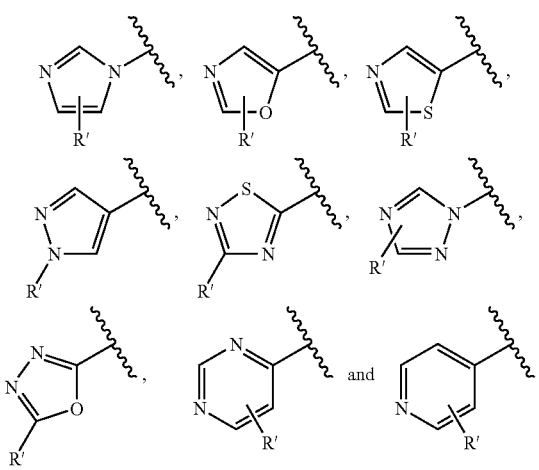

R' is lower alkyl;
R² is hydrogen, lower alkyl, lower alkoxy, hydroxy, halogen or cyano;
Z is N, C, O or S;
V is N, C(R"), O or S;
W is N, C(R"), O, or S;
Y is N or C;
with the proviso that only one of Z, V or W is O or S;
R" is hydrogen, lower alkyl, lower alkyl substituted by halogen or hydroxy, or C(O)O—R⁴;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

The following compounds are encompassed by formula I-A and are therefore an embodiment of the invention:

Compounds of Formula I-A1

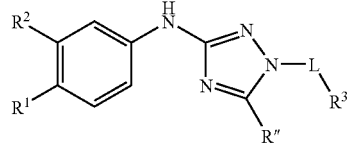

I-A1 wherein
R¹ is

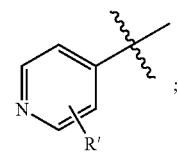

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;

L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

Compounds of Formula I-A11

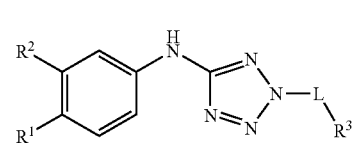

I-A11 wherein
R¹ is

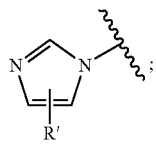

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

Compounds of Formula I-A2

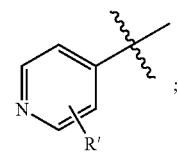

I-A2 wherein
R¹ is

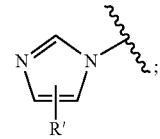

R' is lower alkyl;

R² is hydrogen, lower alkyl, lower alkoxy, hydroxy, halogen or cyano;

L is —(CR⁴₂)ₙ—, —C(O)NR⁴— or —C(O)NR⁴CH₂—;

each R⁴ is the same or different and is hydrogen or lower alkyl;

R³ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R⁴; and n is 1, 2 or 3;

or pharmaceutically active acid addition salts thereof.

Compounds of Formula I-A3

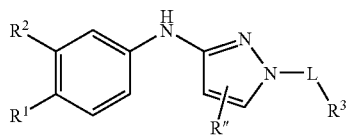

I-A3 wherein
R¹ is a

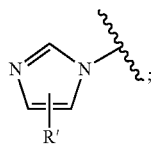

R' is lower alkyl;

R² is hydrogen, lower alkyl, lower alkoxy, hydroxy, halogen or cyano;

R" is hydrogen, lower alkyl, lower alkyl substituted by halogen or hydroxy, or C(O)O—R⁴;

L is —(CR⁴₂)ₙ—, —C(O)NR⁴— or —C(O)NR⁴CH₂—;

each R⁴ is the same or different and is hydrogen or lower alkyl;

R³ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R⁴; and n is 1, 2 or 3;

or pharmaceutically active acid addition salts thereof.

Compounds of Formula I-A4

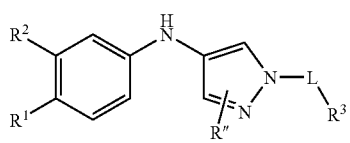

I-A4 wherein
R¹ is

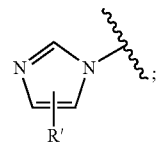

R' is lower alkyl;

R² is hydrogen, lower alkyl, lower alkoxy, hydroxy, halogen or cyano;

R" is hydrogen, lower alkyl, lower alkyl substituted by halogen or hydroxy, or C(O)O—R⁴;

L is —(CR⁴₂)ₙ—, —C(O)NR⁴— or —C(O)NR⁴CH₂—;

each R⁴ is the same or different and is hydrogen or lower alkyl;

R³ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R⁴; and n is 1, 2 or 3;

or pharmaceutically active acid addition salts thereof.

Compounds of Formula I-A5

I-A5 wherein
R¹ is

R' is lower alkyl;

R² is hydrogen, lower alkyl, lower alkoxy, hydroxy, halogen or cyano;

R" is hydrogen, lower alkyl, lower alkyl substituted by halogen or hydroxy, or C(O)O—R⁴;

L is —(CR⁴₂)ₙ—, —C(O)NR⁴— or —C(O)NR⁴CH₂—;

each R⁴ is the same or different and is hydrogen or lower alkyl;

R³ is lower alkyl, cycloalkyl, or phenyl optionally substituted by one or more R'"; R'" is halogen, cyano, lower alkyl, lower alkyl substituted by halogen or hydroxy, lower alkoxy or C(O)O—R⁴; and n is 1, 2 or 3;

or pharmaceutically active acid addition salts thereof.

Compounds of Formula I-A6

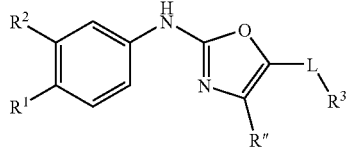

wherein
R¹ is

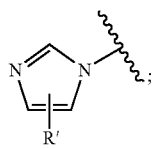

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

Compounds of Formula I-A7

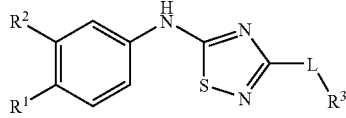

wherein
R¹ is

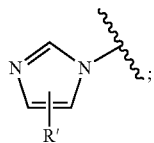

R' is lower alkyl;
R² is hydrogen, lower alkyl, lower alkoxy, hydroxy, halogen or cyano;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

Compounds of Formula I-A8

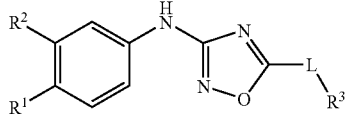

wherein
R¹ is

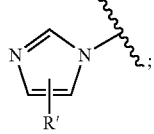

R' is lower alkyl;
R² is hydrogen, lower alkyl, lower alkoxy, hydroxy, halogen or cyano;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or pharmaceutically active acid addition salts thereof.

Compounds of Formula I-A9

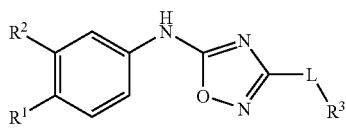

wherein
R¹ is

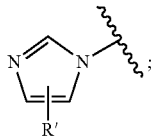

R' is lower alkyl;
R² is hydrogen, lower alkyl, lower alkoxy, hydroxy, halogen or cyano;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, phenyl optionally substituted by one or more R'";

R''' is halogen, cyano, lower alkyl, lower alkyl substituted by halogen or hydroxy, lower alkoxy or C(O)O—R$^4$; and n is 1, 2 or 3;

or pharmaceutically active acid addition salts thereof.

Compounds of Formula I-A10

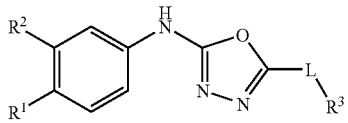
I-A10 wherein
R$^1$ is

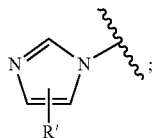

R' is lower alkyl;

R$^2$ is hydrogen, lower alkyl, lower alkoxy, hydroxy, halogen or cyano;

L is —(CR$^4_2$)$_n$—, —C(O)NR$^4$— or —C(O)NR$^4$CH$_2$—;

each R$^4$ is the same or different and is hydrogen or lower alkyl;

R$^3$ is lower alkyl, cycloalkyl, phenyl optionally substituted by one or more R''';

R''' is halogen, cyano, lower alkyl, lower alkyl substituted by halogen or hydroxy, lower alkoxy or C(O)O—R$^4$; and n is 1, 2 or 3;

or pharmaceutically active acid addition salts thereof.

A further embodiment of the invention is a method of treating a disorder selected from the group consisting of Alzheimer's disease, cerebral amyloid angiopathy, hereditary cerebral hemorrhage with amyloidosis, Dutch-type (HCHWA-D), multi-infarct dementia, dementia pugilistica and Down syndrome, which comprises administering a compound of formula I

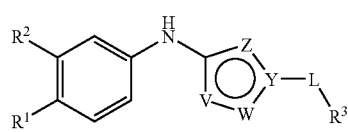
I wherein
R$^1$ is a five or six membered heteroaryl group optionally substituted by one or two R', selected from

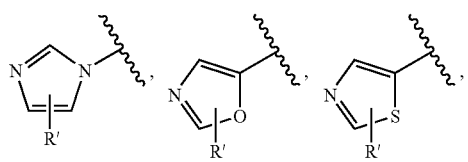

-continued

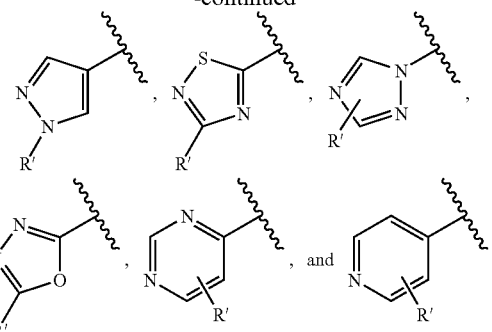

R' is lower alkyl;

R$^2$ is hydrogen, lower alkyl, lower alkoxy, hydroxy, halogen or cyano;

Z is N, C, O or S;

V is N, C(R''), O or S;

W is N, C(R''), O, or S;

Y is N or C with the proviso that only one of Z, V or W is O or S;

R'' is hydrogen, lower alkyl, lower alkyl substituted by halogen, hydroxy or amino, or is lower alkoxy, cyano, N(R$^4$)$_2$, C(O)N(R$^4$)$_2$, S(O)$_2$N(R$^4$)$_2$, C(O)R$^4$ or C(O)O—R$^4$;

L is a bond, —(CR$^4_2$)$_n$—, —N(R$^4$)—, —C(O)NR$^4$—, —CH(OR$^4$)—, —CH(NR$^4_2$)—, CR$^4_2$O— or —C(O)—;

each R$^4$ is the same or different and is hydrogen or lower alkyl;

R$^3$ is lower alkyl, aryl, a five or six membered heteroaryl group, cycloalkyl or heterocycloalkyl optionally substituted by one or more R''';

R''' is halogen, hydroxy, cyano, N(R$^4$)$_2$, lower alkyl, lower alkyl substituted by halogen, hydroxy or amino, or is lower alkoxy, lower alkoxy substituted by halogen, C(O)R$^4$, C(O)N(R$^4$)$_2$, S(O)$_2$N(R$^4$)$_2$, or C(O)O—R$^4$; and n is 1, 2 or 3;

or pharmaceutically active acid addition salts.

As used herein, the group

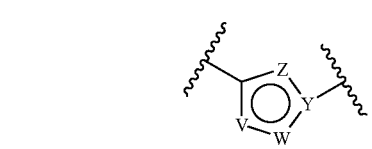

denotes the following 5-membered heteroaryl groups:

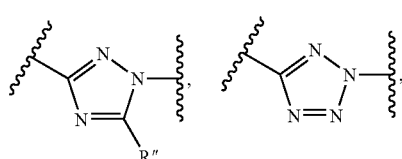

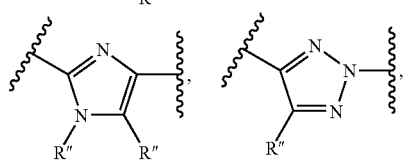

-continued

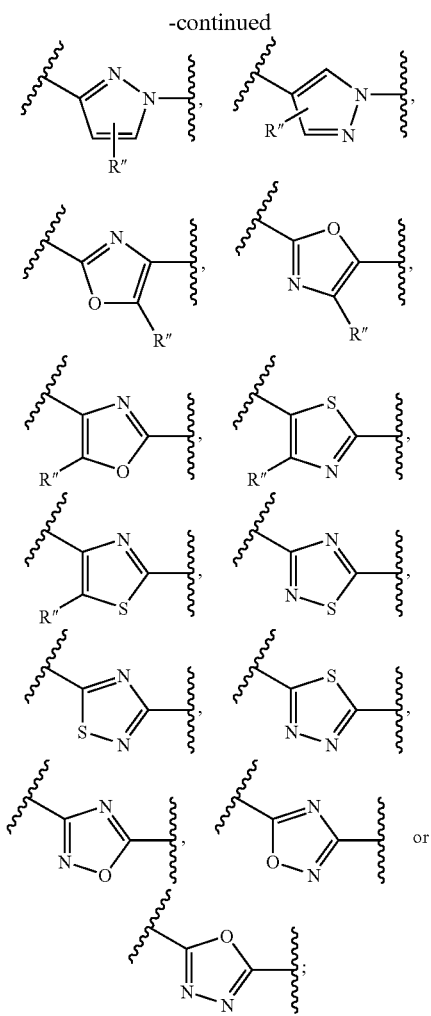

The invention includes all forms of optically pure enantiomers, racemates or diastereomeric mixtures for compounds of formula I.

Preferred compounds of formula I are compounds, wherein $R^1$ is

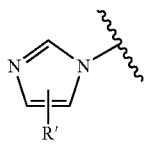

and R' is methyl.

Especially preferred are compounds from this group, wherein L is —C(R$^4$)$_2$— and $R^3$ is phenyl optionally substituted by R'''.

Such compounds are

5-[1-(4-chloro-benzyl)-1H-[1,2,4]triazol-3-ylamino]-2-(4-methyl-imidazol-1-yl)-benzonitrile;

5-[1-(3-chloro-benzyl)-1H-[1,2,4]triazol-3-ylamino]-2-(4-methyl-imidazol-1-yl)-benzonitrile;

5-[1-(2-chloro-benzyl)-1H-[1,2,4]triazol-3-ylamino]-2-(4-methyl-imidazol-1-yl)-benzonitrile;

5-[1-(4-cyano-benzyl)-1H-[1,2,4]triazol-3-ylamino]-2-(4-methyl-imidazol-1-yl)-benzonitrile;

5-(5-benzyl-[1,2,4]oxadiazol-3-ylamino)-2-(4-methyl-imidazol-1-yl)-benzonitrile;

5-(1-benzyl-1H-pyrazol-3-ylamino)-2-(4-methyl-imidazol-1-yl)-benzonitrile;

2-(4-methyl-imidazol-1-yl)-5-[1-(1-phenyl-ethyl)-1H-[1,2,4]triazol-3-ylamino]-benzonitrile;

5-[1-(4-fluoro-benzyl)-1H-pyrazol-3-ylamino]-2-(4-methyl-imidazol-1-yl)-benzonitrile;

2-(4-methyl-imidazol-1-yl)-5-[1-(3,4,5-trifluoro-benzyl)-1H-[1,2,4]triazol-3-ylamino]-benzonitrile;

5-[5-(2,6-dichloro-benzyl)-[1,2,4]oxadiazol-3-ylamino]-2-(4-methyl-imidazol-1-yl)-benzonitrile;

5-(1-benzyl-1H-[1,2,4]triazol-3-ylamino)-2-(4-methyl-imidazol-1-yl)-benzonitrile;

5-[1-(2,4-dichloro-benzyl)-1H-[1,2,4]triazol-3-ylamino]-2-(4-methyl-imidazol-1-yl)-benzonitrile;

2-(4-methyl-imidazol-1-yl)-5-[1-(3-trifluoromethyl-benzyl)-1H-[1,2,4]triazol-3-ylamino]-benzonitrile;

5-[1-(4-methyl-benzyl)-1H-[1,2,4]triazol-3-ylamino]-2-(4-methyl-imidazol-1-yl)-benzonitrile;

2-(4-methyl-imidazol-1-yl)-5-[1-(3,4,5-trifluoro-benzyl)-1H-pyrazol-3-ylamino]-benzonitrile;

5-(3-benzyl-[1,2,4]thiadiazol-5-ylamino)-2-(4-methyl-imidazol-1-yl)-benzonitrile;

5-[1-(3-chloro-benzyl)-1H-pyrazol-3-ylamino]-2-(4-methyl-imidazol-1-yl)-benzonitrile;

5-[1-(2,4-dichloro-benzyl)-1H-pyrazol-3-ylamino]-2-(4-methyl-imidazol-1-yl)-benzonitrile;

5-[1-(4-chloro-benzyl)-1H-pyrazol-3-ylamino]-2-(4-methyl-imidazol-1-yl)-benzonitrile;

5-[3-cyano-4-(4-methyl-imidazol-1-yl)-phenylamino]-2-(3,4,5-trifluoro-benzyl)-2H-pyrazole-3-carboxylic acid methyl ester;

5-[5-(1-hydroxy-1-methyl-ethyl)-1-(3,4,5-trifluoro-benzyl)-1H-pyrazol-3-ylamino]-2-(4-methyl-imidazol-1-yl)-benzonitrile;

1-(3-chloro-benzyl)-1H-[1,2,4]triazol-3-yl]-(4-pyridin-4-yl-phenyl)-amine;

[1-(4-fluoro-benzyl)-1H-pyrazol-3-yl]-[3-methoxy-4-(4-methyl-imidazol-1-yl)-phenyl]-amine;

[1-(4-chloro-benzyl)-1H-pyrazol-3-yl]-[3-methoxy-4-(4-methyl-imidazol-1-yl)-phenyl]-amine;

[1-(4-fluoro-benzyl)-5-methyl-1H-pyrazol-3-yl]-[3-methoxy-4-(4-methyl-imidazol-1-yl)-phenyl]-amine;

[1-(3-chloro-benzyl)-1H-[1,2,4]triazol-3-yl]-[3-methoxy-4-(4-methyl-imidazol-1-yl)-phenyl]-amine;

5-[3-methoxy-4-(4-methyl-imidazol-1-yl)-phenylamino]-2-(3,4,5-trifluoro-benzyl)-2H-pyrazole-3-carboxylic acid methyl ester;

[3-methoxy-4-(4-methyl-imidazol-1-yl)-phenyl]-[1-(3,4,5-trifluoro-benzyl)-1H-[1,2,4]triazol-3-yl]-amine;

2-[5-[3-methoxy-4-(4-methyl-imidazol-1-yl)-phenylamino]-2-(3,4,5-trifluoro-benzyl)-2H-pyrazol-3-yl]-propan-2-ol;

[1-(4-chloro-benzyl)-1H-[1,2,4]triazol-3-yl]-[3-methoxy-4-(4-methyl-imidazol-1-yl)-phenyl]-amine;

[3-methoxy-4-(4-methyl-imidazol-1-yl)-phenyl]-[1-(4-methyl-benzyl)-1H-[1,2,4]triazol-3-yl]-amine;

[3-methoxy-4-(4-methyl-imidazol-1-yl)-phenyl]-[1-(3-trifluoromethyl-benzyl)-1H-[1,2,4]triazol-3-yl]-amine; and

[3-methoxy-4-(4-methyl-imidazol-1-yl)-phenyl]-[1-(1-phenyl-ethyl)-1H-[1,2,4]triazol-3-yl]-amine.

Further preferred are compounds from this group for the above described use, wherein L is a bond and $R^3$ is phenyl optionally substituted by R''', for example 5-[1-(2,4-dichloro-phenyl)-5-methyl-1H-[1,2,4]triazol-3-ylamino]-2-(4-methyl-imidazol-1-yl)-benzonitrile;
2-(4-methyl-imidazol-1-yl)-5-(1-phenyl-1H-[1,2,4]triazol-3-ylamino)-benzonitrile;
2-(4-methyl-imidazol-1-yl)-5-[1-(2-trifluoromethyl-phenyl)-1H-[1,2,4]triazol-3-ylamino]-benzonitrile;
5-[1-(4-chloro-phenyl)-1H-[1,2,4]triazol-3-ylamino]-2-(4-methyl-imidazol-1-yl)-benzonitrile;
5-[1-(2-chloro-phenyl)-1H-[1,2,4]triazol-3-ylamino]-2-(4-methyl-imidazol-1-yl)-benzonitrile; and
[1-(2,4-dichloro-phenyl)-5-methyl-1H-[1,2,4]triazol-3-yl]-[3-methoxy-4-(4-methyl-imidazol-1-yl)-phenyl]-amine.

The present compounds of formula I and their pharmaceutically acceptable salts can be prepared by methods known in the art, for example, by processes described below, which processes comprise a) reacting a compound of formula

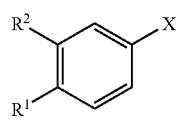

with a compound of formula

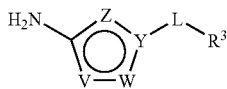

to obtain a compound of formula

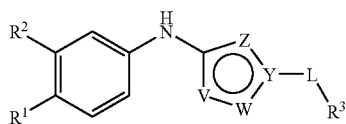

wherein X is halogen and the further groups have the meaning as described above and,
if desired, converting the compounds obtained into pharmaceutically acceptable acid addition salts;
or
b) reacting a compound of formula

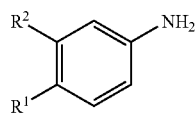

with a compound of formula

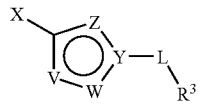

to obtain a compound of formula

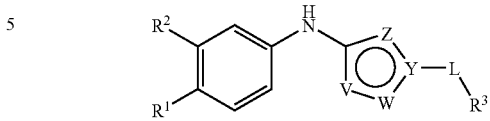

wherein X is halogen and the further groups have the meaning as described above, and,
if desired converting the compounds obtained into pharmaceutically acceptable acid addition salts;

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Anilines of general formula 2, which can be used as starting materials for the preparation of compounds of formula I can be prepared as described in the following schemes.

Nucleophilic substitution at room temperature or elevated temperature (e.g reflux or under pressure using a microwave oven) under neutral conditions or in the presence of a base (like e.g. potassium carbonate), neat or in a polar solvent (like e.g. THF or DMSO etc.) of substituted 4-nitro-phenyl halides 4 (X=F, Cl, Br, I) with compounds $R^1H$, (like 4-methylimidazole) yield nitro derivatives 3 (see scheme 1). Alternatively, nitro derivatives 3 can be prepared from suitable precursors 5 (PC=—CHO, —(CO)R', —(CO)OR' or —(CS)NH$_2$ with R'=lower alkyl), by applying standard reaction sequences for the formation of the substituent $R^1$. Nitro compounds 3 can be reduced to anilines 2 using generally known procedures, e.g. hydrogenation in the presence of a catalyst (like e.g. 10% palladium on carbon) in a solvent (like e.g. ethanol or ethyl acetate) or, by using a metal (like e.g. iron) or a metal salt (like e.g. stannous chloride) in a polar solvent (like e.g. acetic acid or tetrahydrofuran). Alternatively, anilines 2 can be prepared by introducing a substituent $R^1$ into N-protected aniline derivatives 6 (PG=protecting group) using generally known procedures, e.g. displacement reactions under catalytic conditions (like e.g. palladium(0) or copper(II) catalysis) or, by forming a group $R^1$ in N-protected aniline derivatives 7, respectively, and subsequently cleaving off the protecting group.

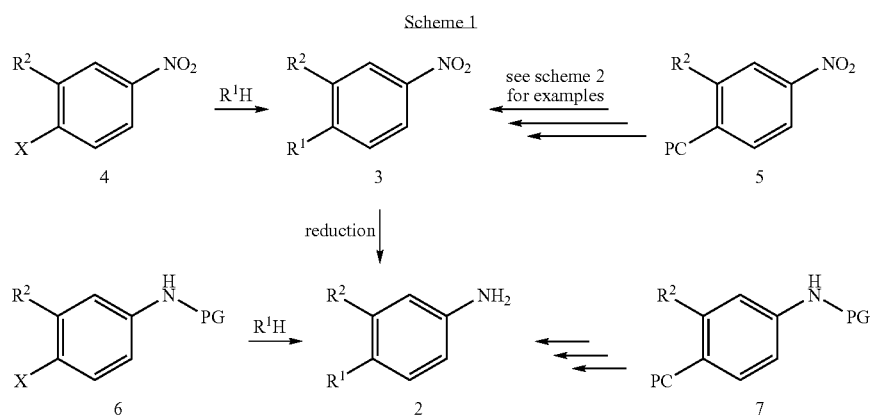

$R^1$ is a hetaryl group and PG is a N-protecting group, such as tert-butoxycarbonyl (Boc) group, X is a halide, PC is —CHO, —(CO)R' or —(CO)OR', —(CS)NH$_2$, R' is lower alkyl.

Heterocyclic anilines like the oxadiazole derivative 2a (see scheme 2) can be prepared from the corresponding esters 5a by conversion to the acylated hydrazide and subsequent cyclization to the oxadiazole 3a. Treatment of the aldehyde 5b with TosMIC (tosylmethyl isocyanide) yields the oxazole 3b. Ketones 5c can be converted into substizuted oxazoles 3c upon treatment with iodobenzene diacetate, trifluoromethanesulfonic acid and nitriles. Thiadiazoles 3d can be prepared from thioamides 5d in the presence of N,N-dimethylacetamide dimethyl acetal and hydroxyl-amine-O-sulfonic acid. Pyrimidines 3e can be prepared by building up the pyrimidine ring for example by reacting the 4-nitro-acetophenone derivative 5e with an ortho ester derivative (like e.g. the Bredereck reagent) and subsequent condensation with an amidine derivative (R'C(N)NH$_2$) to yield the nitro derivative 3e.

Reduction of nitro derivatives 3 provides the respective anilines 2.

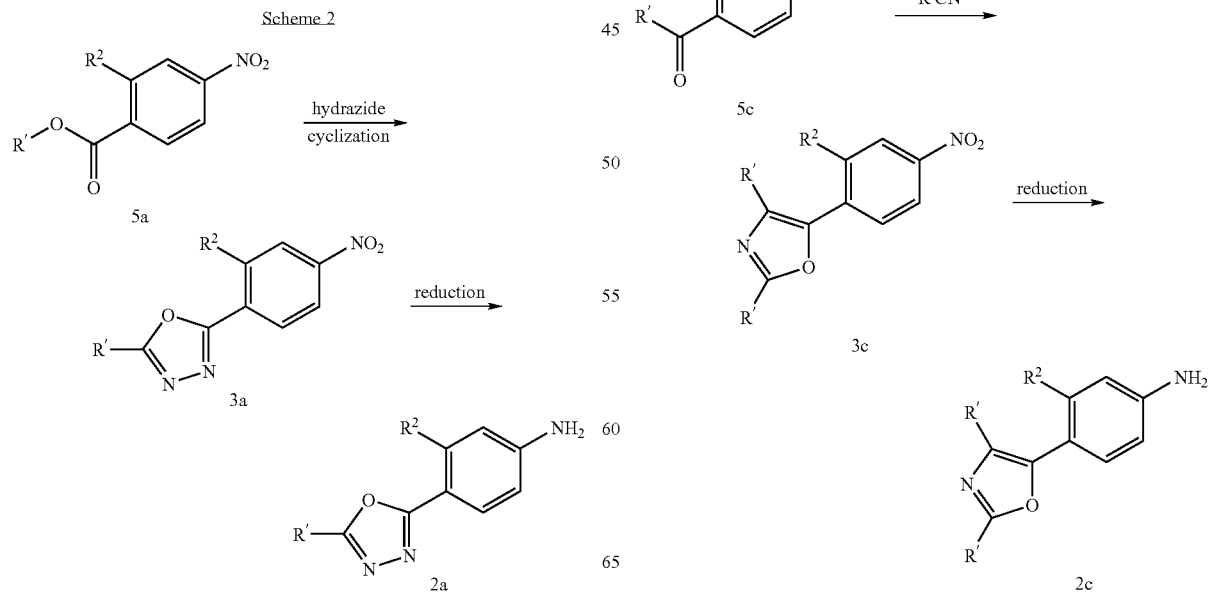

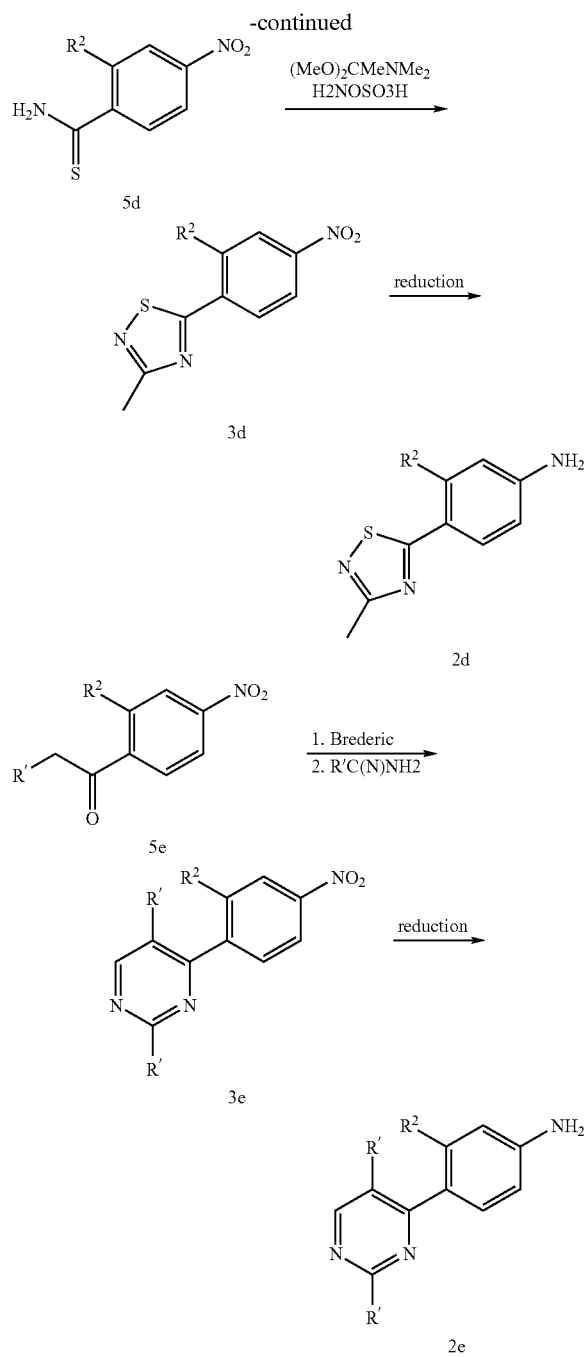

R' is lower alkyl.

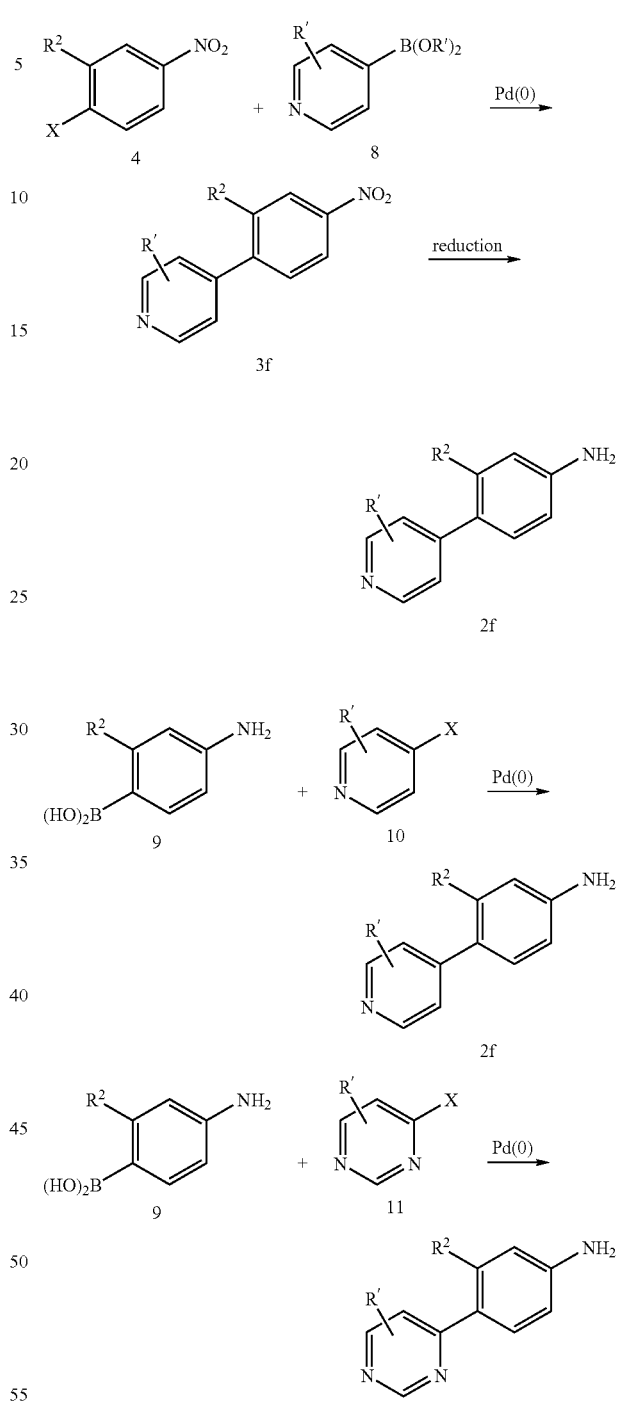

X is halide (like e.g. bromine or iodine), R' is lower alkyl or hydrogen

Heterocyclic anilines like the pyridine 2f or pyrimidine derivative 2g (see scheme 3) can be prepared by Suzuki coupling of the corresponding pyridine respectively pyrimidine halide with the corresponding aniline boronic acid respectively ester or by Suzuki coupling of the corresponding heterocyclic boronic acid or ester (like e.g. the pinacol ester) with the 4-halo-nitro-benzene derivative and subsequent reduction to the aniline or directly with the 4-halo-aniline. Aryl boronic acids and esters used as starting materials are either commercially available or readily prepared by methods known to one skilled in the art of organic synthesis such as treatment of the corresponding aryl bromides with bis(pinacolato)diboron in the presence of a palladium catalyst.

Heterocyclic anilines like the pyrazole derivative 2h (see scheme 4) can be prepared by Suzuki coupling of a 4-nitro-phenyl-boronic acid respectively ester (like e.g. 2-(2-methoxy-4-nitro-phenyl)-4,4,5,5-tetramethyl-[1,3,2]dioxaborolane) with a heteroaryl halide (like e.g. 1-methyl-4-iodo-1H-pyrazole) under palladium(II) catalysis in the presence of a base in polar or apolar medium under heating.

Scheme 4

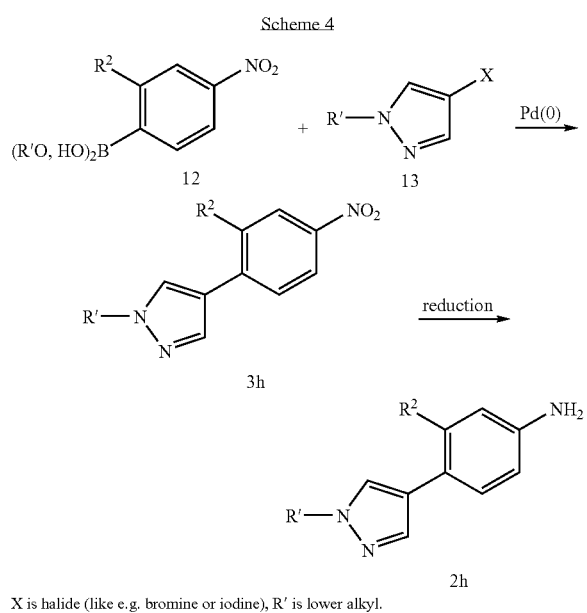

X is halide (like e.g. bromine or iodine), R' is lower alkyl.

Heterocyclic anilines, like the thiazole derivative 21 (see scheme 5), can be prepared from the corresponding halides 4 by palladium(0) (like e.g. palladium tetrakisphosphine) catalyzed Heck reaction with an alkyl substituted thiazole 14 in the presence of a base (like e.g. potassium acetate) in a polar solvent (like e.g. N,N-dimethylacetamide) under heating (e.g. to reflux or in a microwave oven).

Scheme 5

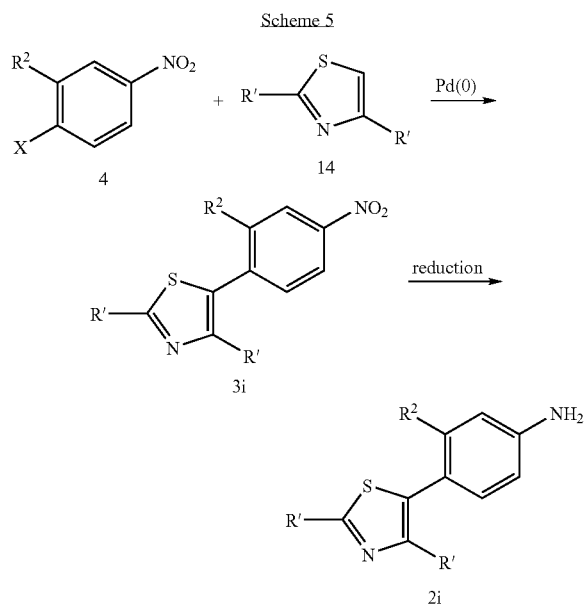

X is halide (like e.g. bromine or iodine, R' is lower alkyl.

Halides of general formula 15 (X preferably equals Br or Cl, more preferably Br), which can be used as starting materials for the preparation of compounds of formula I can be prepared as described in the following schemes.

Amines 2 with suitable substituents $R^1$ and $R^2$ can be subjected to a diazotation reaction in the presence of an appropriate halide source which provides the desired halides 15 (see scheme 6). Suitable reagents for preparation of bromides (X=Br) are e.g. t-butyl nitrite or isoamyl nitrite and copper (II)bromide in acetonitrile. Alternatively sodium nitrite in aqueous HBr solution in the presence of sodium bromide, copper bromide or copper sulphate can be used. Analogously the chlorides 15 (X=Cl) can be obtained by employing the corresponding chloride sources (copper chloride, HCl etc).

Scheme 6

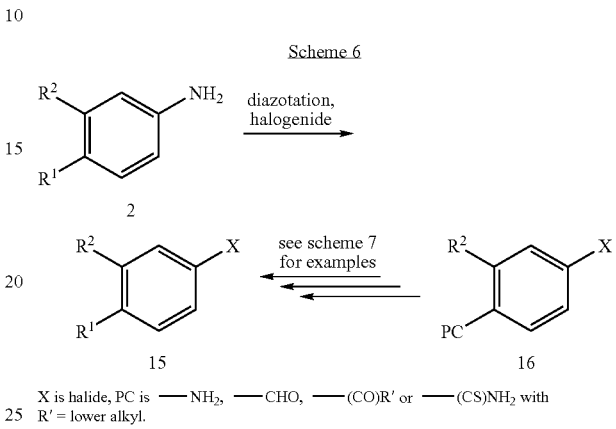

X is halide, PC is —NH$_2$, —CHO, —(CO)R' or —(CS)NH$_2$ with R' = lower alkyl.

Alternatively, halides 15 can be prepared from a suitable precursor 16 (PC=—NH$_2$, —CHO, —(CO)R' or —(CS)NH$_2$ with R'=lower alkyl), by applying standard reaction sequences for the formation of the substituent $R^1$ (see scheme 7).

Anilines 16a can be converted into imidazoles 15a (as described for example in EP1950211 A1, Exp 1.3-1.5) e.g. by sequential formylation (with acetic anhydride and formic acid) and alkylation (with chloroacetone in the presence of a base e.g. cesium carbonate and potassium iodide in DMF). Ring closure of intermediate 17 can then be achieved by heating with ammonium acetate and acetic acid neat or in xylene. Ketones 16b can be converted into substituted oxazoles 15b upon treatment with iodobenzene diacetate, trifluoromethanesulfonic acid and nitriles as described for example in WO2006/40192 A1, Exp. 46. Treatment of aldehyde 16c with TosMIC (tosylmethyl isocyanide) yields oxazole 15c. Thiadiazoles 15d can be prepared from thioamides 16d in the presence of N,N-dimethylacetamide dimethyl acetal and hydroxyl-amine-O-sulfonic acid. Pyrimidines 15e can be prepared by building up the pyrimidine ring for example by reacting the acetophenone derivative 16e with a ortho ester derivative (like e.g. the Brederick reagent) and subsequent condensation with an amidine derivative (R'C(N)NH$_2$) to yield pyrimidine 15e.

The starting materials 16 are either commercially available or readily prepared by methods known to one skilled in the art of organic synthesis.

Scheme 7

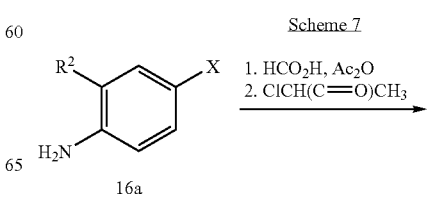

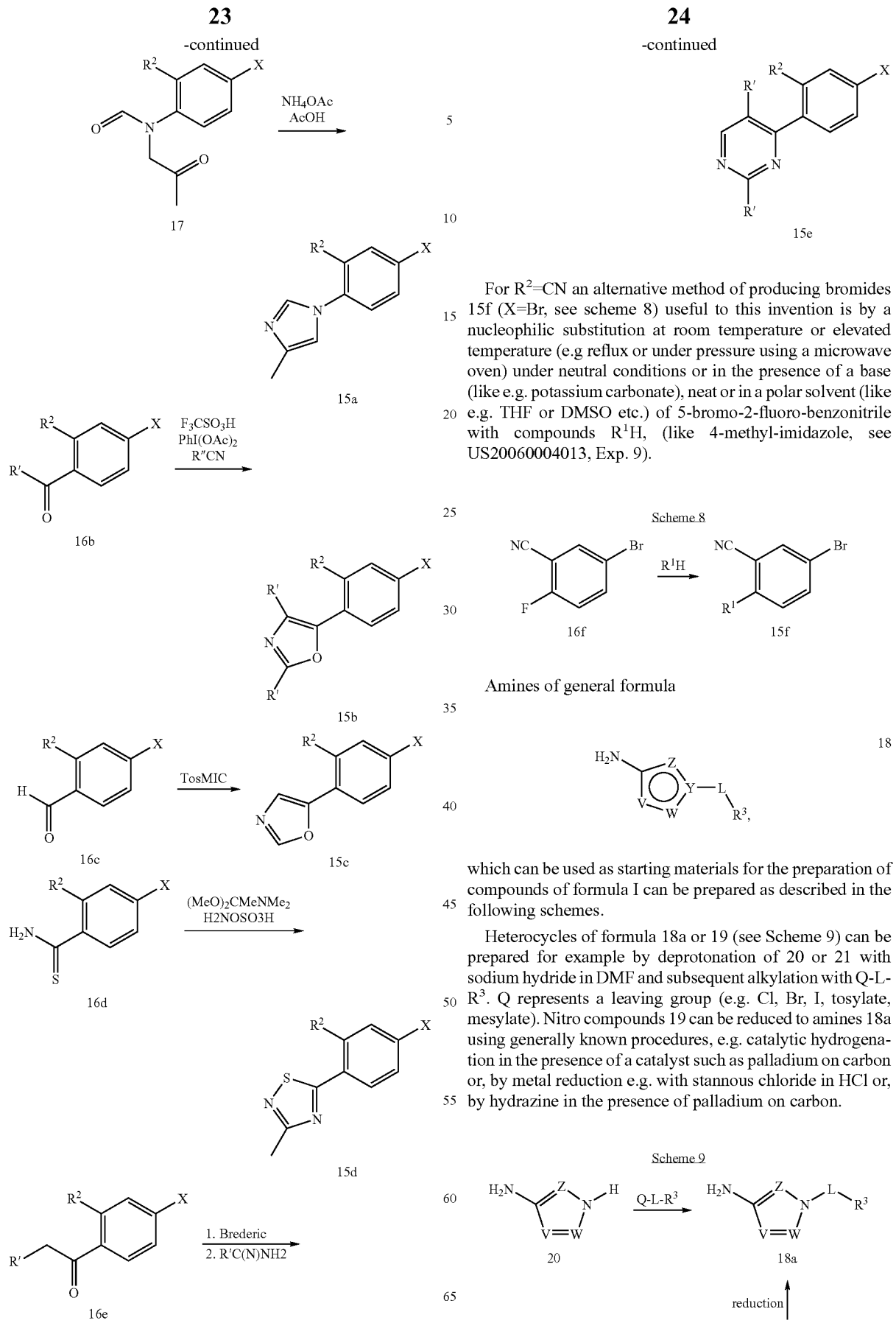

For R²=CN an alternative method of producing bromides 15f (X=Br, see scheme 8) useful to this invention is by a nucleophilic substitution at room temperature or elevated temperature (e.g reflux or under pressure using a microwave oven) under neutral conditions or in the presence of a base (like e.g. potassium carbonate), neat or in a polar solvent (like e.g. THF or DMSO etc.) of 5-bromo-2-fluoro-benzonitrile with compounds R¹H, (like 4-methyl-imidazole, see US20060004013, Exp. 9).

Amines of general formula which can be used as starting materials for the preparation of compounds of formula I can be prepared as described in the following schemes.

Heterocycles of formula 18a or 19 (see Scheme 9) can be prepared for example by deprotonation of 20 or 21 with sodium hydride in DMF and subsequent alkylation with Q-L-R³. Q represents a leaving group (e.g. Cl, Br, I, tosylate, mesylate). Nitro compounds 19 can be reduced to amines 18a using generally known procedures, e.g. catalytic hydrogenation in the presence of a catalyst such as palladium on carbon or, by metal reduction e.g. with stannous chloride in HCl or, by hydrazine in the presence of palladium on carbon.

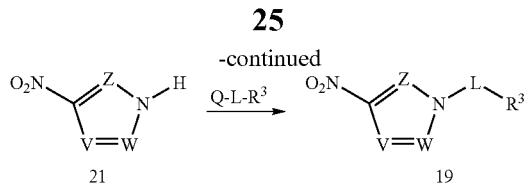

V, W, Z represent C or N, L represents —$(CR^4_2)_n$—, n is 1, 2 or 3 and Q represents a leaving group. The starting materials 20, 21 are either commercially available or readily prepared by methods known to one skilled in the art of organic synthesis. Examples for 20 are, but not limited to, 1H-[1,2,4]triazol-3-ylamine and 1H-pyrazol-3-ylamine. Examples for 21 are, but not limited to, 4-nitro-1H-pyrazole and 4-nitro-2H-[1,2,3]triazole.

Aminotriazoles 18b (see scheme 10) can e.g. be prepared according to M. Ruccia et al. J. Het. Chem. 1971, 8, 137-139 from formimidic acid ethyl ester by heating with anilines 22 which causes a rearrangement of the oxadiazole to give the amino triazole 23. Acidic cleavage of the benzoyl group then provides 18b.

Alternatively aminotriazoles 18b can be prepared from 3-amino-[1,2,4]triazoles by heating with suitable halides X-R24 in the presence of a base like potassium phosphate, potassium carbonate or cesium carbonate, with copper (I) iodide in a suitable solvent like DMSO, DMF, N-methyl-pyrrolidine as e.g. described in WO2007120333, Exp.7 or WO2005044785, Exp.139.

Scheme 10

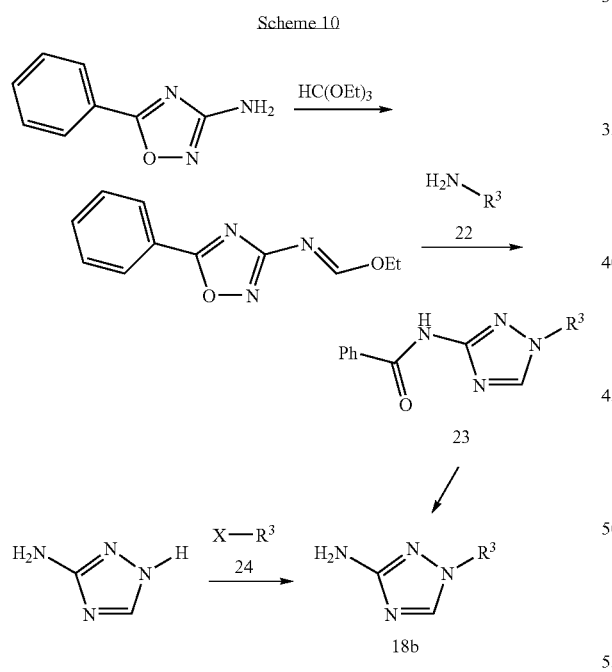

L represents bond, R³ represents aryl or heteroaryl, X represents halogen (preferably Br, I)

Aminopyrazoles 18c (see scheme 11) are either commercially available or can e.g. be prepared from suitable hydrazines 25 by cyclization with acrylonitrile in the presence of a base such as sodium ethoxide in ethanol and subsequent oxidation of the dihydropyrazole 26 with e.g. manganese dioxide in dichloromethane or with dichloro-5,6-dicyano-p-benzoquinone (DDQ) in dioxane as e.g. described in WO200754480 A1, Exp.3A and B. Hydrazines 25 are either commercially available or readily prepared by methods known to one skilled in the art of organic synthesis such as diazotation of suitable anilines followed by reduction of the diazonium compound to the aryl hydrazine by e.g. sodium sulfite.

Scheme 11

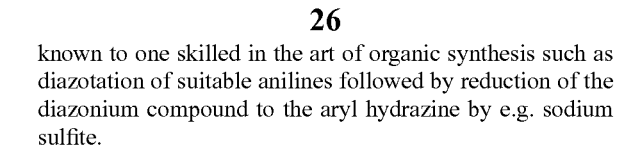

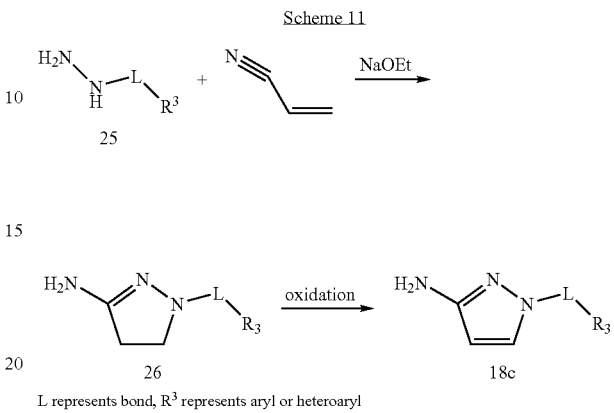

L represents bond, R³ represents aryl or heteroaryl

Aminopyrazoles 18d (see scheme 12) are either commercially available or can e.g. be prepared by coupling of suitable boronic acids (or boronic esters) 27 with pyrazole in the presence of copper (II) acetate and pyridine in methylene chloride as e.g. described in US200434008, Exp 1.1. The pyrazole 28 can then be nitrated with e.g. nitric acid and acetic anhydride or with nitric acid and sulphuric acid. Reduction of the nitro group using generally known procedures, e.g. catalytic hydrogenation in the presence of a catalyst such as palladium on carbon or, by metal reduction e.g. with stannous chloride in HCl provides aminopyrazoles 18d.

Scheme 12

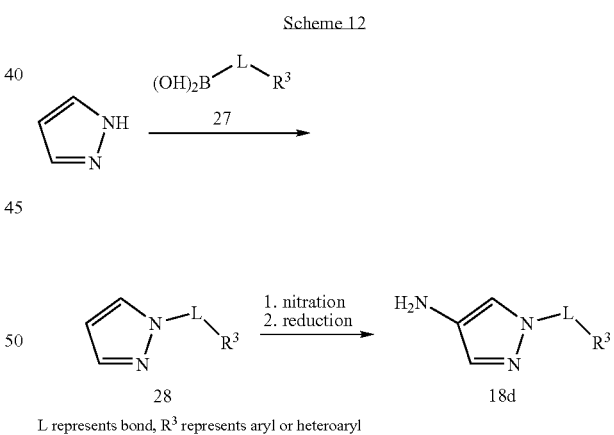

L represents bond, R³ represents aryl or heteroaryl

Amines of general formula

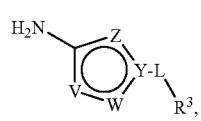

can also be prepared by construction of the central ring as described in the following schemes:

5-substituted 2-aminooxazoles 18e (see Scheme 13) can be prepared for example from aldehydes 29 by an α-bromination e.g. with bromine in dichloromethane or with tetrabutylammonium tribromide in acetonitrile. The α-bromoaldehydes 30 can then be condensed with urea by heating in a suitable solvent like DMF or ethanol.

Scheme 13

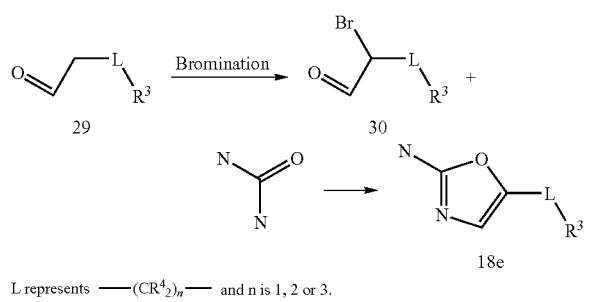

L represents —$(CR^4_2)_n$— and n is 1, 2 or 3.

3-Amino-1,2,4-oxadiazoles 18k (see Scheme 14) can be prepared e.g. according to M. J. Dimsdale, J. Het. Chem. 1981, 18, 37-41. Preparation of an acylcyanamide 41 from an acid chloride 40 and cyanamide is followed by ring closure to oxadiazole 18k with hydroxylamine in the presence of pyridine.

Scheme 14

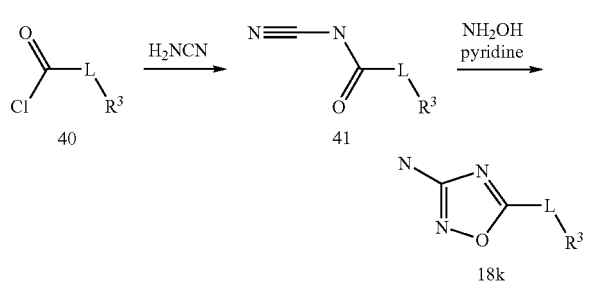

L represents —$(CR^4_2)_n$— or a bond

5-Amino-1,2,4-oxadiazoles 18m (see Scheme15) can e.g. be obtained by treatment of nitriles 42 with hydroxylamine which gives hydroxyamidines 43. Treatment with trichloroacetic acid and trichloroacetic anhydride yields the ring closed products 44. Heating with ammonia finally provides amino oxazoles 18m.

Scheme 15

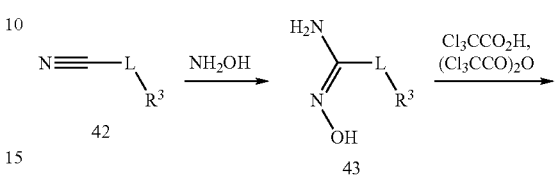

5-Amino-[1,2,4]thiadiazoles 18o (see Scheme16) can e.g. be prepared from suitable amidines 49 which are either commercially available or readily prepared by methods known to one skilled in the art of organic synthesis, e.g. treatment of suitable nitriles 42 with ammonium chloride and trimethylaluminium in toluene. Amidines 49 can be cyclized with perchloromethyl mercaptane and sodium hydroxide to provide the chlorothiadiazol 50 which can be converted to the amine with e.g. ammonia in ethanol or isopropanol. Alternatively thiadiazoles 18o can be prepared from suitable amides 51 which can be converted to the chloroamidines 52 by treatment with diemethyl sulphate, ammonium chloride and sodium hypochlorite as described e.g. EP1201661 A1, ref.exp. 24. Cyclization with potassium thiocyanate then provides aminothiadiazoles 18o.

Scheme 16

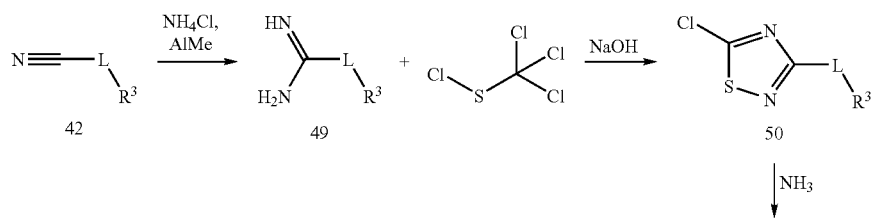

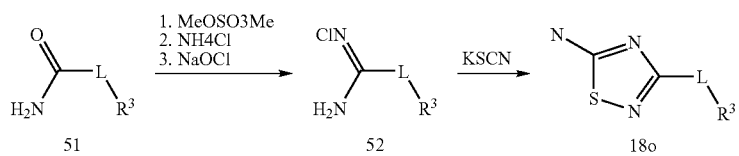

L represents —$(CR^4_2)_n$— or a bond

Halides of general formula 15 (X preferably equals Br or Cl, more preferably Br), and amines of general formula 18 can be coupled to provide compounds of general formula I (see Scheme 17). This reaction can e.g. be accomplished in the presence of a metal (for example Cu or Pd). A method for the coupling of heteroaryl amines with aryl halides is e.g. described by J. P. Schulte et al. Synlett 2007, 2331-6 who employ sodium phenolate, $Pd_2(dba)_3$, Xantphos as reagents and dioxane as solvent.

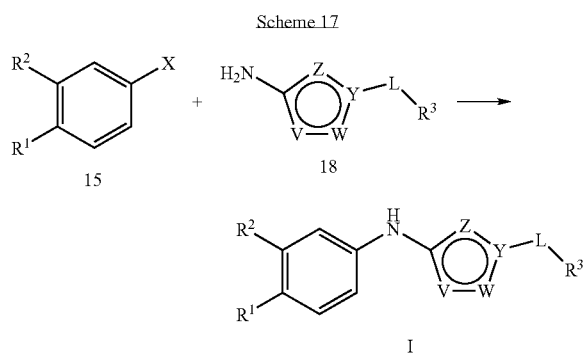

Alternatively, anilines of general formula 2 and halides of general formula 53 can be coupled to provide compounds of general formula I (see Scheme18). This reaction can e.g. be accomplished using generally known procedures, e.g. displacement reactions under catalytic conditions (like e.g. palladium(0) or copper(II) catalysis) or under thermal conditions or under basic conditions.

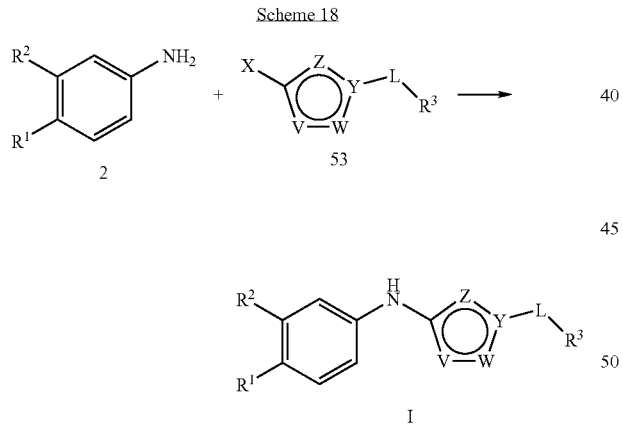

Compounds of general formula I can also be prepared starting from anilines 2 comprising the construction of the heteroaryl moiety (see Scheme19).

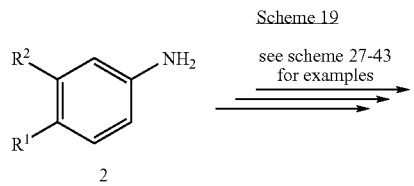

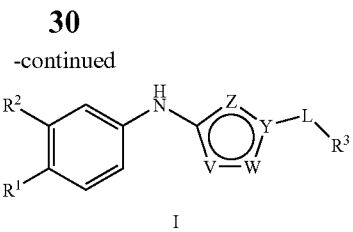

Example methods for these heteroaryl syntheses and methods for the preparation of useful intermediates are described in the following schemes.

Synthesis of intermediates 54 to 58 (see Scheme 20) can be accomplished using generally known procedures. Phenyl cyanamides 54 can e.g. be prepared by reaction of suitable anilines 2 with cyanogen bromide. Isothiocyanates 55 can e.g. be prepared from suitable anilines 2 by reaction with e.g. 1,1'thiocarbonyldi-2(1H)-pyridone, 1,1'thiocarbonyldiimidazole or thiophosgene. Ureas 56 can e.g. be prepared by reaction of suitable anilines 2 with sodium or potassium cyanate. Thioureas 57 can e.g. be prepared by reaction of suitable anilines 2 with sodium or ammonium thiocyanate or by reaction of suitable anilines 2 with benzoyl isothiocyanates followed by basic hydrolysis of the benzoly group with e.g. aqueous potassium carbonate. Guanidines 58 can e.g. be prepared by reaction of suitable anilines 2 with 1,3-di-boc-2-methylisothiourea followed by cleavage of the boc-groups with e.g. trifluoroacetic acid.

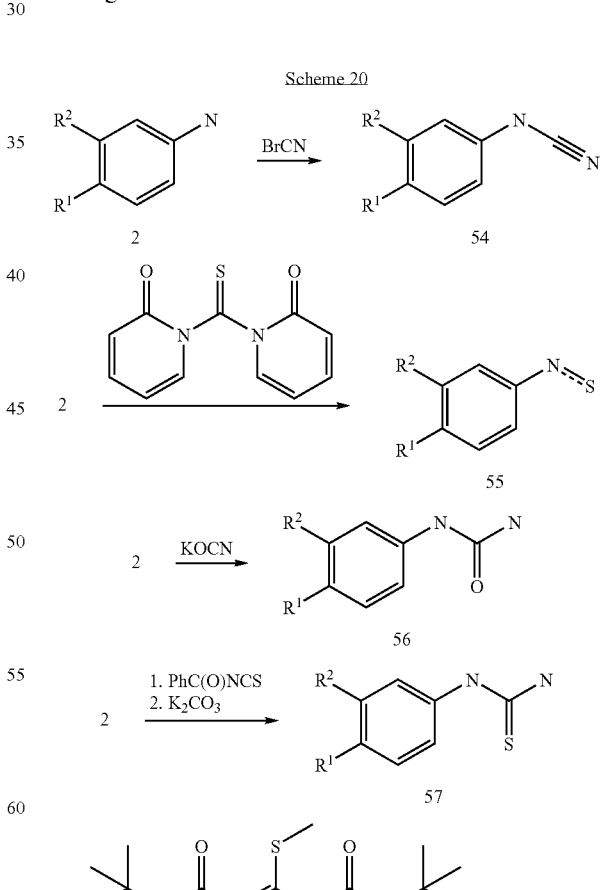

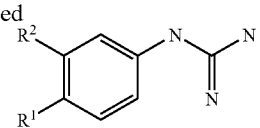

58

Oxazoles I-A6 (L=—(CR⁴₂)ₙ—, see Scheme 21) can e.g. be prepared by condensation of ureas 56 with suitable α-bromoaldehydes 30 by heating in a suitable solvent.

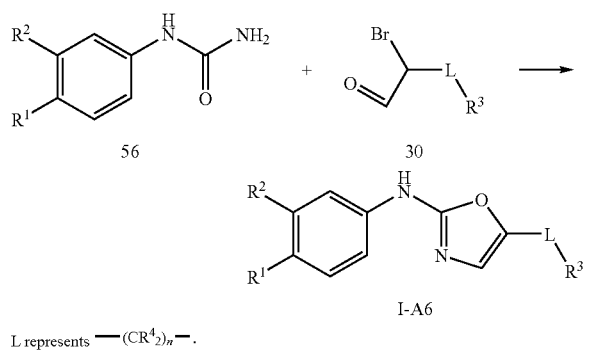

L represents —(CR⁴₂)ₙ—.

Oxazoles I-A6 (L=bond, see Scheme 22) can e.g. be prepared from α-azido carbonyl compound 59 by phosphine mediated cyclization with isothiocyanate 55 (e.g. by heating with triphenylphosphine in dioxane) as described in X. Ouyang et al., Bioorg. Med. Chem. Lett. 2006, 16, 1191-6. Azido compound 59 can e.g. be obtained by conversion of bromides 33 with sodium azide in acetone. Bromides 33 (with L=bond) can be prepared by α-bromination of suitable carbonyl compounds 31, for a summary of methods see for example "Comprehensive Organic Transformations, A Guide to Functional Group Preparations" R. C. Larock, VCH Publishers.

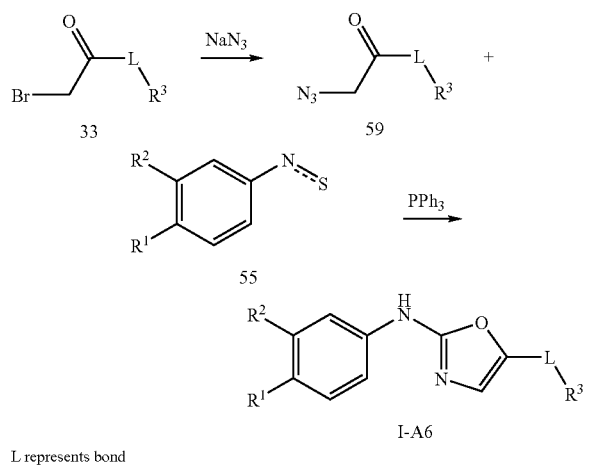

L represents bond

Synthesis of oxazoles I-A6 (see Scheme 23) can be accomplished e.g. by condensation of suitable α-bromo carbonyl compounds 33 (for synthesis see description of scheme 22) with suitable ureas 56 by heating in a solvent like DMF or ethanol. The reaction can also be carried out under microwave irradiation in the presence of aluminium oxide in dichloromethane (for L=bond) as described in M. Kidwai et al. Chemical Papers 2000, 54(4), 231-4.

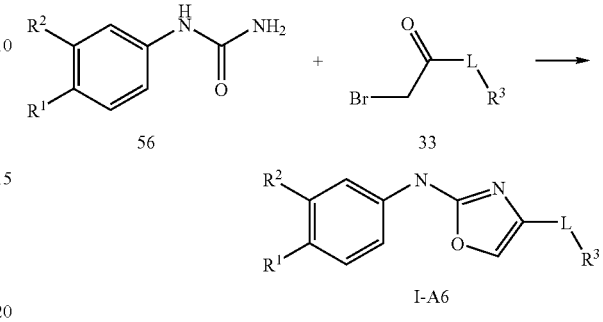

L represents bond

Oxadiazoles I-A8 (L=bond, see Scheme 24) can e.g. be prepared from suitable acylisothiocyanates 64 and anilines 2 (as e.g. described by T. G. M. Dhar et al. Bioorg. Med. Chem. Lett. 2002, 12, 3125-8). Acylisothiocyanates 64 can e.g. be obtained from the corresponding acids via conversion to their acid chlorides with e.g. oxalyl chloride and reaction with e.g. sodium thiocyanate. Thioureas 65 can be methylated with MeI and NaOH to yield the corresponding S-methylisothiocarbamoyl intermediates which cyclize upon treatment with hydroxylamine to provide the oxadiazoles I-A14.

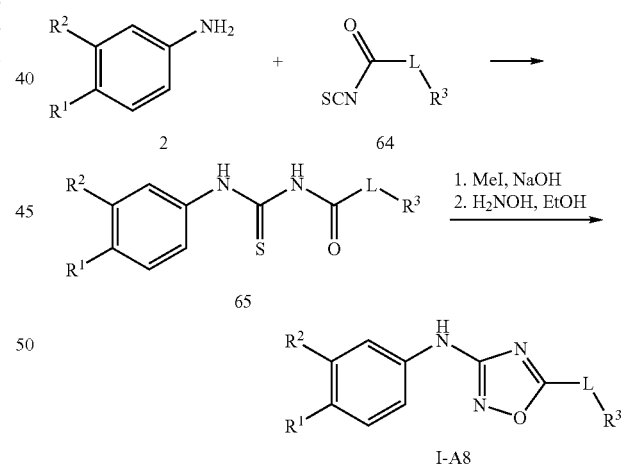

L represents bond

Oxadiazoles I-A9 (see Scheme 25) can e.g. be prepared by reaction of anilines 2 with 2-trichloromethyl oxazoles 44 (for example heating in ethanol or with DBU in DMSO) as e.g. described by I. Kumita et al. Nippon Noyaku Gakkaishi 2001, 26(1), 60-66. Compounds 44 (with L=—(CR⁴₂)ₙ— or bond) can e.g. be prepared from hydroxyamidines 43 as described in scheme 20 or from hydroxy guanidines (L=NR⁴) by treatment with trichloroacetic anhydride in THF as described by J. W. Tilley et al. Helv. Chim. Acta 1980, 63, 832-840.

Scheme 25

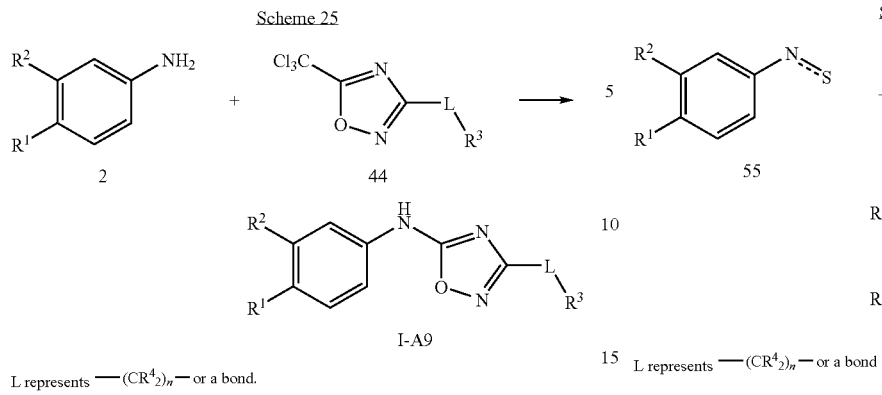

L represents —(CR⁴₂)ₙ— or a bond.

Thiadiazoles I-A7 (see Scheme 26) can e.g. be prepared as described by Y.-J. Wu et al. Tet. Lett. 2008, 49, 2869-71 by reaction of isothiocyanates 55 with suitable amidines 49 (L=—(CR$^4_2$)— or a bond) in the presence of diisopropyl-ethylamine in DMF to give thioureas 70. These cyclize upon treatment with diisopropyl azodicarboxylate (DIAD) to yield thiadiazoles I-A7.

Scheme 26

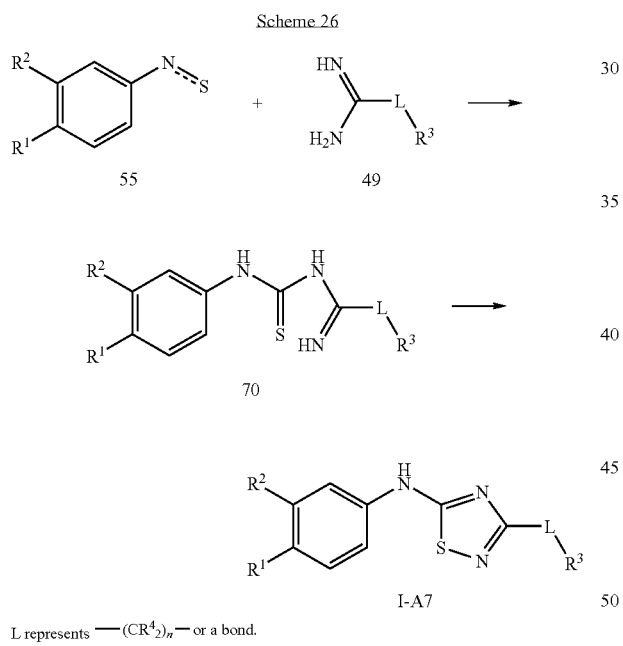

L represents —(CR⁴₂)ₙ— or a bond.

Oxadiazoles I-A10 (see Scheme 27) can e.g. be prepared by cyclization of isothiocyanates 55 with compounds 71 under heating in the presence of HgO in methanol as solvent. Hydrazides 71 (with L=—(CR$^4_2$)— or bond) can be readily prepared by methods known to one skilled in the art of organic synthesis such as conversion of the corresponding acids to their acid chloride and reaction with hydrazine or coupling of the corresponding acids with hydrazine in the presence of an coupling agent such as CDI or EDC or coupling of the corresponding acids with ter-butylcarbazate in the presence of an coupling agent such as HBTU followed by cleavage of the tert-butyloxycarbonyl group with e.g. TFA. Semicarbazides 71 or with the corresponding isocyanates OCN—R³.

Scheme 27

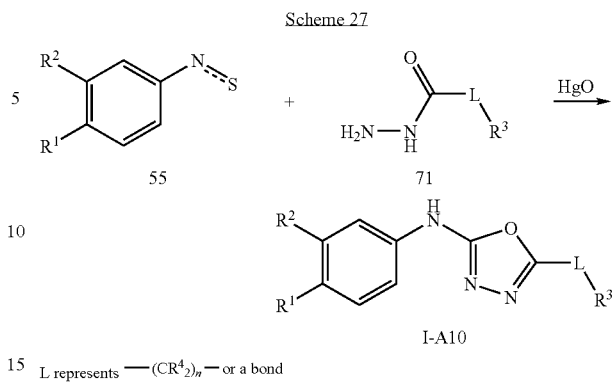

L represents —(CR⁴₂)ₙ— or a bond

Synthesis of esters 75 are described in the following schemes. 2-Amino-4-oxazolecarboxylic acid 84 (see scheme 28) is commercially available. It can be esterified and the product 85 can be coupled under palladium(0) catalysis with suitable aryl halides 15 (e.g. aryl bromides) to yield esters 75e. Alternatively the 2-chloro-oxazole derivative 86 (WO2007131953) can be coupled under basic conditions (e.g. with sodium hydride) with an aniline 2.

Compounds 75f can be prepared from the corresponding ureas 56 through condensation with ethyl bromopyruvate (WO2007141538).

Scheme 28

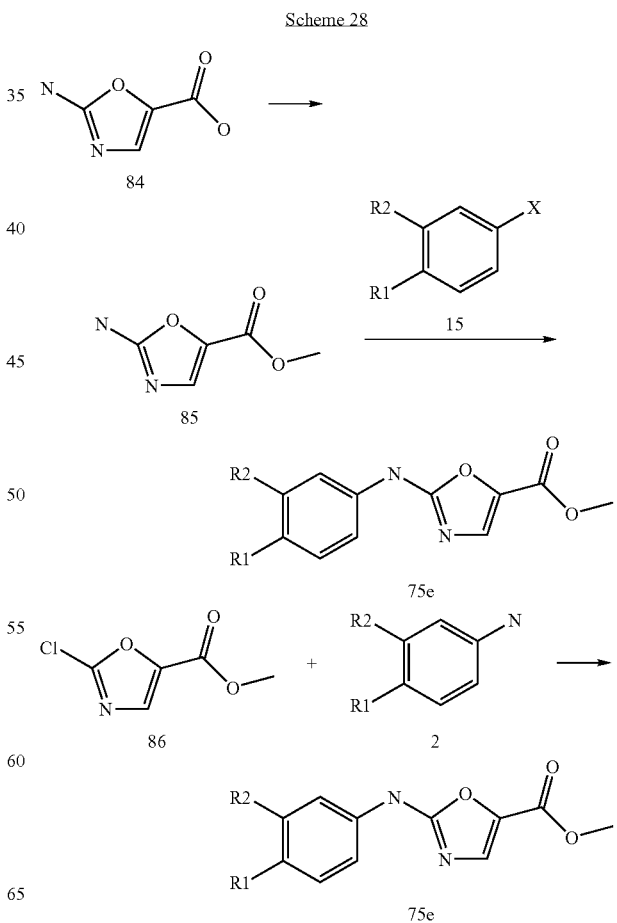

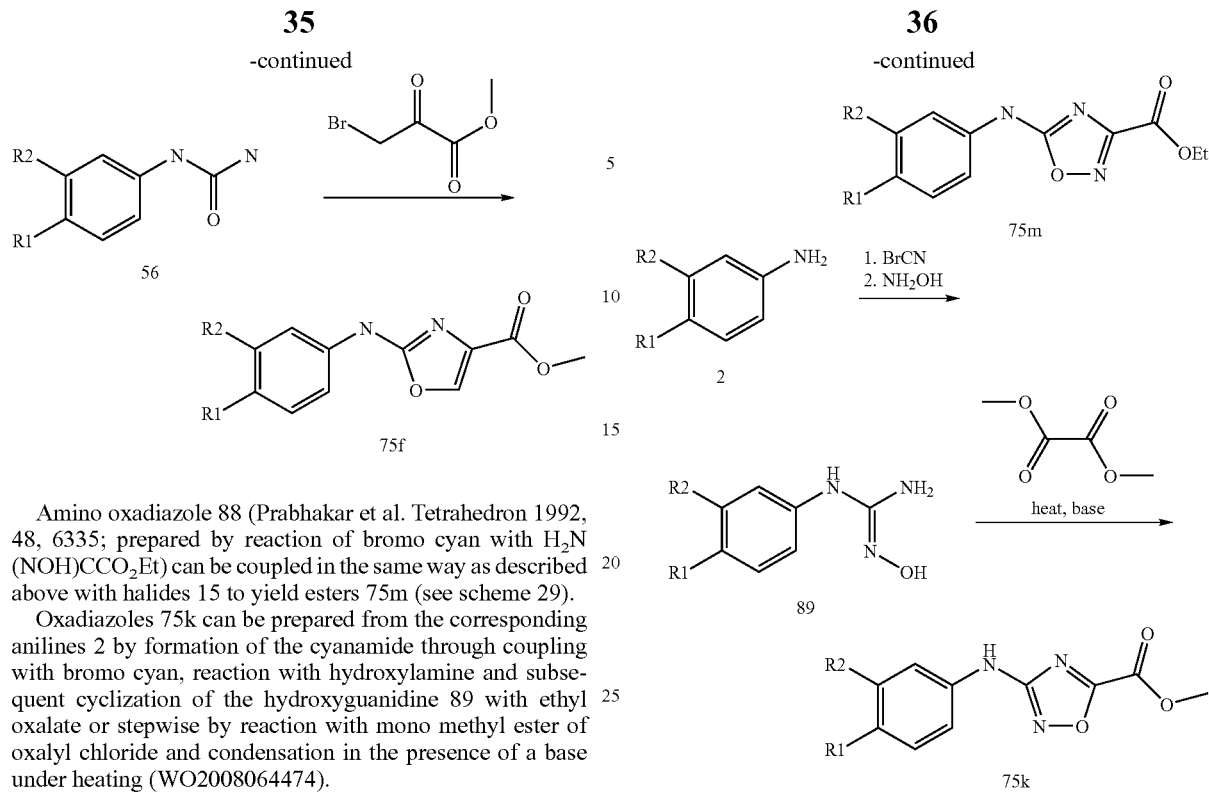

Amino oxadiazole 88 (Prabhakar et al. Tetrahedron 1992, 48, 6335; prepared by reaction of bromo cyan with H$_2$N(NOH)CCO$_2$Et) can be coupled in the same way as described above with halides 15 to yield esters 75m (see scheme 29).

Oxadiazoles 75k can be prepared from the corresponding anilines 2 by formation of the cyanamide through coupling with bromo cyan, reaction with hydroxylamine and subsequent cyclization of the hydroxyguanidine 89 with ethyl oxalate or stepwise by reaction with mono methyl ester of oxalyl chloride and condensation in the presence of a base under heating (WO2008064474).

Scheme 29

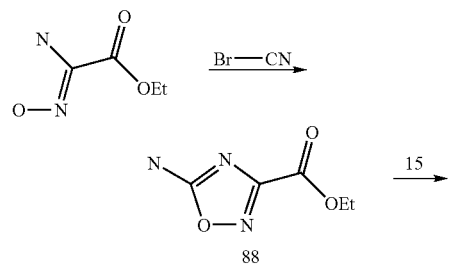

The tosyl derivative 90 (Bioorganic & Medicinal Chemistry (2003), 11(24), 5529-5537) can be reacted with nucleophiles (anilines 2) either under thermic conditions or under palladium(0) catalysis to give thiadiazoles 75n (see scheme 30). The amino thiadiazole 93 can be prepared from the amidine 92 (EP7470) and then reacted with an aryl bromides 15 under palladium (0) catalysis to the thiadiazoles 75o. Alternatively the chloro-thiadiazole 91 prepared by diazotation from the amino derivative 93 (EP7470) or from the amidine 92 (WO2001090095) can be reacted with anilines 2 under heating and/or under palladium (0) catalyzed conditions to give the product 75o.

Scheme 30

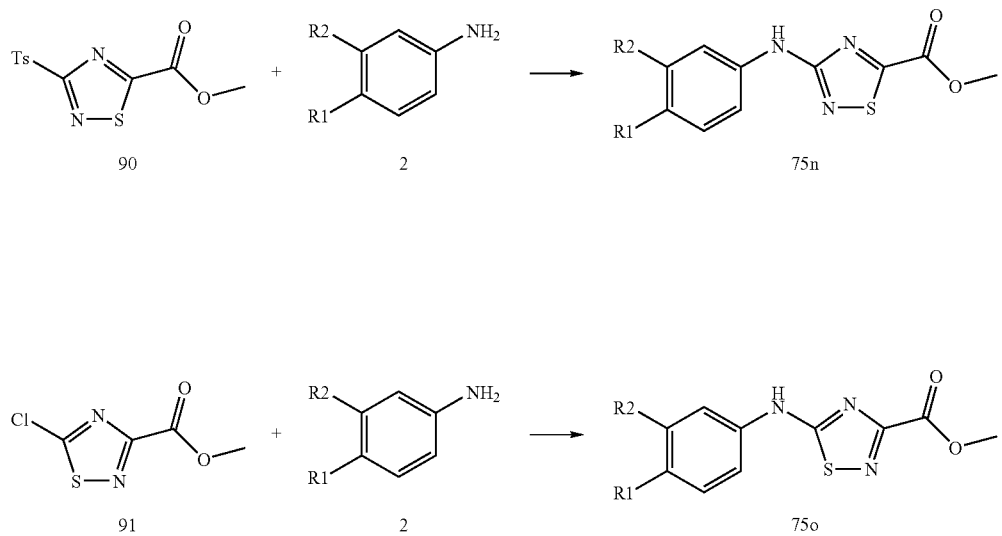

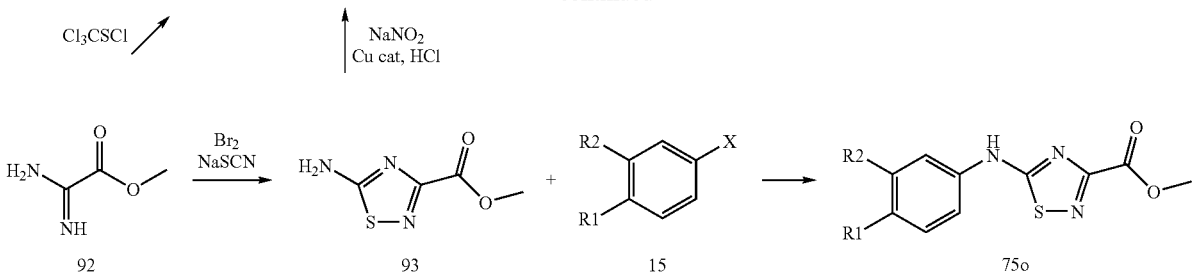

The oxadiazoles 75p can be prepared from the hydrazones 95 by oxidative cyclization with bromine (Werber, G. et. al J. Heterocycl. Chem., (1977) 14, 1385).

Scheme 31

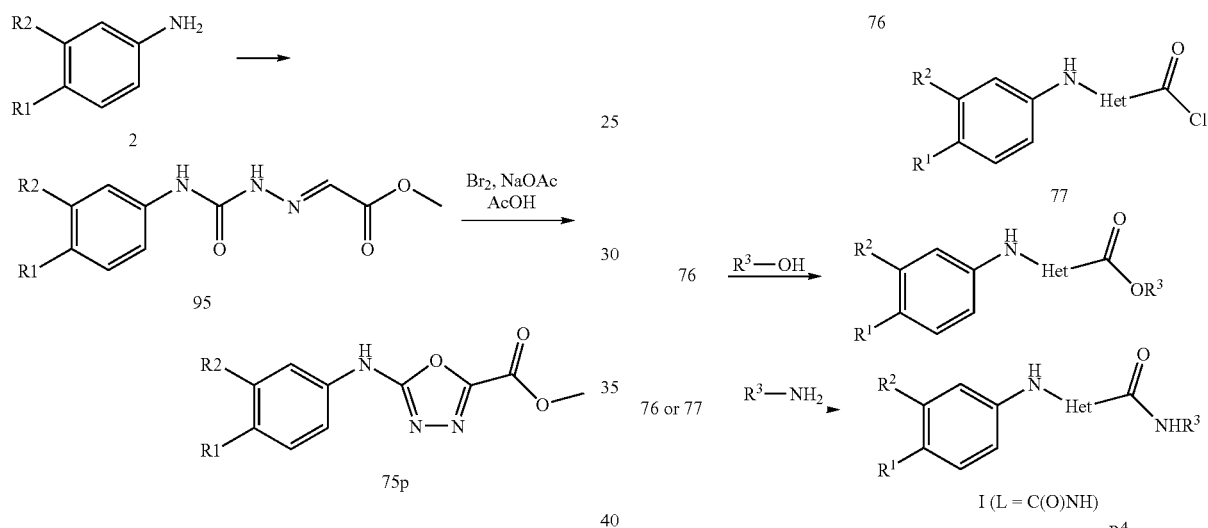

Certain compounds of general formula I can be prepared from the corresponding methyl or ethyl esters 75 (see scheme 32). Esters 75 can be converted to their carboxylic acids 76 by hydrolysis (e.g. with potassium hydroxides in water and ethanol) and to their acid chlorides 77 (e.g. with thionyl chloride). Esters can be prepared by e.g. transesterification from 75 or by ester formation from 76 with suitable alcohols $R^3$—OH. Amides of formula I (with L=C(O)NH) can be prepared from carboxylic acids 76 by standard procedures such as coupling with suitable amines $R^3$—$NH_2$ (e.g. in the presence of coupling agents like CDI or EDC) or from reaction of acid chlorides 77 with suitable amines $R^3$—$NH_2$. Alcohols of formula I (with L=bond and $R^3$ is lower alkyl substituted by hydroxy) can be prepared from esters 75 by reaction with e.g. lithium aluminum hydride ($R^4$=H) or with e.g. Grignard reagent.

Scheme 32

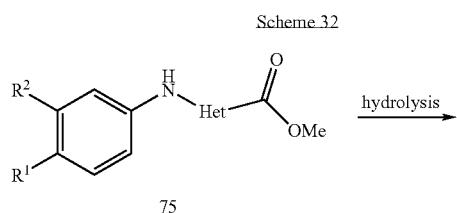

The compounds were investigated in accordance with the test given hereinafter.

Description of γ-Secretase Assay

Cellular γ-Secretase Assay

Human neuroglioma H4 cells overexpressing human APP were plated at 30,000 cells/well/200 μl in 96-well plates in IMDM media containing 10% FCS, 0.2 mg/l Hygromycin B and incubated for 2 h at 37° C., 5% $CO_2$ prior to adding test compounds.

Compounds for testing were dissolved in 100% $Me_2SO$ yielding in a 10 mM stock solution. Typically 12 μl of these solutions were further diluted in 1000 μl of IMDM media (w/o FCS). Subsequent 1:1 dilutions gave a ten point dose response curve. 100 μl of each dilution was added to the cells in 96-well plates. Appropriate controls using vehicle only and reference compound were applied to this assay. The final concentration of $Me_2SO$ was 0.4%.

After incubation for 22 hrs at 37° C., 5% $CO_2$, 50 μl supernatant was transferred into round-bottom 96-well polypropylene plates for detection of Aβ42. 50 μl assay buffer (50 mM Tris/Cl, pH 7.4, 60 mM NaCl, 0.5% BSA, 1% TWEEN 20) was added to the wells followed by the addition of 100 μl of detection antibody (ruthenylated BAP15 0.0625 μg/ml in assay buffer). 50 μl of a premix of capture antibody (biotinylated 6E10 antibody, 1 μg/ml) and Steptavidin-coated magnetic beads (Dynal M-280, 0.125 mg/ml) were preincubated for 1 hr at room temperature before adding the assay plates. Assay plates were incubated on a shaker for 3 hrs at room temperature and finally read in the Bioveris M8 Analyser according to the manufacturer's instructions (Bioveris).

Toxicity of compounds was monitored by a cell viability test of the compound-treated cells using a colorimetric assay (CellTiter 96™ AQ assay, Promega) according to the manufacturer's instructions. Briefly, after removal of 50 μl cell culture supernatant for detection of Aβ42, 20 μl of 1×MTS/PES solution was added to the cells and incubated for 30 min at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

The preferred compounds show a $IC_{50}$<1.0 (μM). In the list below are described the data for some compounds of the invention to the inhibition of Aβ42 secretion:

| Example No. | $EC_{50}$ Aβ42 (μM) |
| --- | --- |
| 3 | 0.100 |
| 7 | 0.220 |
| 9 | 0.619 |
| 10 | 0.790 |
| 11 | 0.513 |
| 12 | 0.410 |
| 14 | 0.245 |
| 15 | 0.572 |
| 16 | 0.185 |
| 17 | 0.099 |
| 18 | 0.694 |
| 19 | 0.548 |
| 20 | 0.809 |
| 22 | 0.380 |
| 23 | 0.580 |
| 24 | 0.280 |
| 25 | 0.380 |
| 26 | 0.099 |
| 27 | 0.031 |
| 29 | 0.097 |
| 30 | 0.130 |
| 32 | 0.580 |
| 36 | 0.090 |
| 39 | 0.150 |
| 40 | 0.170 |
| 42 | 0.500 |
| 43 | 0.250 |
| 45 | 0.290 |
| 46 | 0.500 |
| 47 | 0.130 |
| 48 | 0.490 |
| 49 | 0.700 |
| 50 | 0.240 |
| 51 | 0.420 |
| 52 | 0.220 |
| 53 | 0.330 |
| 54 | 0.230 |
| 55 | 0.320 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like.

Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

[5-(1,5-Dimethyl-1H-[1,2,4]triazol-3-ylamino)-2-(4-methyl-imidazol-1-yl)-benzonitrile

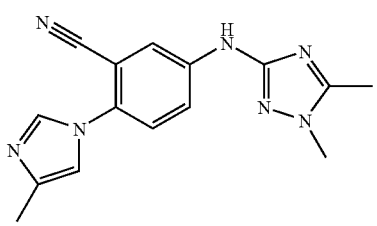

a) 5-Bromo-2-(4-methyl-imidazol-1-yl)-benzonitrile

This compound was prepared from 5-bromo-2-fluorobenzonitrile and 4-methylimidazole, as described in US2006/0004013.

b) [5-(1,5-Dimethyl-1H-[1,2,4]triazol-3-ylamino)-2-(4-methyl-imidazol-1-yl)-benzonitrile A mixture of 5-bromo-2-(4-methyl-imidazol-1-yl)-benzonitrile (50 mg, 0.19 mmol), 1,5-dimethyl-1H-1,2,4-triazol-3-amine (45 mg, 0.40 mmol), sodium phenoxide (66 mg, 0.57 mmol), tris(dibenzylideneacetone)dipalladium chloroform complex (3 mg, 0.003 mmol) and 4,5-bis(diphenylphosphino)-9,9-dimethylxanthene=Xanthphos (7 mg, 0.012 mmol) in 5 ml of dioxane was heated to 80° C. under argon for 2 hours. The mixture was diluted with water, extracted with ethyl acetate and the product purified by chromatography on silica gel using dichloromethane/methanol 9:1 v/v as an eluent. The title compound was obtained as a yellowish solid (6 mg, 11%). MS ISN (m/e): 292.3 (100) [(M−H)⁻].
$^1$H NMR (DMSO-D$_6$, 300 MHz): δ (ppm)=9.71 (s, 1H), 8.05 (s, 1H), 7.83 (s, 1H), 7.81 (dxd, 1H), 7.49 (d, 1H), 7.20 (s, 1H), 3.23 (s, 3H), 2.36 (s, 3H), 2.17 (s, 3H).

EXAMPLE 2

5-(1,5-Dimethyl-1H-pyrazol-3-ylamino)-2-(4-methyl-imidazol-1-yl)-benzonitrile

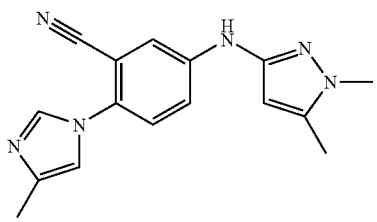

Prepared in analogy to example 1b) starting with 5-bromo-2-(4-methyl-imidazol-1-yl)-benzonitrile and 1,5-dimethyl-1H-pyrazol-3-ylamine. The title compound was obtained as a yellowish solid (Yield=36%). MS ISP (m/e): 293.2 (100) [(M+H)⁺].
$^1$H NMR (DMSO-D$_6$, 300 MHz): δ (ppm)=9.04 (s, 1H), 7.91 (s, 1H), 7.81 (s, 1H), 7.63 (dxd, 1H), 7.42 (d, 1H), 7.18 (t, 1H), 5.67 (s, 1H), 3.66 (s, 3H), 2.22 (s, 3H), 2.17 (s, 3H).

EXAMPLE 3

5-[1-(4-Chloro-benzyl)-1H-[1,2,4]triazol-3-ylamino]-2-(4-methyl-imidazol-1-yl)-benzonitrile

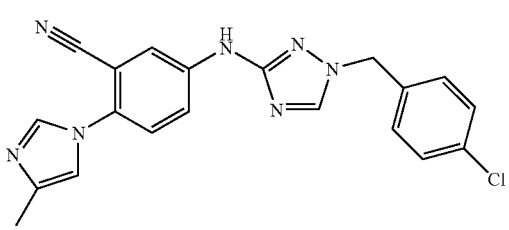

a) 1-(4-Chloro-benzyl)-1H-[1,2,4]triazol-3-ylamine

Sodium metal (460 mg, 20 mmol) was dissolved in 30 ml of methanol and 3-amino-1,2,4-triazole (1.682 g, 20 mmol) added. The resulting clear solution was stirred for 1 hour at room temperature, evaporated to dryness and the sodium salt suspended in 45 ml DMF. A solution of 4-chlorobenzyl chloride (3.221 g, 20 mmol) in 5 ml DMF was slowly added to the heavily stirred suspension obtained previously. After 3 hours at room temperature, a cloudy solution was obtained, which was stirred overnight at 20° C. The resulting mixture was concentrated in the rotatory evaporator and the oily residue treated with 100 ml of dichloromethane. Insoluble material was filtered off and the filtrate concentrated to give a brownish oil which solidified on standing. Chromatography on silica gel using dichloromethane/methanol 98:2 v/v as an eluent gave a poor separation of the two regioisomers. However, a pure fraction (215 mg, 5%) of the title compound could be obtained as a colorless solid after trituration with diethyl ether. MS ISP (m/e): 209.0 & 211.0 (100 & 43) [(M+H)$^+$].
$^1$H NMR (CDCl$_3$, 300 MHz): δ (ppm)=7.70 (s, 1H), 7.34 (d, 2H), 7.19 (d, 2H), 5.09 (s, 2H), 4.11 (s broad, 2H).

b) 5-[1-(4-Chloro-benzyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(4-chloro-benzyl)-1H-[1,2,4]triazol-3-ylamine. The title compound was obtained as a colorless solid (Yield=49%). MS ISP (m/e): 390.2 & 392.0 (100 & 48) [(M+H)$^+$].
$^1$H NMR (CDCl$_3$, 300 MHz): δ (ppm)=8.07 (d, 1H), 7.86 (s, 1H), 7.68 (s, 1H), 7.60 (dxd, 1H), 7.38 (d, 2H), 7.35-7.20 (m, 3H), 6.99 (s, 1H), 5.25 (s, 2H), 2.32 (s, 3H).

EXAMPLE 4

5-(2-Benzyl-2H-tetrazol-5-ylamino)-2-(4-methyl-imidazol-1-yl)-benzonitrile

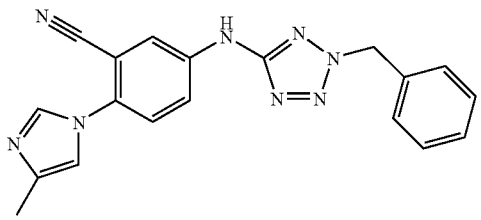

Prepared in analogy to example 1b) starting with 5-bromo-2-(4-methyl-imidazol-1-yl)-benzonitrile and 2-benzyl-2H-tetrazol-5-ylamine (Journal of the American Chemical Society 76, 923 (1954)). The title compound was obtained as a yellowish solid (Yield=29%). MS ISP (m/e): 357.1 (100) [(M+H)$^+$].
$^1$H NMR (CDCl$_3$, 300 MHz): δ (ppm)=8.05-7.95 (m, 2H), 7.75-7.65 (m, 2H), 7.45-7.30 (m, 6H), 7.00 (s, 1H), 5.73 (s, 2H), 2.32 (s, 3H).

EXAMPLE 5

5-(1-Cyclopropylmethyl-1H-[1,2,4]triazol-3-ylamino)-2-(4-methyl-imidazol-1-yl)-benzonitrile

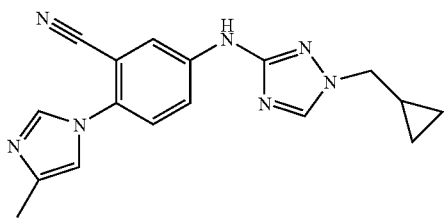

a) 1-Cyclopropylmethyl-1H-[1,2,4]triazol-3-ylamine

Prepared in analogy to example 3a) starting with 3-amino-1,2,4-triazole and methanesulfonic acid cyclopropylmethyl ester (Journal of the American Chemical Society 128, 3118 (2006)). The title compound was obtained as a brownish solid (Yield=25%). MS ISP (m/e): 138.1 (100) [M$^+$].

b) 5-(1-Cyclopropylmethyl-1H-[1,2,4]triazol-3-ylamino)-2-(4-methyl-imidazol-1-yl)-benzonitrile Prepared in analogy to example 1b) starting with 5-bromo-2-(4-methyl-imidazol-1-yl)-benzonitrile and 1-cyclopropyl-methyl-1H-[1,2,4]triazol-3-ylamine. The title compound was obtained as a yellowish foam (Yield=45%). MS ISP (m/e): 320.1 (100) [(M+H)$^+$].
$^1$H NMR (DMSO-D$_6$, 300 MHz): δ (ppm)=9.89 (s, 1H), 8.38 (s, 1H), 8.12 (s, 1H), 7.85-7.80 (m, 2H), 7.51 (d, 1H), 7.21 (s, 1H), 3.98 (d, 2H), 2.17 (s, 3H), 1.35-1.25 (m, 1H), 0.60-0.50 (m, 2H), 0.45-0.35 (m, 2H).

EXAMPLE 6

2-(4-Methyl-imidazol-1-yl)-5-(1-methyl-1H-[1,2,4]triazol-3-ylamino)-benzonitrile

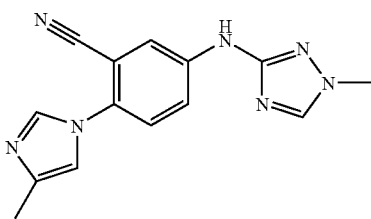

Prepared in analogy to example 1b) starting with 5-bromo-2-(4-methyl-imidazol-1-yl)-benzonitrile and 1-methyl-1H-[1,2,4]triazol-3-ylamine. The title compound was obtained as a colorless solid (Yield=36%). MS ISP (m/e): 280.1 (100) [(M+H)$^+$].
$^1$H NMR (DMSO-D$_6$, 300 MHz): δ (ppm)=9.86 (s, 1H), 8.29 (s, 1H), 8.08 (s, 1H), 7.90-7.80 (m, 2H), 7.51 (d, 1H), 7.21 (s, 1H), 3.82 (s, 3H), 2.18 (s, 3H).

EXAMPLE 7

5-[1-(3-Chloro-benzyl)-1H-[1,2,4]triazol-3-ylamino]-2-(4-methyl-imidazol-1-yl)-benzonitrile

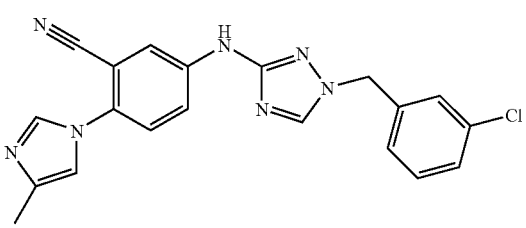

a) 1-(3-Chloro-benzyl)-1H-[1,2,4]triazol-3-ylamine

Prepared in analogy to example 3a) starting with 3-amino-1,2,4-triazole and 3-chloro benzyl chloride. The title compound was obtained as a colorless solid (Yield=9%). MS ISP (m/e): 211.0 & 209.0 (43 & 100) [M$^+$].

¹H NMR (DMSO-D₆, 300 MHz): δ (ppm)=8.12 (s, 1H), 7.40-7.35 (m, 4H), 7.31 (d, 1H), 7.22 (dxd, 1H), 5.29 (s, 2H), 5.13 (s, 2H).

b) 5-[1-(3-Chloro-benzyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(3-chloro-benzyl)-1H-[1,2,4]triazol-3-ylamine. The title compound was obtained as a yellowish solid (Yield=64%). MS ISP (m/e): 390.1 (100) [(M+H)⁺].

¹H NMR (DMSO-D₆, 300 MHz): δ (ppm)=9.93 (s, 1H), 8.53 (s, 1H), 8.05 (s, 1H), 7.81 (s, 1H), 7.80 (d, 1H), 7.55-7.35 (m, 4H), 7.30 (d, 1H), 7.20 (d, 1H), 5.38 (s, 2H), 2.17 (s, 3H).

EXAMPLE 8

5-[1-(4-Methoxy-benzyl)-1H-[1,2,4]triazol-3-ylamino]-2-(4-methyl-imidazol-1-yl)-benzonitrile

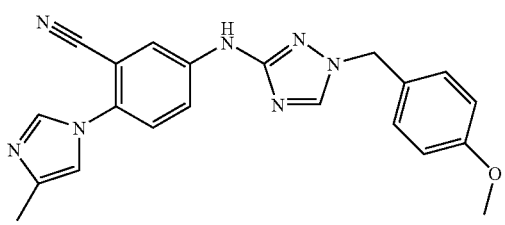

a) 1-(4-Methoxy-benzyl)-1H-[1,2,4]triazol-3-ylamine

Prepared in analogy to example 3a) starting with 3-amino-1,2,4-triazole and 4-methoxy benzyl chloride. The title compound was obtained as a colorless solid, MS ISP (m/e): 205.2 (100) [(M+H)⁺].

b) 5-[1-(4-Methoxy-benzyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(4-methoxy-benzyl)-1H-[1,2,4]triazol-3-ylamine. The title compound was obtained as a colorless oil (Yield=34%). MS ISP (m/e): 386.2 (100) [(M+H)⁺].

¹H NMR (CDCl₃, 300 MHz): δ (ppm)=8.09 (m, 1H), 7.76 (s, 1H), 7.66 (s, 1H), 7.61-7.57 (m, 1H), 7.30-7.26 (m, 3H), 7.08 (br s, 1H), 6.99 (s, 1H), 6.95-6.91 (m, 2H), 5.20 (s, 2H), 3.82 (s, 3H), 2.31 (d, 3H).

EXAMPLE 9

5-[1-(2-Chloro-benzyl)-1H-[1,2,4]triazol-3-ylamino]-2-(4-methyl-imidazol-1-yl)-benzonitrile

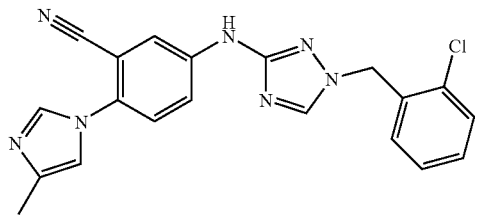

a) 1-(2-Chloro-benzyl)-1H-[1,2,4]triazol-3-ylamine

Prepared in analogy to example 3a) starting with 3-amino-1,2,4-triazole and 2-chloro benzyl chloride. The title compound was obtained as a colorless oil (Yield=11%). MS ISP (m/e): 209.0 & 211.0 (100 & 44) [(M+H)⁺].

¹H NMR (DMSO-D₆, 300 MHz): δ (ppm)=9.11 (s, 1H), 7.47 (dxd, 1H), 7.40-7.30 (m, 2H), 7.19 (dxd, 1H), 5.29 (s, 2H), 5.23 (s, 2H).

b) 5-[1-(2-Chloro-benzyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(2-chloro-benzyl)-1H-[1,2,4]triazol-3-ylamine. The title compound was obtained as a colorless solid (Yield=11%). MS ISP (m/e): 390.3 (100) [(M+H)⁺].

¹H NMR (DMSO-D₆, 300 MHz): (ppm)=9.96 (s, 1H), 8.51 (s, 1H), 8.08 (s, 1H), 7.83 (s, 1H), 7.79 (dxd, 1H), 7.55-7.45 (m, 2H), 7.45-7.35 (m, 2H), 7.31 (dxd, 1H), 7.20 (s, 1H), 5.46 (s, 2H), 2.17 (s, 3H).

EXAMPLE 10

5-[1-(4-Cyano-benzyl)-1H-[1,2,4]triazol-3-ylamino]-2-(4-methyl-imidazol-1-yl)-benzonitrile

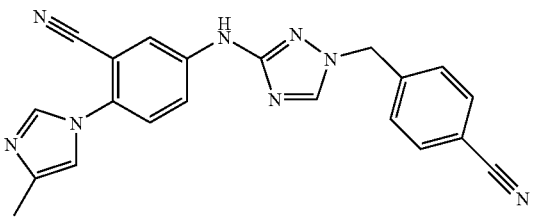

a) 4-(3-Amino-[1,2,4]triazol-1-ylmethyl)-benzonitrile

3-Amino-1,2,4-triazole (883 mg, 10.5 mmol) was dissolved in DMF (20 ml) under argon atmosphere, sodium hydride (55%, 436 mg, 10 mmol) added at rt in small portions and stirred at rt for 1 hour. To the reaction mixture alpha bromotolunitrile (1.96 g, 10 mmol) was added and stirred at rt overnight. TLC: finished: The reaction mixture was poured onto water, extracted with ethyl acetate and water, the organic layers combined, dried over Na$_2$SO$_4$, filtered and the solvents evaporated. Purification by flash chromatography with CH$_2$Cl$_2$/MeOH 100:0 to 90:10; 35 min over a 100 g silica-gel column gave 650 mg (yield: 32.6%) white solid. MS ISP (m/e): 200.2 (100) [(M+H)$^+$].

b) 5-[1-(4-Cyano-benzyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 4-(3-amino-[1,2,4]triazol-1-ylmethyl)-benzonitrile. The title compound was obtained as an off-white solid (Yield=36%). MS ISP (m/e): 381.2 (100) [(M+H)$^+$].
$^1$H NMR (DMSO, 300 MHz): δ (ppm)=9.94 (m, 1H), 8.54 (m, 1H), 8.02 (m, 1H), 7.88-7.79 (m, 4H), 7.51-7.47 (m, 3H), 7.20 (m, 1H), 5.49 (s, 2H), 2.17 (s, 3H).

EXAMPLE 11

5-(5-Benzyl-[1,2,4]oxadiazol-3-ylamino)-2-(4-methyl-imidazol-1-yl)-benzonitrile

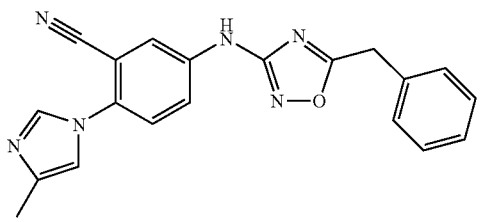

Prepared in analogy to example 1b) starting with 5-bromo-2-(4-methyl-imidazol-1-yl)-benzonitrile and 5-benzyl-[1,2,4]oxadiazol-3-ylamine (Zeitschrift für Chemie 14, 94 (1974)). The title compound was obtained as a light yellow solid (Yield=41%). MS ISP (m/e): 357.1 (100) [(M+H)$^+$].
$^1$H NMR (CDCl$_3$, 300 MHz): δ (ppm)=7.89 (m, 1H), 7.69-7.64 (m, 2H), 7.39-7.30 (m, 5H), 7.22-7.04 (m, 1H), 7.01-6.99 (m, 2H), 4.19 (s, 2H), 2.31 (s, 3H).

EXAMPLE 12

5-(1-Benzyl-1H-pyrazol-3-ylamino)-2-(4-methyl-imidazol-1-yl)-benzonitrile

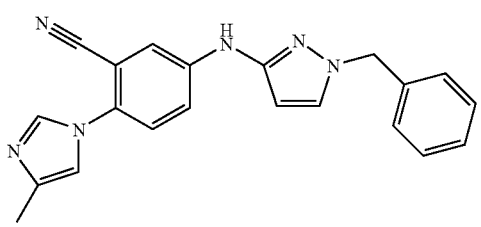

Prepared in analogy to example 1b) starting with 5-bromo-2-(4-methyl-imidazol-1-yl)-benzonitrile and 1-benzyl-1H-pyrazol-3-ylamine. The title compound was obtained as a yellow solid (Yield=74%). MS ISP (m/e): 355.2 (100) [(M+H)$^+$].
$^1$H NMR (CDCl$_3$, 300 MHz): δ (ppm)=7.66-7.63 (m, 2H), 7.40-7.32 (m, 7H), 7.23 (m, 1H), 6.96 (s, 1H), 6.28 (s, 1H), 5.97 (d, 1H), 5.23 (s, 2H), 2.30 (s, 3H).

EXAMPLE 13

5-[1-(4-Fluoro-phenyl)-5-methyl-1H-[1,2,4]triazol-3-ylamino]-2-(4-methyl-imidazol-1-yl)-benzonitrile

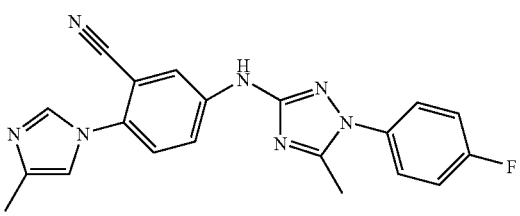

Prepared in analogy to example 1b) starting with 5-bromo-2-(4-methyl-imidazol-1-yl)-benzonitrile and 1-(4-fluoro-phenyl)-5-methyl-1H-[1,2,4]triazol-3-ylamine (prepared in analogy to Gazzetta Chimica Italiana 29, 105 (1899)). The title compound was obtained as a slightly brownish solid (Yield=24%). MS ISP (m/e): 374.1 (100) [(M+H)$^+$].
$^1$H NMR (DMSO, 300 MHz): δ (ppm)=9.99 (s, 1H), 8.07 (d, 1H), 7.91 (dxd, 1H), 7.86 (d, 1H), 7.75-7.65 (m, 2H), 7.53 (d, 1H), 7.44 (t, 2H), 7.22 (s, 1H), 2.46 (s, 3H), 2.19 (s, 3H).

EXAMPLE 14

5-[1-(2,4-Dichloro-phenyl)-5-methyl-1H-[1,2,4]triazol-3-ylamino]-2-(4-methyl-imidazol-1-yl)-benzonitrile

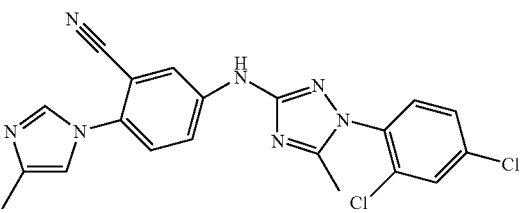

Prepared in analogy to example 1b) starting with 5-bromo-2-(4-methyl-imidazol-1-yl)-benzonitrile and 1-(2,4-dichloro-phenyl)-5-methyl-1H-[1,2,4]triazol-3-ylamine (prepared in analogy to Gazzetta Chimica Italiana 29, 105 (1899)). The title compound was obtained as a slightly brownish solid (Yield=54%). MS ISP (m/e): 424.2 & 426.0 (100 & 76) [(M+H)$^+$].

$^1$H NMR (DMSO, 300 MHz): δ (ppm)=10.00 (s, 1H), 7.99 (d, 2H), 7.95-7.75 (m, 2H), 7.18 (d; 1H), 7.52 (d, 1H), 7.21 (s, 1H), 2.26 (s, 3H), 2.17 (s, 3H).

EXAMPLE 15

2-(4-Methyl-imidazol-1-yl)-5-[1-(1-phenyl-ethyl)-1H-[1,2,4]triazol-3-ylamino]-benzonitrile

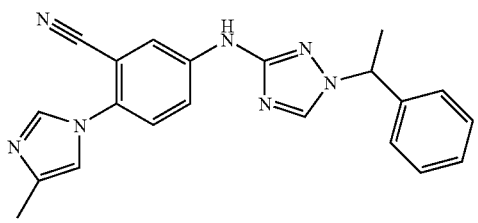

a) 1-(1-Phenyl-ethyl)-1H-[1,2,4]triazol-3-ylamine

Prepared in analogy to example 3a) starting with 3-amino-1,2,4-triazole and (1-bromoethyl)benzene. The title compound was obtained as a colorless solid (Yield=10%). MS ISP (m/e): 189.2.0 (100) [(M+H)$^+$].

$^1$H NMR (DMSO-D$_6$, 300 MHz): δ (ppm)=8.11 (s, 1H), 7.33 (t, 2H), 7.30-7.25 (m, 3H), 5.41 (qa, 1H), 5.23 (s, 2H), 1.72 (d, 3H).

b) 2-(4-Methyl-imidazol-1-yl)-5-[1-(1-phenyl-ethyl)-1H-[1,2,4]triazol-3-ylamino]-benzonitrile Prepared in analogy to example 1b) starting with 5-bromo-2-(4-methyl-imidazol-1-yl)-benzonitrile and 1-(1-phenyl-ethyl)-1H-[1,2,4]triazol-3-ylamine. The title compound was obtained as a yellowish solid (Yield=48%). MS ISP (m/e): 370.2 (100) [(M+H)$^+$].

$^1$H NMR (DMSO, 300 MHz): δ (ppm)=9.91 (s, 1H), 8.53 (s, 1H), 8.05 (s, 1H), 7.86 (s, 1H), 7.82 (d, 1H), 7.49 (d, 1H), 7.40-7.25 (m, 5H), 7.20 (s, 1H), 5.66 (qa, 1H), 2.17 (s, 3H), 1.83 (d, 3H).

EXAMPLE 16

5-[1-(4-Fluoro-benzyl)-1H-pyrazol-3-ylamino]-2-(4-methyl-imidazol-1-yl)-benzonitrile

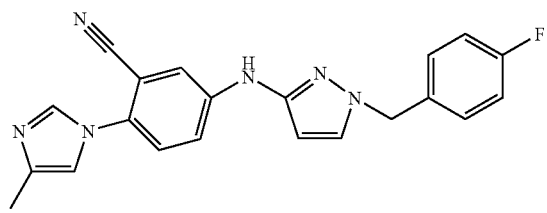

a) 1-(4-Fluoro-benzyl)-1H-pyrazol-3-ylamine

Prepared in analogy to example 10a) starting with 3-amino-1H-pyrazole and 4-fluorobenzylbromide. The title compound was obtained as a colorless solid (Yield=34%). MS ISP (m/e): 192.2 (100) [(M+H)$^+$].

b) 5-[1-(4-Fluoro-benzyl)-1H-pyrazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(4-fluoro-benzyl)-1H-pyrazol-3-ylamine. The title compound was obtained as a yellowish oil (Yield=75%). MS ISP (m/e): 373.2 (100) [(M+H)$^+$].

1H NMR (CDCl$_3$, 300 MHz): δ (ppm)=7.69 (d, 1H), 7.64 (d, 1H), 7.39-7.31 (m, 3H), 7.27-7.21 (m, 2H), 7.09-7.03 (m, 2H), 6.96 (s, 1H), 6.38 (s, 1H), 5.96 (d, 1H), 5.20 (s, 2H), 2.30 (s, 3H).

EXAMPLE 17

2-(4-Methyl-imidazol-1-yl)-5-[1-(3,4,5-trifluoro-benzyl)-1H-[1,2,4]triazol-3-ylamino]-benzonitrile

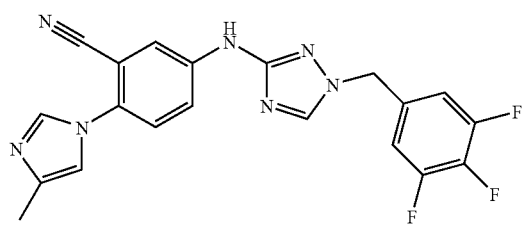

a) 1-(3,4,5-Trifluoro-benzyl)-1H-[1,2,4]triazol-3-ylamine

Prepared in analogy to example 3a) starting with 3-amino-1,2,4-triazole and 3,4,5-trifluorobenzyl bromide. A pure fraction of the title compound was obtained as a colorless solid (Yield=4%). MS ISP (m/e): 229.2 (100) [(M+H)$^+$].

$^1$H NMR (DMSO-D$_6$, 300 MHz): δ (ppm)=8.11 (s, 1H), 7.23 (t broad, 2H), 5.32 (s broad, 2H), 5.12 (s, 2H).

b) 2-(4-Methyl-imidazol-1-yl)-5-[1-(3,4,5-trifluoro-benzyl)-1H-[1,2,4]triazol-3-ylamino]-benzonitrile Prepared in analogy to example 1b) starting with 5-bromo-2-(4-methyl-imidazol-1-yl)-benzonitrile and 4-(3-amino-[1,2,4]triazol-1-ylmethyl)-benzonitrile. The title compound was obtained as a colorless solid (Yield=30%). MS ISP (m/e): 410.2 (100) [(M+H)$^+$].

¹H NMR (DMSO, 300 MHz): δ (ppm)=9.94 (s, 1H), 8.48 (s, 1H), 8.05 (s, 1H), 7.84 (s, 1H), 7.81 (d, 1H), 7.50 (d, 1H), 7.35 (t, 2H), 7.21 (s, 1H), 5.36 (s, 2H), 2.17 (s, 3H).

EXAMPLE 18

2-(4-Methyl-imidazol-1-yl)-5-(1-phenyl-1H-[1,2,4]triazol-3-ylamino)-benzonitrile

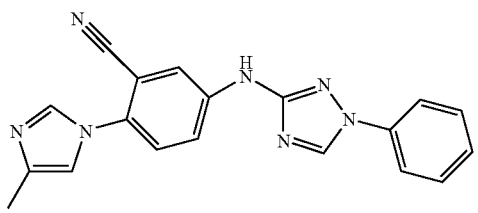

a) 1-Phenyl-1H-[1,2,4]triazol-3-ylamine

This compound was prepared from 5-phenyl-[1,2,4]oxadiazol-3-ylamine (Journal of Organic Chemistry 28, 1812 (1963) and aniline, via the rearrangement described by Ruccia et al., Journal of Heterocyclic Chemistry 8, 137 (1971). The title compound was isolated as a slightly brownish solid in a yield of 87%. MS ISP (m/e): 161.2 (100) [(M+H)⁺].

b) 2-(4-Methyl-imidazol-1-yl)-5-(1-phenyl-1H-[1,2,4]triazol-3-ylamino)-benzonitrile Prepared in analogy to example 1b) starting with 5-bromo-2-(4-methyl-imidazol-1-yl)-benzonitrile and 1-phenyl-1H-[1,2,4]triazol-3-ylamine. The title compound was obtained as a brownish solid (Yield=64%). MS ISP (m/e): 340.4 (100) [(M+H)⁺].

¹H NMR (DMSO, 300 MHz): δ (ppm)=10.19 (s, 1H), 9.17 (s, 1H), 8.13 (d, 1H), 7.98 (dxd, 1H), 7.90-7.80 (m, 3H), 7.65-7.55 (m, 3H), 7.39 (t, 1H), 7.24 (s, 1H), 2.19 (s, 3H).

EXAMPLE 19

2-(4-Methyl-imidazol-1-yl)-5-[1-(2-trifluoromethyl-phenyl)-1H-[1,2,4]triazol-3-ylamino]-benzonitrile

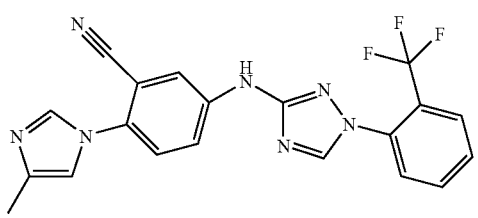

a) 1-(2-Trifluoromethyl-phenyl)-1H-[1,2,4]triazol-3-ylamine

Prepared in analogy to example 18a), starting with 5-phenyl-[1,2,4]oxadiazol-3-ylamine and 2-aminobenzotrifluoride. The title compound was obtained as brownish solid in a yield of 94%. MS ISP (m/e): 229.2 (64) [(M+H)⁺].

¹H NMR (DMSO, 300 MHz): δ (ppm)=8.28 (s, 1H), 7.93 (d, 1H), 7.84 (t, 1H), 7.72 (t, 1H), 7.63 (d, 1H), 5.57 (s, 2H).

b) 2-(4-Methyl-imidazol-1-yl)-5-[1-(2-trifluoromethyl-phenyl)-1H-[1,2,4]triazol-3-ylamino]-benzonitrile Prepared in analogy to example 1b) starting with 5-bromo-2-(4-methyl-imidazol-1-yl)-benzonitrile and 1-(2-trifluoromethyl-phenyl)-1H-[1,2,4]triazol-3-ylamine. The title compound was obtained as a brownish solid (Yield=77%). MS ISP (m/e): 410.2 (100) [(M+H)⁺].

¹H NMR (DMSO, 300 MHz): δ (ppm)=10.15 (s, 1H), 8.77 (s, 1H), 8.15 (d, 1H), 8.01 (d, 1H), 8.00-7.75 (m, 5H), 7.53 (d, 1H), 7.22 (s, 1H), 2.17 (s, 3H).

EXAMPLE 20

5-[5-(2,6-Dichloro-benzyl)[1,2,4]oxadiazol-3-ylamino]-2-(4-methyl-imidazol-1-yl)-benzonitrile

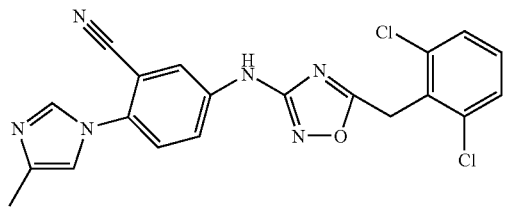

Prepared in analogy to example 1b) starting with 5-bromo-2-(4-methyl-imidazol-1-yl)-benzonitrile and 5-(2,6-dichloro-benzyl)-[1,2,4]oxadiazol-3-ylamine (M. J. Dimsdale, J. Heterocyclic Chem. 1981, 18, 37-41). The title compound was obtained as a white solid (Yield=17%). MS ISP (m/e): 425.1 & 426.9 (100 & 84) [(M+H)⁺].

¹H NMR (CDCl₃, 300 MHz): δ (ppm)=7.87-7.86 (m, 1H), 7.69 (m, 1H), 7.66-7.62 (m, 1H), 7.42-7.24 (m, 4H), 7.00 (bs, 1H), 6.94 (bs, 1H), 4.55 (s, 2H), 2.31 (s, 3H).

EXAMPLE 21

5-(1-Benzyl-1H-pyrazol-4-ylamino)-2-(4-methyl-imidazol-1-yl)-benzonitrile

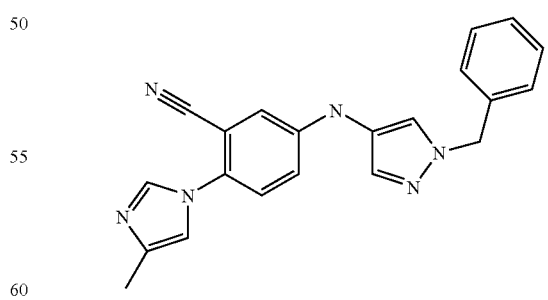

a) 1-Benzyl-4-nitro-1H-pyrazole

To a solution of 4-nitro-1H-pyrazole (283 mg, 2.5 mmol) in dry DMF (5 ml) under an argon atmosphere was added NaH (120 mg, 2.75 mmol) in small portions at 0° C. The reaction mixture was stirred at rt for 1 hour, cooled again to 0° C. before benzyl bromide (300 µl, 2.5 mmol) was added and stirred at rt for 12 h. The mixture was diluted with water, extracted with ethyl acetate and the product was purified by chromatography on silica gel using heptane/ethyl acetate as eluent. The title compound was obtained as light yellow oil (484 mg, 95%). MS ISP (m/e): 226.3 (100) [(M+Na)$^+$].

b) 1-Benzyl-1H-pyrazol-4-ylamine

A mixture of 1-benzyl-4-nitro-1H-pyrazole (33 mg, 0.162 mmol) and 10% Pd/C (10 mg) was stirred under an hydrogen atmosphere at rt for 12 h. The catalyst was filtered off, washed with methanol and the solvent was removed under reduced pressure to give the title compound as dark brown oil (27.4 mg, 97%). MS ISP (m/e): 174.2.3 (100) [(M+H)$^+$].

c) 5-(1-Benzyl-1H-pyrazol-4-ylamino)-2-(4-methyl-imidazol-1-yl)-benzonitrile

Prepared in analogy to example 1b) starting with 5-bromo-2-(4-methyl-imidazol-1-yl)-benzonitrile and 1-benzyl-1H-pyrazol-4-ylamine. The title compound was obtained as a yellow oil (Yield=40%). MS ISP (m/e): 355.2 (100) [(M+H)$^+$].

$^1$H NMR (CDCl$_3$, 300 MHz): δ (ppm)=7.60-7.59 (m, 1H), 7.49 (m, 1H), 7.42-7.34 (m, 4H), 7.29-7.26 (m, 1H), 7.18-7.15 (m, 2H), 6.99-6.92 (m, 3H), 5.37 (bs, 1H), 5.31 (s, 2H), 2.29 (m, 3H)

EXAMPLE 22

5-(1-Benzyl-1H-[1,2,4]triazol-3-ylamino)-2-(4-methyl-imidazol-1-yl)-benzonitrile

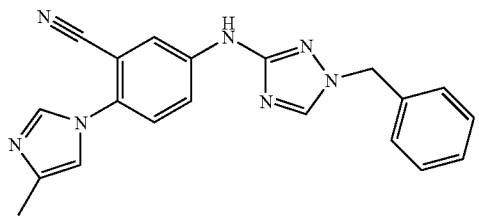

a) 1-Benzyl-1H-[1,2,4]triazol-3-ylamine

Prepared in analogy to example 3a) starting with 3-amino-1,2,4-triazole and benzyl bromide. The title compound was obtained as a colorless solid (Yield=14%). MS ISP (m/e): 175.3 (100) [(M+H)$^+$].

$^1$H NMR (DMSO, 300 MHz): δ (ppm)=5.11 (s, 2H), 5.23 (s, 2H), 7.35-7.25 (m, 5H), 8.10 (s, 1H).

b) 5-(1-Benzyl-1H-[1,2,4]triazol-3-ylamino)-2-(4-methyl-imidazol-1-yl)-benzonitrile Prepared in analogy to example 1b) starting with 5-bromo-2-(4-methyl-imidazol-1-yl)-benzonitrile and 1-benzyl-1H-[1,2,4]triazol-3-ylamine. The title compound was obtained as a white solid (Yield=25%). MS ISP (m/e): 356.1 (100) [(M+H)$^+$].

$^1$H NMR (DMSO, 300 MHz): δ (ppm)=9.91 (s, 1H), 8.51 (s, 1H), 8.04 (s, 1H), 7.85-7.80 (m, 2H), 7.50 (d, 1H), 7.40-7.30 (m, 5H), 7.20 (s, 1H), 5.35 (s, 2H), 2.17 (s, 3H).

EXAMPLE 23

5-[1-(4-Chloro-phenyl)-1H-[1,2,4]triazol-3-ylamino]-2-(4-methyl-imidazol-1-yl)-benzonitrile

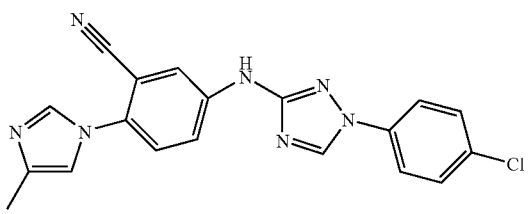

a) 1-(4-Chloro-phenyl)-1H-[1,2,4]triazol-3-ylamine

Prepared in analogy to example 18a), starting with 5-phenyl-[1,2,4]oxadiazol-3-ylamine and 4-chloroaniline. The title compound was obtained as brownish solid (Yield=54%). MS ISP (m/e): 195.1 (100) [(M+H)$^+$].

$^1$H NMR (DMSO, 300 MHz): δ (ppm)=9.00 (s, 1H), 7.75 (d, 2H), 7.56 (d, 2H), 5.20 (s broad, 2H).

b) 5-[1-(4-Chloro-phenyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(4-chloro-phenyl)-1H-[1,2,4]triazol-3-ylamine. The title compound was obtained as a colorless solid (Yield=18%). MS ISP (m/e): 376.2 (100) & 378.2 (35) [(M+H)$^+$].

$^1$H NMR (DMSO, 300 MHz): (ppm)=10.20 (s, 1H), 9.19 (s, 1H), 8.10 (d, 1H), 7.98 (dxd, 1H), 7.95-7.85 (m, 3H), 7.65 (d, 2H), 7.57 (d, 2H), 7.24 (s, 1H), 2.18 (s, 3H).

EXAMPLE 24

5-[1-(2,4-Dichloro-benzyl)-1H-[1,2,4]triazol-3-ylamino]-2-(4-methyl-imidazol-1-yl)-benzonitrile

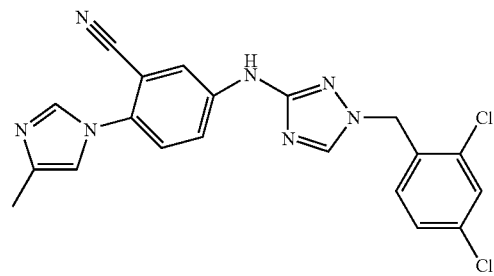

Prepared in analogy to example 1b) starting with 5-bromo-2-(4-methyl-imidazol-1-yl)-benzonitrile and 1-(2,4-dichloro-benzyl)-1H-[1,2,4]triazol-3-ylamine (ART-CHEM). The title compound was obtained as a colorless solid (Yield=67%). MS ISP (m/e): 424.1 (100) & 426.0 (81) [(M+H)$^+$].

$^1$H NMR (DMSO, 300 MHz): δ (ppm)=9.95 (s, 1H), 8.51 (s, 1H), 8.06 (d, 1H), 7.83 (d, 1H), 7.78 (dxd, 1H), 7.70 (d, 1H), 7.50-7.45 (m, 2H), 7.33 (d, 1H), 7.20 (s, 1H), 5.45 (s, 2H), 2.17 (s, 3H).

EXAMPLE 25

2-(4-Methyl-imidazol-1-yl)-5-[1-(3-trifluoromethyl-benzyl)-1H-[1,2,4]triazol-3-ylamino]-benzonitrile

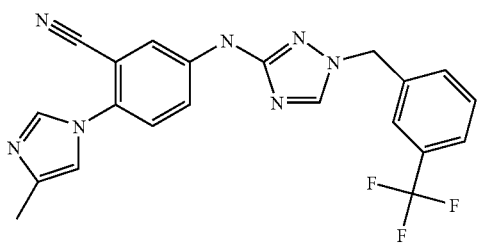

Prepared in analogy to example 1b) starting with 5-bromo-2-(4-methyl-imidazol-1-yl)-benzonitrile and 1-(3-trifluoromethyl-benzyl)-1H-[1,2,4]triazol-3-ylamine. The title compound was obtained as a white solid (Yield=51%). MS ISP (m/e): 424.2 (100) [(M+H)$^+$].

$^1$H NMR (CDCl$_3$, 300 MHz): δ (ppm)=8.06-8.05 (m, 1H), 7.91 (m, 1H), 7.67-7.50 (m, 6H), 7.31-7.28 (m, 1H), 7.07 (m, 1H), 6.99 (s, 1H), 5.34 (s, 2H), 2.31 (m, 3H).

EXAMPLE 26

5-[1-(4-Methyl-benzyl)-1H-[1,2,4]triazol-3-ylamino]-2-(4-methyl-imidazol-1-yl)-benzonitrile

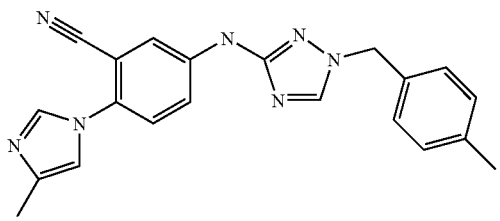

Prepared in analogy to example 1b) starting with 5-bromo-2-(4-methyl-imidazol-1-yl)-benzonitrile and 1-(4-methyl-benzyl)-1H-[1,2,4]triazol-3-ylamine. The title compound was obtained as a white solid (Yield=50%). MS ISP (m/e): 370.1 (100) [(M+H)$^+$].

$^1$H NMR (CDCl$_3$, 300 MHz): δ (ppm)=8.08-8.07 (m, 1H), 7.79 (m, 1H), 7.66 (m, 1H), 7.61-7.58 (m, 1H), 7.30-7.23 (m, 5H), 7.02 (m, 1H), 6.99 (s, 1H), 5.22 (s, 2H), 2.37 (s, 3H), 2.31 (s, 3H).

EXAMPLE 27

2-(4-Methyl-imidazol-1-yl)-5-[1-(3,4,5-trifluoro-benzyl)-1H-pyrazol-3-ylamino]-benzonitrile

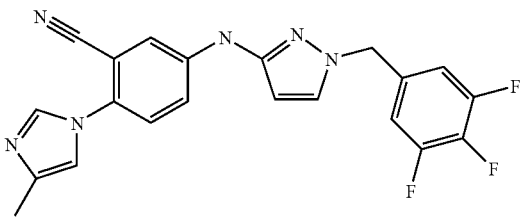

a) 1-(3,4,5-Trifluoro-benzyl)-1H-pyrazol-3-ylamine

Prepared in analogy to example 10a) starting with 3-amino-1H-pyrazole and 3,4,5-trifluorobenzyl bromide. The title compound was obtained as a brown oil (Yield=31%). MS ISP (m/e): 228.2 (100) [(M+H)$^+$].

b) 2-(4-Methyl-imidazol-1-yl)-5-[1-(3,4,5-trifluoro-benzyl)-1H-pyrazol-3-ylamino]-benzonitrile Prepared in analogy to example 1b) starting with 5-bromo-2-(4-methyl-imidazol-1-yl)-benzonitrile and 1-(3,4,5-trifluoro-benzyl)-1H-pyrazol-3-ylamine. The title compound was obtained as a white solid (Yield=56%). MS ISP (m/e): 409.3 (100) [(M+H)$^+$].

$^1$H NMR (CDCl$_3$, 300 MHz): δ (ppm)=7.71-7.70 (m, 1H), 7.64 (m, 1H), 7.42-7.37 (m, 2H), 7.23 (m, 1H), 6.97-6.96 (m, 1H), 6.88-6.80 (m, 2H), 6.25 (bs, 1H), 6.01-6.00 (m, 1H), 5.17 (s, 2H), 2.31 (m, 3H).

EXAMPLE 28

5-(3-Benzyl-[1,2,4]thiadiazol-5-ylamino)-2-(4-methyl-imidazol-1-yl)-benzonitrile

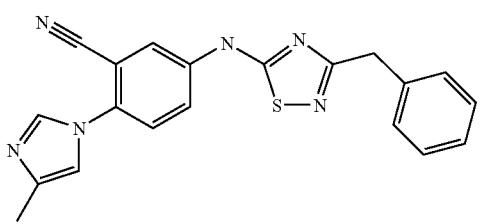

a) 3-Benzyl-5-chloro-[1,2,4]thiadiazole

To a suspension of 2-phenyl-acetamidine hydrochloride (1.078 g, 6 mmol) in dichloromethane (10 ml) was added perchloromethyl mercaptan (0.61 ml, 5 mmol) via syringe. The mixture was cooled in an ice-methanol bath to −10° C. and a solution of sodium hydroxide (1.2 g, 30 mmol) in water (3 ml) was added dropwise keeping the temperature below −8° C. After complete addition the mixture was stirred 10 min at 0° C. The reaction mixture was diluted with water and the aqueous phase was extracted three times with dichloromethane. The combined organic phases were dried over Na$_2$SO$_4$, filtered and the solvents were evaporated. The residue was purified by chromatography on silica gel using heptane/ethyl acetate as eluent. The title compound was obtained as an orange liquid (0.779 g, 62%). MS ISP (m/e): 211.0 (100) [(M+H)$^+$].

b) 3-Benzyl-[1,2,4]thiadiazol-5-ylamine

A mixture of 3-benzyl-5-chloro-[1,2,4]thiadiazole (105 mg, 0.5 mmol) in ammonia (2 N in MeOH, 2 ml) was heated in a pressure tube at 50° C. for 5 h. The solvents were evaporated, the residue diluted with dichloromethane, the white solid (ammonium chloride) was filtered off, the filtrate was concentrated and then purified by silica gel chromatography using dichloromethane/methanol as eluent. The title compound was obtained as a light yellow liquid (40 mg, 41%). MS ISP (m/e): 192.1 (100) [(M+H)$^+$].

c) 5-(3-Benzyl-[1,2,4]thiadiazol-5-ylamino)-2-(4-methyl-imidazol-1-yl)-benzonitrile Prepared in analogy to example 1b) starting with 5-bromo-2-(4-methyl-imidazol-1-yl)-benzonitrile and 3-benzyl-[1,2,4]thiadiazol-5-ylamine. The title compound was obtained as a white solid (Yield=21%). MS ISP (m/e): 373.1 (100) [(M+H)$^+$].

$^1$H NMR (CDCl$_3$, 300 MHz): δ (ppm)=8.47 (m, 1H), 7.98-7.97 (m, 1H), 7.73-7.72 (m, 1H), 7.68-7.64 (m, 1H), 7.42-7.23 (m, 6H), 7.04 (m, 1H), 4.17 (s, 2H), 2.32 (m, 3H).

EXAMPLE 29

5-[1-(3-Chloro-benzyl)-1H-pyrazol-3-ylamino]-2-(4-methyl-imidazol-1-yl)-benzonitrile

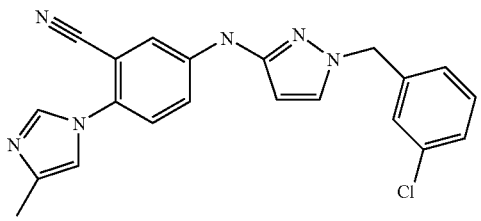

a) 1-(3-Chloro-benzyl)-1H-pyrazol-3-ylamine

Prepared in analogy to example 10a) starting with 3-amino-1H-pyrazole and 3-chlorobenzyl bromide. The title compound was obtained as a brown oil (Yield=11%). MS ISP (m/e): 208.0 (100) [(M+H)$^+$].

b) 5-[1-(3-Chloro-benzyl)-1H-pyrazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(3-chlorobenzyl)-1H-pyrazol-3-ylamine. The title compound was obtained as a light yellow solid (Yield=56%). MS ISP (m/e): 389.2 (100) [(M+H)$^+$].

$^1$H NMR (CDCl$_3$, 300 MHz): δ (ppm)=7.67-7.66 (m, 1H), 7.64-7.63 (m, 1H), 7.40-7.22 (m, 6H), 7.16-7.12 (m, 1H), 6.97-6.96 (m, 1H), 6.23 (bs, 1H), 5.99-5.98 (m, 1H), 5.21 (s, 2H), 2.30 (m, 3H).

EXAMPLE 30

5-[1-(2,4-Dichloro-benzyl)-1H-pyrazol-3-ylamino]-2-(4-methyl-imidazol-1-yl)-benzonitrile

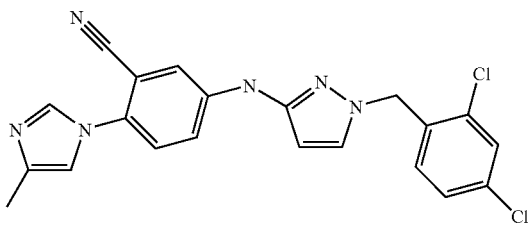

a) 1-(2,4-Dichloro-benzyl)-1H-pyrazol-3-ylamine

Prepared in analogy to example 10a) starting with 3-amino-1H-pyrazole and 2,4-dichlorobenzyl bromide. The title compound was obtained as a light yellow solid (Yield=52%). MS ISP (m/e): 242.2 (100) [(M+H)$^+$].

b) 5-[1-(2,4-Dichloro-benzyl)-1H-pyrazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(2,4-dichloro-benzyl)-1H-pyrazol-3-ylamine. The title compound was obtained as a light yellow solid (Yield=72%). MS ISP (m/e): 423.1 (100) [(M+H)$^+$].

$^1$H NMR (CDCl$_3$, 300 MHz): δ (ppm)=7.72-7.71 (m, 1H), 7.64-7.63 (m, 1H), 7.44 (m, 1H), 7.40-7.36 (m, 2H), 7.27-7.22 (m, 2H), 7.07-7.04 (m, 1H), 6.97-6.96 (m, 1H), 6.25 (bs, 1H), 5.98-5.97 (m, 1H), 5.31 (s, 2H), 2.30 (m, 3H).

EXAMPLE 31

[5-(4-Chloro-phenyl)-[1,3,4]oxadiazol-2-yl]-[3-methoxy-4-(4-methyl-imidazol-1-yl)-phenyl]-amine

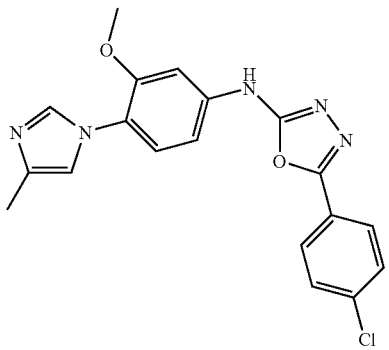

a) 1-(2-Methoxy-4-nitro-phenyl)-4-methyl-1H-imidazole

A solution of 2-chloro-5-nitroanisole (187 mg, 1 mmol), of 4-methyl-1H-imidazole (335 mg, 4 mmol) and of potassium hydroxide (99 mg, 1.5 mmol) in DMSO (0.86 mL) was stirred for 5 h at 80° C. under an atmosphere of nitrogen. After cooling to 20° C. the reaction was poured onto ice-water. A precipitation was formed and the suspension was stirred for 15 min. The solid was filtered off, washed with water, dissolved in dichloromethane, dried over sodium sulfate, filtered and the solvent was evaporated under reduced pressure to yield a yellow solid. The crude product was purified on silica gel using dichloromethane/methanol (19:1 v/v) as eluent to yield the title compound (106 mg, 45%) as a pale-yellow solid. Alternatively the product can be also crystallized from the crude material from diethyl ether.

MS ISP (m/e): 234.3 (100) [(M+H)$^+$].

$^1$H NMR (CDCl$_3$, 300 MHz): δ (ppm)=7.97 (d, 1H), 7.96 (s, 1H), 7.83 (s, 1H), 7.42 (d, 1H), 7.00 (s, 1H), 4.00 (s, 3H), 2.31 (s, 3H).

b) 3-Methoxy-4-(4-methyl-imidazol-1-yl)-phenylamine 1-(2-Methoxy-4-nitro-phenyl)-4-methyl-1H-imidazole (2.52 g, 10.8 mmol) dissolved in ethanol (110 mL) was stirred under an atmosphere of hydrogen at 20° C. for 3.5 h in the presence of 10% palladium on charcoal (0.25 g). The catalyst was filtered off and washed with ethanol. The solvent of the filtrate was evaporated under reduced pressure. The crude product was purified on silica gel using dichloromethane/methanol (19:1 v/v) as eluent. The fraction containing the product was suspended in diethyl ether, stirred for 15 min, filtered and dried to yield the title compound (1.72 g, 78%) as a yellow solid.

MS ISP (m/e): 204.3 (100) [(M+H)$^+$].

$^1$H NMR (CDCl$_3$, 300 MHz): δ (ppm)=7.48 (s, 1H), 6.91 (d, 1H), 6.88 (s, 1H), 6.35 (s, 1H), 6.17 (d, 1H), 3.68 (s, 3H), 2.11 (s, 3H).

c) 1,3-Bis-[3-methoxy-4-(4-methyl-imidazol-1-yl)-phenyl]-thiourea

A suspension of 3-methoxy-4-(4-methyl-imidazol-1-yl)-phenylamine (0.5 g, 2.46 mmol) in 5 ml ethanol was treated with triethylamine (0.37 ml, 2.46 mmol) and carbon disulfide (1.87 g, 24.6 mmol). The mixture was cooled in an ice-bath and a solution of di-tert-butyl dicarbonate (0.53 g, 2.44 mmol) in 1 ml ethanol slowly added, followed by 5 mg of 4-dimethylaminpyridine. After about 2 hours, gas evolution ceased and the reaction mixture was concentrated in vacuo and diluted with diethyl ether. The resulting precipitate was filtered and dried to yield the title compound as a brownish solid (0.418 g, 38%). MS ISP (m/e): 449.1 (45) [(M+H)$^+$].

d) [5-(4-Chloro-phenyl)-[1,3,4]oxadiazol-2-yl]-[3-methoxy-4-4-methyl-imidazol-1-yl)-phenyl]-amine A solution of mercury-(II)-oxide (97 mg, 0.45 mmol) in 5 ml of methanol was treated with 1,3-bis-[3-methoxy-4-(4-methyl-imidazol-1-yl)-phenyl]-thiourea (200 mg, 0.45 mmol) and 4-chloro-benzhydrazide (76 mg, 0.45 mmol). The resulting mixture was refluxed for 3 hours, concentrated and triturated with ethyl acetate. Filtering of the suspension and chromatography on silica gel using ethyl acetate as eluent gave the title compound as a brownish solid (14 mg, 8%) MS ISP (m/e): 382.3 (100) & 384.1 (37) [(M+H)$^+$]. .

$^1$H NMR (CDCl$_3$, 300 MHz): δ (ppm)=9.87 (s broad, 1H), 7.90 (d, 2H), 7.70 (d, 1H); 7.63 (s, 1H), 7.48 (d, 2H), 7.19 (d, 1H), 7.10 (dxd, 1H), 6.88 (s, 1H), 3.90 (s, 3H), 2.28 (s, 3H).

EXAMPLE 32

5-[1-(2-Chloro-phenyl)-1H-[1,2,4]triazol-3-ylamino]-2-(4-methyl-imidazol-1-yl)-benzonitrile

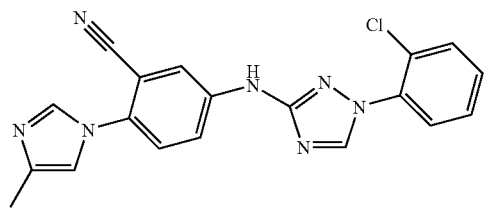

a) 1-(2-Chloro-phenyl)-1H-[1,2,4]triazol-3-ylamine

Prepared in analogy to example 18a), starting with 5-phenyl-[1,2,4]oxadiazol-3-ylamine and 2-chloroaniline. The title compound was obtained as brownish solid (Yield=61%). MS ISP (m/e): 195.1 (100) [(M+H)$^+$].

$^1$H NMR (CDCl$_3$, 300 MHz): δ (ppm)=8.22 (s, 1H), 7.65-7.35 (m, 4H), 4.22 (s broad, 2H).

b) 5-[1-(2-Chloro-phenyl)-1H-[1,2,4]triazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(2-chloro-phenyl)-1H-[1,2,4]triazol-3-ylamine. The title compound was obtained as a colorless solid (Yield=27%). MS ISP (m/e): 374.3 (100) [(M+H)$^+$].

$^1$H NMR (CDCl$_3$, 300 MHz): δ (ppm)=9.61 (s broad, 1H), 8.40 (s, 1H), 8.28 (d, 1H), 7.92 (dxd, 1H), 7.75-7.65 (m, 2H), 7.59 (d, 1H), 7.55-7.40 (m, 2H), 7.30 (d, 1H), 6.99 (s, 1H), 2.30 (s, 3H).

EXAMPLE 33

(5-Benzyl-[1,3,4]oxadiazol-2-yl)-[3-methoxy-4-(4-methyl-imidazol-1-yl)-phenyl]-amine

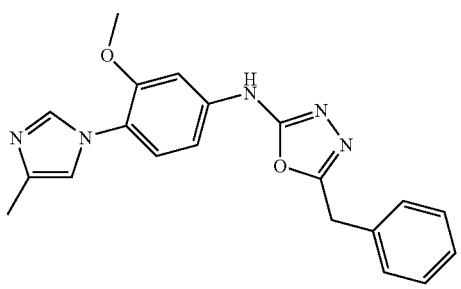

Prepared in analogy to example 31d) from 1,3-bis-[3-methoxy-4-(4-methyl-imidazol-1-yl)-phenyl]-thiourea and phenylacetic hydrazide (Yield=7%). MS ISP (m/e): 362.3 (100) [(M+H)$^+$].

¹H NMR (CDCl₃, 300 MHz): δ (ppm)=9.25 (s broad, 1H), 7.58 (d, 2H), 7.40-7.20 (m, 5H), 7.13 (d, 1H), 6.99 (dxd, 1H), 6.85 (s, 1H), 4.14 (s, 2H), 3.84 (s, 3H), 2.28 (s, 3H).

EXAMPLE 34

3-{3-[3-Cyano-4-(4-methyl-imidazol-1-yl)-phenylamino]-[1,2,4]triazol-1-ylmethyl}-benzoic acid methyl ester

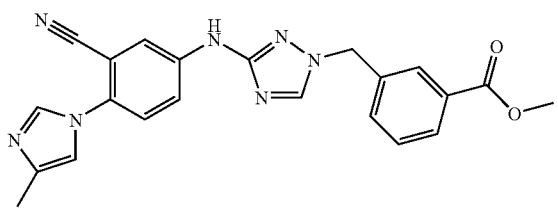

a) 3-(3-Amino-[1,2,4]triazol-1-ylmethyl)-benzoic acid methyl ester

Prepared in analogy to example 3a) starting with 3-amino-1,2,4-triazole and methyl-3-(bromomethyl)benzoate. The title compound was obtained as a colorless solid (Yield=8%). MS ISP (m/e): 233.1 (100) [(M+H)⁺].

¹H NMR (CDCl₃, 300 MHz): δ (ppm)=8.02 (t, 1H), 7.95 (s, 1H), 7.45 (d, 1H), 5.17 (s, 2H), 4.21 (s broad, 2H), 3.92 (s, 3H).

b) 3-{3-[3-Cyano-4-(4-methyl-imidazol-1-yl)-phenylamino]-[1,2,4]triazol-1-ylmethyl}-benzoic acid methyl ester Prepared in analogy to example 1b) starting with 5-bromo-2-(4-methyl-imidazol-1-yl)-benzonitrile and 3-(3-amino-[1,2,4]triazol-1-ylmethyl)-benzoic acid methyl ester. The title compound was obtained as a colorless solid (Yield=40%). MS ISP (m/e): 414.3 (100) [(M+H)⁺].

¹H NMR (CDCl₃, 300 MHz): δ (ppm)=8.10-8.00 (m, 3H), 7.88 (s, 1H), 7.68 (s, 1H), 7.60 (dxd, 1H), 7.60-7.45 (m, 2H), 7.30 (d, 1H), 7.12 (s, 1H), 6.99 (s, 1H), 5.32 (s, 2H), 3.93 (s, 3H), 2.31 (s, 3H).

EXAMPLE 35

5-{1-[3-(1-Hydroxy-1-methyl-ethyl)-benzyl]-1H-[1,2,4]triazol-3-ylamino}-2-(4-methyl-imidazol-1-yl)-benzonitrile

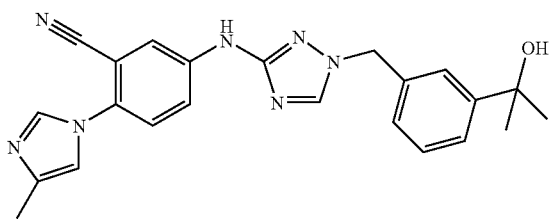

A suspension of 3-{3-[3-cyano-4-(4-methyl-imidazol-1-yl)-phenylamino]-[1,2,4]triazol-1-ylmethyl}-benzoic acid methyl ester (65 mg, 0.16 mmol) in 4 ml of THF was cooled in an ice-bath and treated with 0.32 ml (0.98 mmol) of a 3 molar solution of methylmagnesium chloride in THF. The reaction mixture was allowed to slowly warm up and stirred for 2 hours at room temperature. Hydrolysis and extraction with ethyl acetate gave the crude product which was purified by trituration in diethyl ether to give the title compound as a colorless solid (35 mg; Yield=54%). MS ISP (m/e): 414.4 (100) [(M+H)⁺].

¹H NMR (CDCl₃, 300 MHz): δ (ppm)=8.08 (d, 1H), 7.83 (s, 1H), 7.65 (s, 1H), 7.60-7.50 (m, 3H), 7.47 (d, 1H), 7.38 (t, 1H), 7.35-7.15 (m, 3H), 6.98 (s, 1H), 5.27 (s, 2H), 2.31 (s, 3H), 1.59 (s, 6H).

EXAMPLE 36

5-[1-(4-Chloro-benzyl)-1H-pyrazol-3-ylamino]-2-(4-methyl-imidazol-1-yl)-benzonitrile

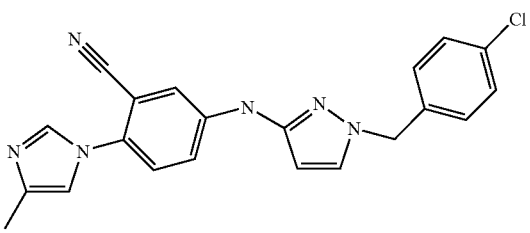

a) 1-(4-Chloro-benzyl)-1H-pyrazol-3-ylamine

Prepared in analogy to example 10a) starting with 3-amino-1H-pyrazole and 2,4-dichlorobenzyl bromide. The title compound was obtained as a light yellow solid (Yield=29%).

MS ISP (m/e): 208.0 (100) [(M+H)⁺].

b) 5-[1-(4-Chloro-benzyl)-1H-pyrazol-3-ylamino]-2-(4-methyl-imidazol-1-yl)-benzonitrile Prepared in analogy to example 1b) starting with 5-bromo-2-(4-methyl-imidazol-1-yl)-benzonitrile and 1-(4-chlorobenzyl)-1H-pyrazol-3-yl amine. The title compound was obtained as a light yellow solid (Yield=28%). MS ISP (m/e): 389.2 (100) [(M+H)⁺].

¹H NMR (CDCl₃, 300 MHz): δ (ppm)=7.68-7.67 (m, 1H), 7.64-7.63 (m, 1H), 7.39-7.17 (m, 7H), 6.97-6.96 (m, 1H), 6.20 (bs, 1H), 5.98-5.97 (m, 1H), 5.20 (s, 2H), 2.30 (m, 3H).

EXAMPLE 37

2-[3-Methoxy-4-(4-methyl-imidazol-1-yl)-phenylamino]-thiazole-4-carboxylic acid ethyl ester

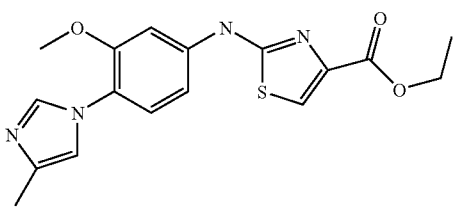

a) [3-Methoxy-4-(4-methyl-imidazol-1-yl)-phenyl]-thiourea

To a solution of 3-methoxy-4-(4-methyl-imidazol-1-yl)-phenylamine (500 mg, 2.46 mmol) in THF (30 ml) at 0° C. was slowly added benzoyl isothiocyanate (0.366 ml, 2.583 mmol) and the reaction mixture was stirred at rt for 2 hours. The solvents were evaporated and the residue was dissolved in methanol (50 ml). A solution of potassium carbonate (1.02 g, 7.38 mmol) in water (23 ml) was added dropwise at rt, the reaction mixture was stirred for 3 h at rt. The methanol was evaporated, water (10 ml) was added and stirred at rt for 1 hour. The solids were filtered off, washed with diethyl ether and dried in vacuo. After trituration with diethyl ether the title compound was obtained as light yellow solid (490 mg, 76%). MS ISP (m/e): 263.1 (100) [(M+H)$^+$].

b) 2-[3-Methoxy-4-(4-methyl-imidazol-1-yl)-phenylamino]-thiazole-4-carboxylic acid ethyl ester A suspension of [3-methoxy-4-(4-methyl-imidazol-1-yl)-phenyl]-thiourea (131 mg, 0.50 mmol) and ethyl bromopyruvate (74 μl, 0.50 mmol) in EtOH (3 ml) was stirred at 60° C. for 18 hours. The solid was filtered off and washed with cold EtOH, then dried in vacuo to give the title compound as light brown solid (130 mg, 72%). MS ISP (m/e): 359.1 (100) [(M+H)$^+$].
$^1$H NMR ((CD$_3$)$_2$CO, 300 MHz): δ (ppm)=10.85 (s, 1H), 9.29 (m, 1H), 7.98 (m, 1H), 7.89 (s, 1H), 7.68 (m, 1H), 7.53-7.50 (m, 1H), 7.28-7.24 (m, 1H), 4.27 (q, 2H), 3.87 (s, 3H), 2.34 (m, 3H), 1.30 (t, 3H).

EXAMPLE 38

2-{2-[3-Methoxy-4-(4-methyl-imidazol-1-yl)-phenylamino]-thiazol-4-yl}-propan-2-ol

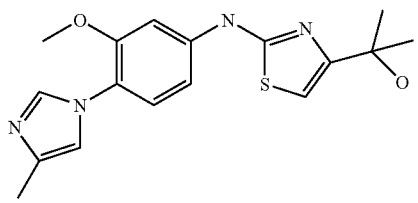

To a solution of 2-[3-methoxy-4-(4-methyl-imidazol-1-yl)-phenylamino]-thiazole-4-carboxylic acid ethyl ester (20 mg, 0.056 mmol) in dry THF (2 ml) at 0° C. was added methylmagnesium bromide (3M solution in THF, 93 μl, 0.279 mmol) added and stirred at 0° C. for 2 h. The reaction mixture was cautiously quenched with saturated aqueous ammonium chloride solution. The aqueous phase was extracted three times with diethyl ether, dried over Na$_2$SO$_4$, filtered and the solvents were evaporated. The residue was purified by silica gel chromatography using dichloromethane/methanol as eluent. The title compound was obtained as a light brown oil (14.4 mg, 75%). MS ISP (m/e): 345.1 (100) [(M+H)$^+$].

$^1$H NMR (CDCl$_3$, 300 MHz): δ (ppm)=8.21 (bs, 1H), 7.65 (m, 1H), 7.46 (m, 1H), 7.19-7.16 (m, 1H), 6.93-6.88 (m, 2H), 6.48 (s, 1H), 3.85 (s, 3H), 2.7 (bs, 1H), 2.30 (m, 3H), 1.61 (s, 6H).

EXAMPLE 39

5-[3-Cyano-4-(4-methyl-imidazol-1-yl)-phenylamino]-2-(3,4,5-trifluoro-benzyl)-2H-pyrazole-3-carboxylic acid methyl ester

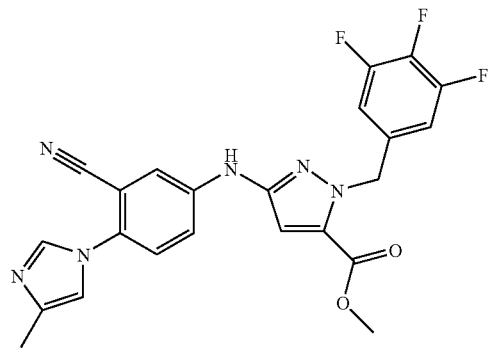

a) 5-Nitro-2-(3,4,5-trifluoro-benzyl)-2H-pyrazole-3-carboxylic acid methyl ester A mixture of methyl-3-nitro-1-H-pyrazole-5-carboxylate (ART-CHEM) (600 mg, 3.5 mmol), 3,4,5-trifluoromethyl-benzyl bromide (789 mg, 3.5 mmol) and cesium carbonate (1.37 g, 4.2 mmol) in 15 ml of acetonitrile was stirred at 60° C. for 2 hours. The reaction mixture was concentrated, hydrolysed and extracted with ethyl acetate. The organic phase was dried, evaporated and the residue triturated with diethyl ether to yield the title compound as a colorless solid (698 mg, Yield=63%). MS ISP (m/e): 333.1 (100) [(M+NH4)$^+$].
$^1$H NMR (CDCl$_3$, 300 MHz): δ (ppm)=7.43 (s, 1H), 7.04 (t, 2H), 5.75 (s, 2H), 3.95 (s, 3H).

b) 5-Amino-2-(3,4,5-trifluoro-benzyl)-2H-pyrazole-3-carboxylic acid methyl ester To a suspension of 5-nitro-2-(3,4,5-trifluoro-benzyl)-2H-pyrazole-3-carboxylic acid methyl ester (649 mg, 2.1 mmol) in 12 ml of methanol was added 100 mg of palladium 10% on charcoal and the mixture hydrogenated for 1.5 hours at room temperature and normal pressure. The catalyst was filtered off and the filtrate concentrated to yield the title compound as a colorless solid (47 mg, Yield=80%). MS ISP (m/e): 286.0 (100) [(M+H)$^+$].
$^1$H NMR (CDCl$_3$, 300 MHz): δ (ppm)=6.87 (t, 2H), 6.20 (s, 1H), 5.48 (s, 2H), 3.84 (s, 3H).

c) 5-[3-Cyano-4-(4-methyl-imidazol-1-yl)-phenylamino]-2-(3,4,5-trifluoro-benzyl)-2H-pyrazole-3-carboxylic acid methyl ester Prepared in analogy to example 1b) starting with 5-bromo-2-(4-methyl-imidazol-1-yl)-benzonitrile and 5-amino-2-(3,4,5-trifluoro-benzyl)-2H-pyrazole-3-carboxylic acid methyl ester. The title compound was obtained as a colorless solid (Yield=15%). MS ISP (m/e): 467.2 (100) [(M+H)$^+$].

¹H NMR (DMSO, 300 MHz): δ (ppm)=9.42 (s, 1H), 7.83 (d, 2H), 7.63 (dxd, 1H), 7.46 (d, 1H), 7.20 (s, 1H), 7.13 (t, 2H), 6.52 (s, 1H), 5.65 (s, 2H), 3.84 (s, 3H), 2.17 (s, 3H).

EXAMPLE 40

5-[5-(1-Hydroxy-1-methyl-ethyl)-1-(3,4,5-trifluoro-benzyl)-1H-pyrazol-3-ylamino]-2-(4-methyl-imidazol-1-yl)-benzonitrile

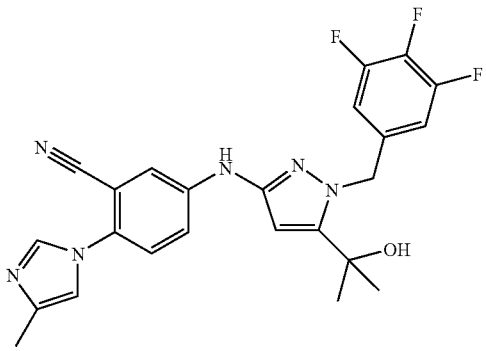

Prepared in analogy to example 35 from 5-[3-cyano-4-(4-methyl-imidazol-1-yl)-phenylamino]-2-(3,4,5-trifluoro-benzyl)-2H-pyrazole-3-carboxylic acid methyl ester and methyl magnesium chloride. The title compound was obtained as yellowish gum (Yield=27%). MS ISP (m/e): 467.2 (100).

¹H NMR (CDCl₃, 300 MHz): δ (ppm)=7.63 (d, 1H), 7.45-7.35 (m, 2H), 7.18 (d, 1H), 6.93 (s, 1H), 6.85 (t, 2H), 6.39 (s, 1H), 5.80 (s, 1H), 5.52 (s, 2H), 2.29 (s, 3H), 1.51 (s, 6H).

EXAMPLE 41

2-[3-Methoxy-4-(4-methyl-imidazol-1-yl)-phenylamino]-thiazole-4-carboxylic acid 4-fluoro-benzylamide

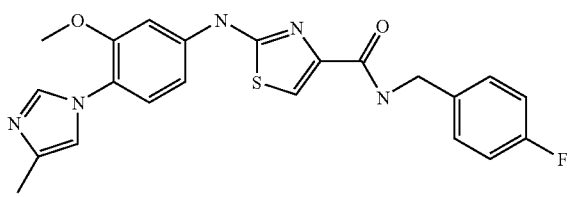

a) 2-[3-Methoxy-4-(4-methyl-imidazol-1-yl)-phenylamino]-thiazole-4-carboxylic acid A mixture of 2-[3-methoxy-4-(4-methyl-imidazol-1-yl)-phenylamino]-thiazole-4-carboxylic acid ethyl ester (210 mg, 0.586 mmol), KOH (3M in water, 1172 1, 3.52 mmol) and ethanol (3 ml) was heated to 90° C. for 12 h and then cooled to 0° C. An aqueous HCl solution (1 N) was added until pH7. The solvents were evaporated, toluene was added to the residue and evaporated again to yield the title compound as light brown solid (450 mg (purity 43%), 100%).
MS ISP (m/e): 331.1 (100) [(M+H)⁺].

b) 2-[3-Methoxy-4-(4-methyl-imidazol-1-yl)-phenylamino]-thiazole-4-carboxylic acid 4-fluoro-benzylamide To a suspension of 2-[3-methoxy-4-(4-methyl-imidazol-1-yl)-phenylamino]-thiazole-4-carboxylic acid (61.5 mg, purity 43%, 0.080 mmol) in dichloromethane (2 ml) were added 1-(3-dimethylaminopropyl)-3-ethylcarbodiimide hydrochloride (24.5 mg, 0.128 mmol), 1-hydroxybenzotriazole hydrate (19.6 mg, 0.128 mmol), triethylamine (30.0 mg, 0.296 mmol) and a solution of 4-fluorobenzyl amine (12 mg, 0.096 mmol) in dichloromethane (1 ml). After 12 h at rt again 1-(3-dimethylaminopropyl)-3-ethylcarbodiimide hydrochloride (24.5 mg, 0.128 mmol), 1-hydroxybenzotriazole hydrate (19.6 mg, 0.128 mmol), triethylamine (30.0 mg, 0.296 mmol) and a solution of 4-fluorobenzyl amine (12 mg, 0.096 mmol) in dichloromethane (1 ml) were added. After 12 h at rt the reaction mixture was directly purified by silica gel chromatography using dichloromethane/methanol as eluent. The title compound was obtained as a off-white foam (23.0 mg, 66%).
MS ISP (m/e): 438.2 (14) [(M+H)⁺].

¹H NMR (CDCl₃, 300 MHz): δ (ppm)=7.64-7.63 (m, 1H), 7.56 (s, 1H), 7.39-7.19 (m, 6H), 7.06-7.01 (m, 2H), 6.91-6.86 (m, 2H), 4.57 (d, 2H), 3.73 (s, 3H), 2.30 (m, 3H)

EXAMPLE 42

1-(3-Chloro-benzyl)-1H-[1,2,4]triazol-3-yl]-(4-pyridin-4-yl-phenyl)-amine

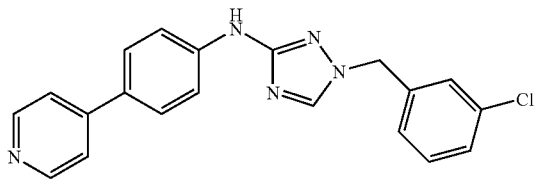

Prepared in analogy to example 1b) starting with 4-(4-bromo-phenyl)-pyridine (Journal of Medicinal Chemistry, 42, 3572-3587 (1999)) and 1-(3-chloro-benzyl)-1H-[1,2,4]triazol-3-ylamine from example 7a). The title compound was obtained as a slightly yellow solid (Yield=39%). MS ISP (m/e): 362.1 (100) [(M+H)⁺].

¹H NMR (DMSO, 300 MHz): δ (ppm)=9.53 (s, 1H), 8.55 (d, 2H), 8.47 (s, 1H), 7.72 (d, 2H), 7.65-7.60 (m, 4H), 7.45-7.35 (m, 3H), 7.29 (d, 1H), 5.36 (s, 2H).

EXAMPLE 43

[1-(4-Fluoro-benzyl)-1H-pyrazol-3-yl]-[3-methoxy-4-(4-methyl-imidazol-1-yl)-phenyl]-amine

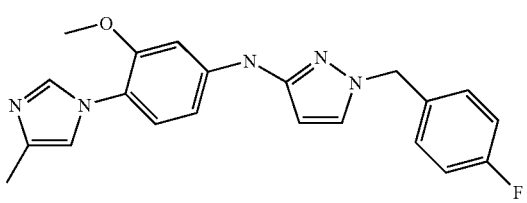

A mixture of 1-(4-bromo-2-methoxy-phenyl)-4-methyl-1H-imidazole (WO2009076352, Example 1; 50 mg, 0.19 mmol), 1-(4-fluoro-benzyl)-1H-pyrazol-3-ylamine (45 mg, 0.40 mmol), sodium phenoxide (35 mg, 0.57 mmol), tris(dibenzylideneacetone)dipalladium chloroform complex (3 mg, 0.003 mmol) and 4,5-bis(diphenylphosphino)-9,9-dimethylxanthene=Xanthphos (7 mg, 0.012 mmol) in dioxane (2 ml) was heated under an argon atmosphere in the microwave to 130° C. for 15 min. The mixture was diluted with water, extracted with dichloromethane and the product purified by chromatography on silica gel using dichloromethane/methanol as eluent. The title compound was obtained as a light yellow solid (Yield=42%). MS ISP (m/e): 378.4 (100) [(M+H)$^+$].

$^1$H NMR (CDCl$_3$, 300 MHz): δ (ppm)=7.57-7.56 (m, 1H), 7.31-7.30 (m, 1H), 7.27-7.21 (m, 2H), 7.09-6.98 (m, 4H), 6.82 (m, 1H), 6.68-6.64 (m, 1H), 6.09 (s, 1H), 5.99-5.98 (m, 1H), 5.17 (s, 2H), 3.75 (s, 3H), 2.29-2.28 (m, 3H).

EXAMPLE 44

(5-Benzyl-oxazol-2-yl)-[3-methoxy-4-(4-methyl-imidazol-1-yl)-phenyl]-amine

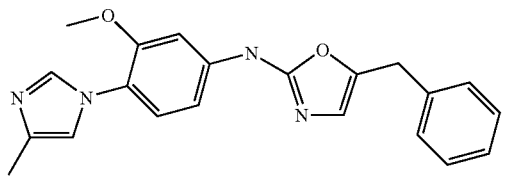

a) 2-Bromo-3-phenyl-propionaldehyde

To a solution of 3-phenylpropionaldehyde (13.4 g, purity 90%, 0.09 mol) in dichloromethane at 0° C. was slowly added bromine (13.7 g, 0.085 mol). After 12 h at rt the solvent was evaporated to yield crude title compound (26.0 g (purity about 60%), 81%).

$^1$H NMR (CDCl$_3$, 300 MHz): δ (ppm)=9.46 (s, 1H), 7.37-7.20 (m), 4.48-4.42 (m, 1H), 3.53-3.45 (m, 1H), 3.22-3.14 (m, 1H).

b) 5-Benzyl-oxazol-2-ylamine

To a solution of 2-bromo-3-phenyl-propionaldehyde (26.0 g, purity 60%, 0.0732 mol) in ethanol (300 ml) was added urea (14.66 g, 0.244 mol) and the reaction mixture was heated to 90° C. for 12 h. The solvent was evaporated, the residue was diluted with dichloromethane and washed with aqueous sodium hydroxide solution (2 N) and water. The organic phase was extracted three times with aqueous hydrochloric acid solution (2 N). The combined aqueous phases were adjusted to pH 10 with aqueous sodium hydroxide solution (2 N) and then extracted three times with dichloromethane. The combined organic phases were dried over sodium sulfate, the solvent was evaporated and the residue purified by silica gel chromatography using dichloromethane/methanol as eluent. The title compound was obtained as a yellow solid (1.78 g, 14%). MS ISP (m/e): 175.2 (100) [(M+H)$^+$].

$^1$H NMR (CDCl$_3$, 300 MHz): δ (ppm)=7.34-7.22 (m, 5H), 6.40 (s, 1H), 4.60 (bs, 2H), 3.85 (s, 2H).

c) (5-Benzyl-oxazol-2-yl)-[3-methoxy-4-(4-methyl-imidazol-1-yl)-phenyl]-amine

Prepared in analogy to example 43 starting with 1-(4-bromo-2-methoxy-phenyl)-4-methyl-1H-imidazole and 5-benzyl-oxazol-2-ylamine. The title compound was obtained as a yellow solid (Yield=22%). MS ISP (m/e): 361.3 (100) [(M+H)$^+$].

$^1$H NMR (CDCl$_3$, 300 MHz): δ (ppm)=7.60-7.59 (m, 1H), 7.42-7.41 (m, 1H), 7.36-7.24 (m, 5H), 7.15-7.12 (m, 1H), 7.05 (m, 1H), 6.88-6.84 (m, 2H), 6.62 (m, 1H), 3.94 (s, 2H), 3.80 (s, 3H), 2.29-2.28 (m, 3H).

EXAMPLE 45

[1-(4-Chloro-benzyl)-1H-pyrazol-3-yl]-[3-methoxy-4-(4-methyl-imidazol-1-yl)-phenyl]-amine

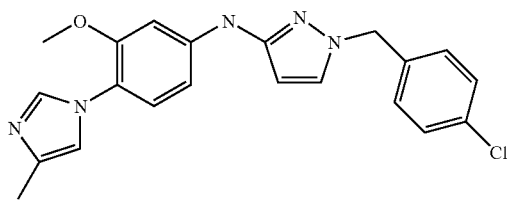

Prepared in analogy to example 43 starting with 1-(4-bromo-2-methoxy-phenyl)-4-methyl-1H-imidazole and 1-(4-chloro-benzyl)-1H-pyrazol-3-yl amine. The title compound was obtained as a yellow liquid (Yield=41%). MS ISP (m/e): 394.1 (100) [(M+H)$^+$].

$^1$H NMR (CDCl$_3$, 300 MHz): δ (ppm)=7.57-7.56 (m, 1H), 7.34-7.30 (m, 3H), 7.20-7.17 (m, 2H), 7.09-7.06 (m, 1H), 6.99-6.98 (m, 1H), 6.82 (m, 1H), 6.68-6.64 (m, 1H), 6.14 (s, 1H), 5.99-5.98 (m, 1H), 5.17 (s, 2H), 3.74 (s, 3H), 2.29-2.28 (m, 3H).

EXAMPLE 46

[1-(4-Fluoro-benzyl)-5-methyl-1H-pyrazol-3-yl]-[3-methoxy-4-(4-methyl-imidazol-1-yl)-phenyl]-amine

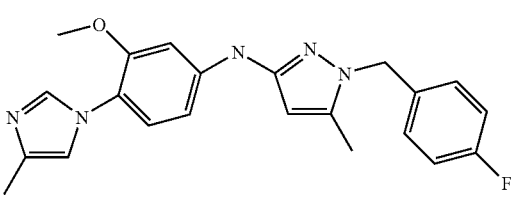

a) 1-(4-Fluoro-benzyl)-5-methyl-1H-pyrazol-3-ylamine

Prepared in analogy to example 10a) starting with 5-methyl-1H-pyrazol-3-ylamine and 4-fluorobenzyl bromide. The title compound was obtained as a white solid (Yield=14%). MS ISP (m/e): 206.1 (100) [(M+H)$^+$].

b) [1-(4-Fluoro-benzyl)-5-methyl-1H-pyrazol-3-yl]-[3-methoxy-4-4-methyl-imidazol-1-yl)-phenyl]-amine Prepared in analogy to example 43 starting with 1-(4-bromo-2-methoxy-phenyl)-4-methyl-1H-imidazole and 1-(4-fluoro-benzyl)-5-methyl-1H-pyrazol-3-ylamine. The title compound was obtained as a light yellow oil (Yield=41%). MS ISP (m/e): 392.2 (100) [(M+H)+].

$^1$H NMR (CDCl$_3$, 300 MHz): δ (ppm)=7.57-7.56 (m, 1H), 7.16-6.98 (m, 6H), 6.82 (m, 1H), 6.68-6.65 (m, 1H), 6.08 (s, 1H), 5.80 (s, 1H), 5.14 (s, 2H), 3.75 (s, 3H), 2.29-2.28 (m, 3H), 2.22 (s, 3H).

EXAMPLE 47

[1-(3-Chloro-benzyl)-1H-[1,2,4]triazol-3-yl]-[3-methoxy-4-(4-methyl-imidazol-1-yl)-phenyl]-amine

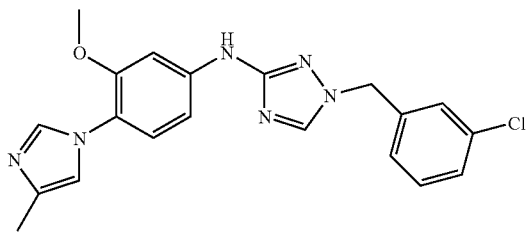

Prepared in analogy to example 1b) starting with 1-(4-bromo-2-methoxy-phenyl)-4-methyl-1H-imidazole (WO2009076352) and 1-(3-chloro-benzyl)-1H-[1,2,4]triazol-3-ylamine from example 7a). The title compound was obtained as a slightly yellow solid (Yield=13%). MS ISP (m/e): 395.2 (100) [(M+H)+].

$^1$H NMR (DMSO, 300 MHz): δ (ppm)=9.43 (s, 1H), 8.46 (s, 1H), 7.60 (s, 1H), 7.52 (d, 1H), 7.45 (s, 1H), 7.40-7.35 (m, 2H), 7.32 (d, 1H), 7.15 (d, 1H), 7.07 (dxd, 1H), 6.98 (s, 1H), 5.33 (s, 2H), 3.73 (s, 3H), 2.13 (s, 3H).

EXAMPLE 48

5-[3-Methoxy-4-(4-methyl-imidazol-1-yl)-phenylamino]-2-(3,4,5-trifluoro-benzyl)-2H-pyrazole-3-carboxylic acid methyl ester

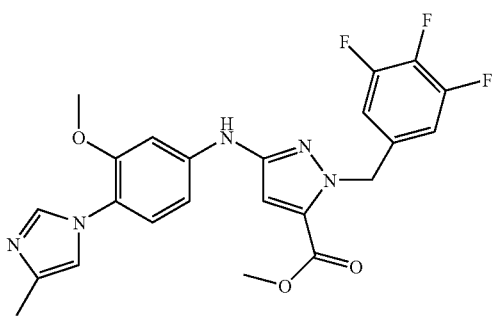

Prepared in analogy to example 1b) starting with 1-(4-bromo-2-methoxy-phenyl)-4-methyl-1H-imidazole (WO2009076352) and 5-amino-2-(3,4,5-trifluoro-benzyl)-2H-pyrazole-3-carboxylic acid methyl ester from example 39b). The title compound was obtained as a yellowish solid (Yield=34%). MS ISP (m/e): 472.1 (100) [(M+H)+].

$^1$H NMR (DMSO, 300 MHz): δ (ppm)=9.01 (s, 1H), 7.59 (s, 1H), 7.27 (d, 1H), 7.20-7.10 (m, 3H), 6.97 (s, 1H), 6.92 (dxd, 1H), 6.45 (s, 1H), 5.62 (s, 2H), 3.74 (s, 3H), 3.64 (s, 3H), 2.13 (s, 3H).

EXAMPLE 49

[1-(2,4-Dichloro-phenyl)-5-methyl-1H-[1,2,4]triazol-3-yl]-[3-methoxy-4-(4-methyl-imidazol-1-yl)-phenyl]-amine

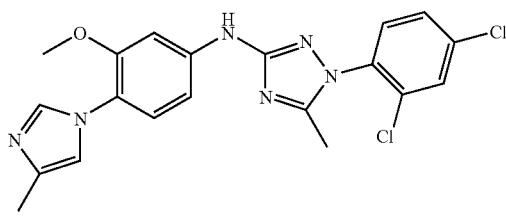

Prepared in analogy to example 1b) starting with 1-(4-bromo-2-methoxy-phenyl)-4-methyl-1H-imidazole (WO2009076352) and 1-(2,4-dichloro-phenyl)-5-methyl-1H-[1,2,4]triazol-3-ylamine (Synthesis 1976, 274). The title compound was obtained as a brownish solid (Yield=13%). MS ISP (m/e): 429.1 (100) [(M+H)+].

$^1$H NMR (DMSO, 300 MHz): δ (ppm)=9.48 (s, 1H), 7.97 (s, 1H), 7.76 (d, 1H), 7.67 (dxd, 1H), 7.60 (d, 1H), 7.39 (d, 1H), 7.23 (dxd, 1H), 7.20-7.15 (m, 2H), 6.98 (s, 1H), 3.73 (s, 3H), 2.24 (s, 3H), 2.13 (s, 3H).

EXAMPLE 50

[3-Methoxy-4-(4-methyl-imidazol-1-yl)-phenyl]-[1-(3,4,5-trifluoro-benzyl)-1H-[1,2,4]triazol-3-yl]-amine

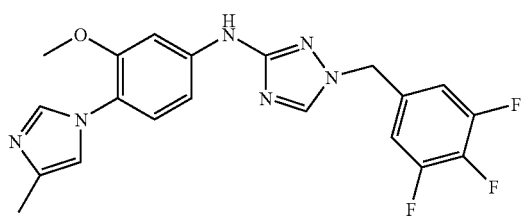

Prepared in analogy to example 1b) starting with 1-(4-bromo-2-methoxy-phenyl)-4-methyl-1H-imidazole (WO2009076352) and 1-(3,4,5-trifluoro-benzyl)-1H-[1,2,4] triazol-3-ylamine from example 17a). The title compound was obtained as a colorless foam (Yield=49%). MS ISP (m/e): 415.2 (100) [(M+H)+].

¹H NMR (DMSO, 300 MHz): δ (ppm)=9.45 (s, 1H), 8.41 (s, 1H), 7.59 (s, 1H), 7.50 (s, 1H), 7.37 (t broad, 2H), 7.15 (d, 1H), 7.08 (d, 1H), 6.98 (s, 1H), 6.74 (d, 1H), 5.31 (s, 2H), 3.74 (s, 3H), 2.13 (s, 3H).

EXAMPLE 51

2-[5-[3-Methoxy-4-(4-methyl-imidazol-1-yl)-phenylamino]-2-(3,4,5-trifluoro-benzyl)-2H-pyrazol-3-yl]-propan-2-ol

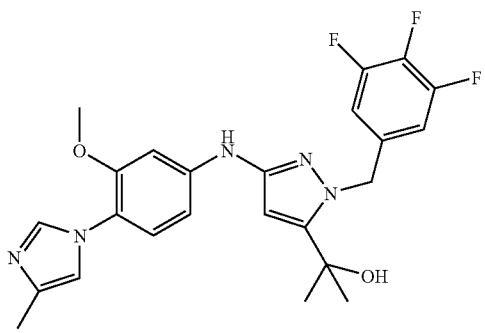

Prepared in analogy to example 35 from 5-[3-methoxy-4-(4-methyl-imidazol-1-yl)-phenylamino]-2-(3,4,5-trifluoro-benzyl)-2H-pyrazole-3-carboxylic acid methyl ester (example 48) and methyl magnesium chloride. The title compound was obtained as colorless solid (Yield=48%). MS ISP (m/e): 472.2 (100).

¹H NMR (DMSO, 300 MHz): δ (ppm)=8.71 (s, 1H), 7.56 (d, 1H), 7.31 (d, 1H), 7.14 (t broad, 2H), 7.08 (d, 1H), 6.94 (s, 1H), 6.82 (dxd, 1H), 5.70 (s, 1H), 5.50-5.45 (m, 2H), 3.66 (s, 3H), 2.12 (s, 3H), 1.50 (s, 6H).

EXAMPLE 52

[1-(4-Chloro-benzyl)-1H-[1,2,4]triazol-3-yl]-[3-methoxy-4-(4-methyl-imidazol-1-yl)-phenyl]-amine

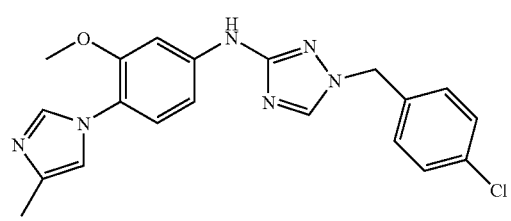

Prepared in analogy to example 1b) starting with 1-(4-bromo-2-methoxy-phenyl)-4-methyl-1H-imidazole (WO2009076352) and 1-(4-chloro-benzyl)-1H-[1,2,4]triazol-3-ylamine from example 3a). The title compound was obtained as a colorless solid (Yield=42%). MS ISP (m/e): 395.1 (100) [(M+H)⁺].

¹H NMR (DMSO, 300 MHz): δ (ppm)=9.41 (s, 1H), 8.43 (s, 1H), 7.59 (d, 1H), 7.48 (d, 1H), 7.45 (d, 2H), 7.38 (d, 2H), 7.14 (d, 1H), 7.08 (dxd, 1H), 6.97 (s, 1H), 5.31 (s, 2H), 3.72 (s, 3H), 2.13 (s, 3H).

EXAMPLE 53

[3-Methoxy-4-(4-methyl-imidazol-1-yl)-phenyl]-[1-(4-methyl-benzyl)-1H-[1,2,4]triazol-3-yl]-amine

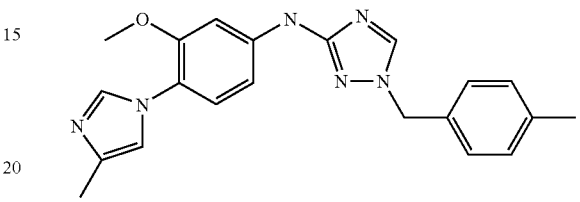

Prepared in analogy to example 43 starting with 1-(4-bromo-2-methoxy-phenyl)-4-methyl-1H-imidazole and 1-(4-methyl-benzyl)-1H-[1,2,4]triazol-3-ylamine. The title compound was obtained as a light yellow solid (Yield=60%). MS ISP (m/e): 375.4 (100) [(M+H)⁺].

¹H NMR (CDCl₃, 300 MHz): δ (ppm)=7.77 (m, 1H), 7.59 (m, 1H), 7.43-7.42 (m, 1H), 7.25-7.17 (m, 4H), 7.14-7.11 (m, 1H), 6.91-6.87 (m, 1H), 6.84 (m, 1H), 6.76 (m, 1H), 5.19 (s, 2H), 3.81 (s, 3H), 2.36 (s, 3H), 2.29 (s, 3H).

EXAMPLE 54

[3-Methoxy-4-(4-methyl-imidazol-1-yl)-phenyl]-[1-(3-trifluoromethyl-benzyl)-1H-[1,2,4]triazol-3-yl]-amine

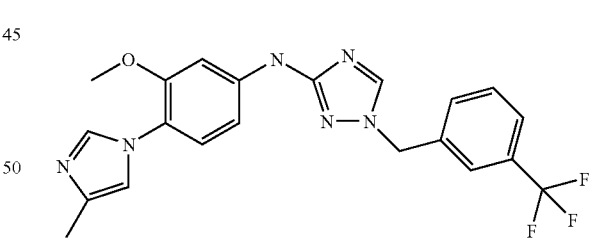

Prepared in analogy to example 43 starting with 1-(4-bromo-2-methoxy-phenyl)-4-methyl-1H-imidazole and 1-(3-trifluoromethyl-benzyl)-1H-[1,2,4]triazol-3-ylamine. The title compound was obtained as a light yellow solid (Yield=63%). MS ISP (m/e): 429.3 (100) [(M+H)⁺].

¹H NMR (CDCl₃, 300 MHz): δ (ppm)=7.89 (m, 1H), 7.65-7.59 (m, 3H), 7.53-7.51 (m, 2H), 7.40-7.39 (m, 1H), 7.14-7.12 (m, 1H), 6.91-6.87 (m, 1H), 6.84 (m, 1H), 6.70 (m, 1H), 5.30 (s, 2H), 3.79 (s, 3H), 2.30-2.29 (m, 3H).

EXAMPLE 55

[3-Methoxy-4-(4-methyl-imidazol-1-yl)-phenyl]-[1-(1-phenyl-ethyl)-1H-[1,2,4]triazol-3-yl]-amine

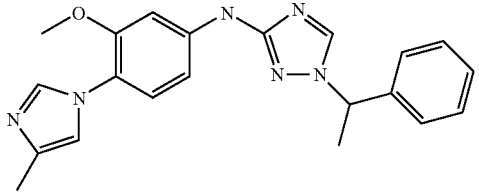

Prepared in analogy to example 43 starting with 1-(4-bromo-2-methoxy-phenyl)-4-methyl-1H-imidazole and 1-(1-phenyl-ethyl)-1H-[1,2,4]triazol-3-ylamine. The title compound was obtained as a white solid (Yield=66%). MS ISP (m/e): 375.3 (100) [(M+H)$^+$].
$^1$H NMR (CDCl$_3$, 300 MHz): δ (ppm)=7.79 (m, 1H), 7.59-7.58 (m, 1H), 7.50-7.49 (m, 1H), 7.42-7.31 (m, 5H), 7.13-7.10 (m, 1H), 6.87-6.83 (m, 2H), 6.76 (m, 1H), 5.43 (q, 1H), 3.79 (s, 3H), 2.29 (s, 3H), 1.94 (d, 3H).

The invention claimed is:
1. A method of treating a disorder selected from the group consisting of Alzheimer's disease, cerebral amyloid angiopathy, hereditary cerebral hemorrhage with amyloidosis, Dutch-type (HCHWA-D), multi-infarct dementia, dementia pugilistica and Down syndrome, comprising administering a therapeutically effective amount of a compound of formula I

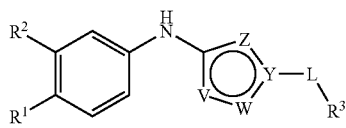

wherein
R$^1$ is a five or six membered heteroaryl group, optionally substituted by one or two R';
R' is lower alkyl;
R$^2$ is hydrogen, lower alkyl, lower alkoxy, hydroxy, halogen or cyano;
Z is N, C, O or S;
V is N, C(R"), O or S;
W is N, C(R"), O, or S;
Y is N or C;
with the proviso that only one of Z, V or W is O or S;
R" is hydrogen, lower alkyl, lower alkyl substituted by halogen or hydroxy, or C(O)O—R$^4$;
L is a bond, —(CR$^4$$_2$)$_n$—, —C(O)NR$^4$—, —C(O)NR$^4$CH$_2$—, or —C(O)—;
each R$^4$ is the same or different and is hydrogen or lower alkyl;
R$^3$ is lower alkyl, lower alkoxy, lower alkyl substituted by hydroxy, cycloalkyl, or phenyl optionally substituted by one or more R'";
R'" is halogen, cyano, lower alkyl, lower alkyl substituted by halogen or hydroxy, lower alkoxy or C(O)O—R$^4$; and
n is 1, 2 or 3;
or a pharmaceutically active acid addition salt thereof.

2. The method of claim 1

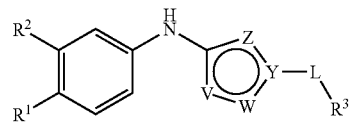

wherein
R$^1$ is a five or six membered heteroaryl group, optionally substituted by one or two R' selected from

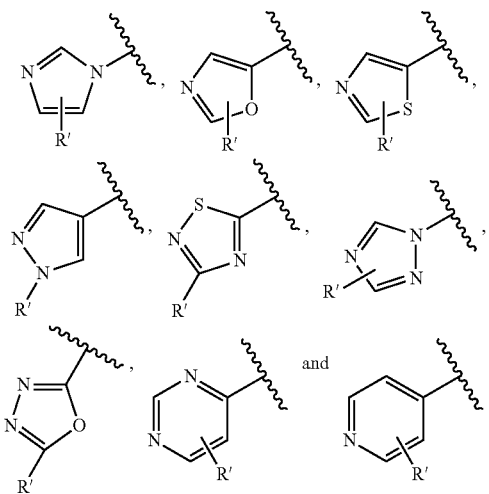

R' is lower alkyl;
R$^2$ is hydrogen, lower alkyl, lower alkoxy, hydroxy, halogen or cyano;

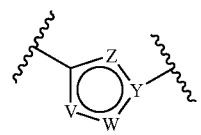

is a five membered heteroaryl group selected from

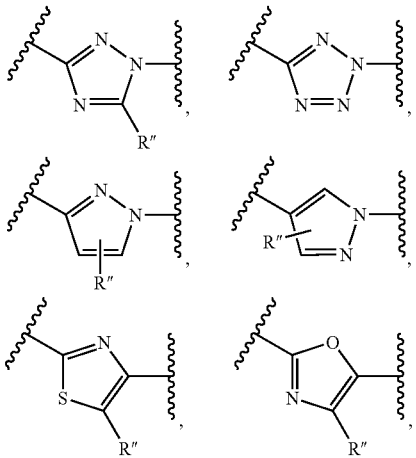

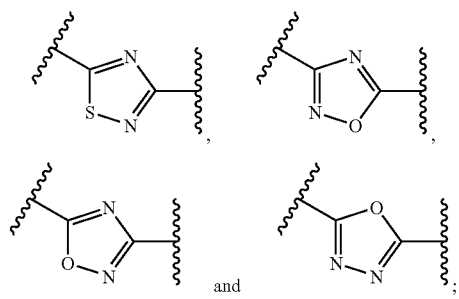

R'' is hydrogen, lower alkyl, lower alkyl substituted by halogen or hydroxy, or C(O)O—R⁴;

L is a bond, —(CR⁴₂)ₙ—, —C(O)NR⁴—, —C(O)NR⁴CH₂—, or —C(O)—;

each R⁴ is the same or different and is hydrogen or lower alkyl;

R³ is lower alkyl, lower alkoxy, lower alkyl substituted by hydroxy, cycloalkyl, or phenyl optionally substituted by one or more R'''

R''' is halogen, cyano, lower alkyl, lower alkyl substituted by halogen or hydroxy, lower alkoxy or C(O)O—R⁴; and n is 1, 2 or 3;

or a pharmaceutically active acid addition salt thereof.

3. The method of claim 2,

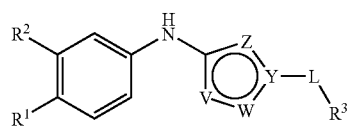

wherein
R¹ is

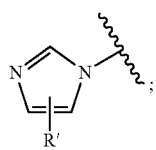

R' is lower alkyl;

R² is hydrogen, lower alkyl, lower alkoxy, hydroxy, halogen or cyano;

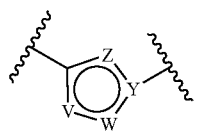

is a five membered heteroaryl group selected from

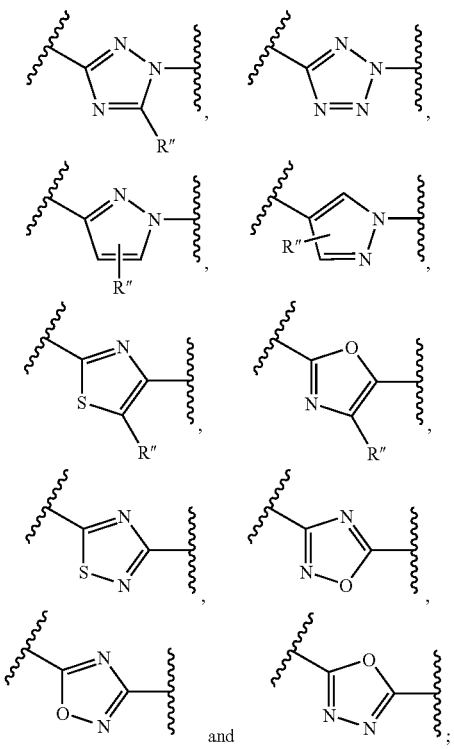

R'' is hydrogen, lower alkyl, lower alkyl substituted by halogen or hydroxy, or C(O)O—R⁴;

L is a bond, —(CR⁴₂)ₙ—, —C(O)NR⁴—, —C(O)NR⁴CH₂—, or —C(O)—;

each R⁴ is the same or different and is hydrogen or lower alkyl;

R³ is lower alkyl, lower alkoxy, lower alkyl substituted by hydroxy, cycloalkyl, or phenyl optionally substituted by one or more R''';

R''' is halogen, cyano, lower alkyl, lower alkyl substituted by halogen or hydroxy, lower alkoxy or C(O)O—R⁴; and n is 1, 2 or 3;

or a pharmaceutically active acid addition salt thereof.

4. The method of claim 1, wherein the compound administered is selected from the group consisting of 5-[1-(4-chloro-benzyl)-1H-[1,2,4]triazol-3-ylamino]-2-(4-methyl-imidazol-1-yl)-benzonitrile;

5-[1-(3-chloro-benzyl)-1H-[1,2,4]triazol-3-ylamino]-2-(4-methyl-imidazol-1-yl)-benzonitrile;

5-[1-(2-chloro-benzyl)-1H-[1,2,4]triazol-3-ylamino]-2-(4-methyl-imidazol-1-yl)-benzonitrile;

5-[1-(4-cyano-benzyl)-1H-[1,2,4]triazol-3-ylamino]-2-(4-methyl-imidazol-1-yl)-benzonitrile;

5-(5-benzyl-[1,2,4]oxadiazol-3-ylamino)-2-(4-methyl-imidazol-1-yl)-benzonitrile;

5-(1-benzyl-1H-pyrazol-3-ylamino)-2-(4-methyl-imidazol-1-yl)-benzonitrile;

2-(4-methyl-imidazol-1-yl)-5-[1-(1-phenyl-ethyl)-1H-[1,2,4]triazol-3-ylamino]-benzonitrile;

5-[1-(4-fluoro-benzyl)-1H-pyrazol-3-ylamino]-2-(4-methyl-imidazol-1-yl)-benzonitrile;

2-(4-methyl-imidazol-1-yl)-5-[1-(3,4,5-trifluoro-benzyl)-1H-[1,2,4]triazol-3-ylamino]-benzonitrile; and 5-[5-(2,6-dichloro-benzyl)-[1,2,4]oxadiazol-3-ylamino]-2-(4-methyl-imidazol-1-yl)-benzonitrile.

5. The method of claim 1, wherein the compound administered is selected from the group consisting of 5-(1-benzyl-1H-[1,2,4]triazol-3-ylamino)-2-(4-methyl-imidazol-1-yl)-benzonitrile;

5-[1-(2,4-dichloro-benzyl)-1H-[1,2,4]triazol-3-ylamino]-2-(4-methyl-imidazol-1-yl)-benzonitrile;

2-(4-methyl-imidazol-1-yl)-5-[1-(3-trifluoromethyl-benzyl)-1H-[1,2,4]triazol-3-ylamino]-benzonitrile;

5-[1-(4-methyl-benzyl)-1H-[1,2,4]triazol-3-ylamino]-2-(4-methyl-imidazol-1-yl)-benzonitrile;

2-(4-methyl-imidazol-1-yl)-5-[1-(3,4,5-trifluoro-benzyl)-1H-pyrazol-3-ylamino]-benzonitrile;

5-(3-benzyl-[1,2,4]thiadiazol-5-ylamino)-2-(4-methyl-imidazol-1-yl)-benzonitrile;

5-[1-(3-chloro-benzyl)-1H-pyrazol-3-ylamino]-2-(4-methyl-imidazol-1-yl)-benzonitrile;

5-[1-(2,4-dichloro-benzyl)-1H-pyrazol-3-ylamino]-2-(4-methyl-imidazol-1-yl)-benzonitrile;

5-[1-(4-chloro-benzyl)-1H-pyrazol-3-ylamino]-2-(4-methyl-imidazol-1-yl)-benzonitrile; and 5-[3-cyano-4-(4-methyl-imidazol-1-yl)-phenylamino]-2-(3,4,5-trifluoro-benzyl)-2H-pyrazole-3-carboxylic acid methyl ester.

6. The method of claim 1, wherein the compound administered is selected from the group consisting of 5-[5-(1-hydroxy-1-methyl-ethyl)-1-(3,4,5-trifluoro-benzyl)-1H-pyrazol-3-ylamino]-2-(4-methyl-imidazol-1-yl)-benzonitrile;

1-(3-chloro-benzyl)-1H-[1,2,4]triazol-3-yl]-(4-pyridin-4-yl-phenyl)-amine;

[1-(4-fluoro-benzyl)-1H-pyrazol-3-yl]-[3-methoxy-4-(4-methyl-imidazol-1-yl)-phenyl]-amine;

[1-(4-chloro-benzyl)-1H-pyrazol-3-yl]-[3-methoxy-4-(4-methyl-imidazol-1-yl)-phenyl]-amine;

[1-(4-fluoro-benzyl)-5-methyl-1H-pyrazol-3-yl]-[3-methoxy-4-(4-methyl-imidazol-1-yl)-phenyl]-amine;

[1-(3-chloro-benzyl)-1H-[1,2,4]triazol-3-yl]-[3-methoxy-4-(4-methyl-imidazol-1-yl)-phenyl]-amine;

5-[3-methoxy-4-(4-methyl-imidazol-1-yl)-phenylamino]-2-(3,4,5-trifluoro-benzyl)-2H-pyrazole-3-carboxylic acid methyl ester;

[3-methoxy-4-(4-methyl-imidazol-1-yl)-phenyl]-[1-(3,4,5-trifluoro-benzyl)-1H-[1,2,4]triazol-3-yl]-amine;

2-[5-[3-methoxy-4-(4-methyl-imidazol-1-yl)-phenylamino]-2-(3,4,5-trifluoro-benzyl)-2H-pyrazol-3-yl]-propan-2-ol; and

[1-(4-chloro-benzyl)-1H-[1,2,4]triazol-3-yl]-[3-methoxy-4-(4-methyl-imidazol-1-yl)-phenyl]-amine.

7. The method of claim 3, wherein the compound administered is selected from the group consisting of

[3-methoxy-4-(4-methyl-imidazol-1-yl)-phenyl]-[1-(4-methyl-benzyl)-1H-[1,2,4]triazol-3-yl]-amine;

[3-methoxy-4-(4-methyl-imidazol-1-yl)-phenyl]-[1-(3-trifluoromethyl-benzyl)-1H-[1,2,4]triazol-3-yl]-amine;

[3-methoxy-4-(4-methyl-imidazol-1-yl)-phenyl]-[1-(1-phenyl-ethyl)-1H-[1,2,4]triazol-3-yl]-amine;

5-[1-(2,4-dichloro-phenyl)-5-methyl-1H-[1,2,4]triazol-3-ylamino]-2-(4-methyl-imidazol-1-yl)-benzonitrile;

2-(4-methyl-imidazol-1-yl)-5-(1-phenyl-1H-[1,2,4]triazol-3-ylamino)-benzonitrile;

2-(4-methyl-imidazol-1-yl)-5-[1-(2-trifluoromethyl-phenyl)-1H-[1,2,4]triazol-3-ylamino]-benzonitrile;

5-[1-(4-chloro-phenyl)-1H-[1,2,4]triazol-3-ylamino]-2-(4-methyl-imidazol-1-yl)-benzonitrile;

5-[1-(2-chloro-phenyl)-1H-[1,2,4]triazol-3-ylamino]-2-(4-methyl-imidazol-1-yl)-benzonitrile; and

[1-(2,4-dichloro-phenyl)-5-methyl-1H-[1,2,4]triazol-3-yl]-[3-methoxy-4-(4-methyl-imidazol-1-yl)-phenyl]-amine.

8. A compound of formula I-A

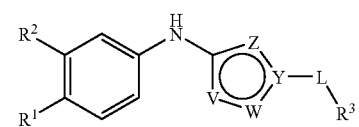

I-A wherein $R^1$ is a five or six membered heteroaryl group, optionally substituted by one or two R', selected from

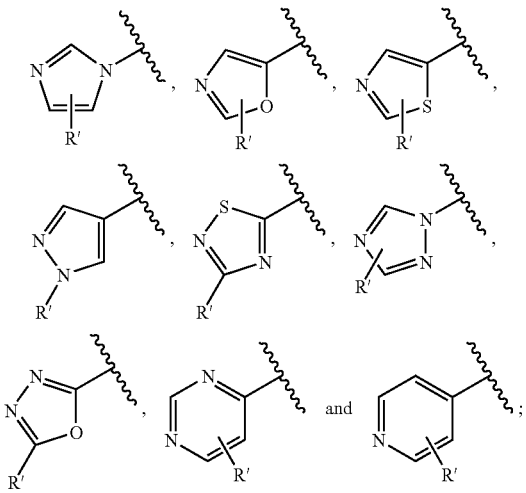

R' is lower alkyl;

$R^2$ is hydrogen, lower alkyl, lower alkoxy, hydroxy, halogen or cyano;

Z is N, C, O or S;

V is N, C(R"), O or S;

W is N, C(R"), O, or S;

Y is N or C;

with the proviso that only one of Z, V or W is O or S;

R" is hydrogen, lower alkyl, lower alkyl substituted by halogen or hydroxy, or C(O)O—$R^4$;

L is —$(CR^4_2)_n$—, —C(O)NR$^4$— or —C(O)NR$^4$CH$_2$—;

each $R^4$ is the same or different and is hydrogen or lower alkyl;

$R^3$ is lower alkyl, cycloalkyl, or phenyl optionally substituted by one or more R'";

R'" is halogen, cyano, lower alkyl, lower alkyl substituted by halogen or hydroxy, lower alkoxy or C(O)O—$R^4$; and n is 1, 2 or 3;

or a pharmaceutically active acid addition salt thereof.

9. The compound of claim 8 having formula I-A1

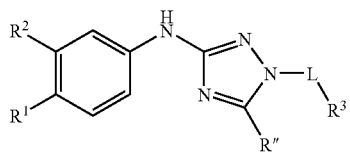

I-A1 wherein
R¹ is

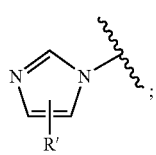

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴;
and
n is 1, 2 or 3;
or a pharmaceutically active acid addition salt thereof.

10. The compound of claim 8 having formula I-A11

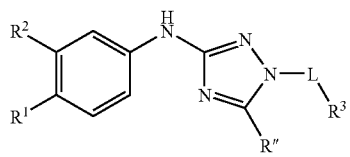

I-A11 wherein
R¹ is

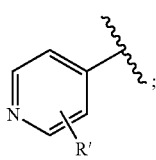

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;
L is —(CR⁴$_2$)$_n$—, —C(O)NR⁴— or —C(O)NR⁴CH$_2$—;
each R⁴ is the same or different and is hydrogen or lower alkyl;

R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

11. The compound of claim 8 having formula I-A2

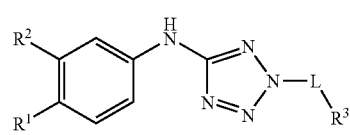

I-A2 wherein
R¹ is

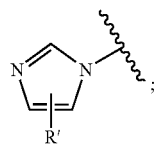

R' is lower alkyl;
R² is hydrogen, lower alkyl, lower alkoxy, hydroxy, halogen or cyano;
L is —(CR⁴$_2$)$_n$—, —C(O)NR⁴— or —C(O)NR⁴CH$_2$—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

12. The compound of claim 8 having formula I-A3

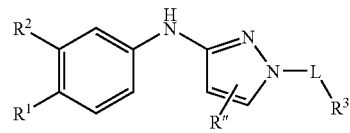

I-A3 wherein
R¹ is

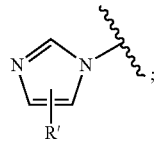

R' is lower alkyl;
R² is hydrogen, lower alkyl, lower alkoxy, hydroxy, halogen or cyano;
R" is hydrogen, lower alkyl, lower alkyl substituted by halogen or hydroxy, or C(O)O—R⁴;

L is —(CR$^4_2$)$_n$—, —C(O)NR$^4$— or —C(O)NR$^4$CH$_2$—;

each R$^4$ is the same or different and is hydrogen or lower alkyl;

R$^3$ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R$^4$; and n is 1, 2 or 3;

or a pharmaceutically active acid addition salt thereof.

13. The compound of claim 8 having formula I-A4

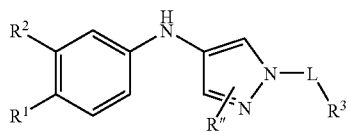

I-A4 wherein
R$^1$ is

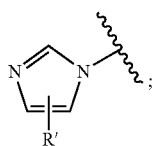

R' is lower alkyl;

R$^2$ is hydrogen, lower alkyl, lower alkoxy, hydroxy, halogen or cyano;

R" is hydrogen, lower alkyl, lower alkyl substituted by halogen or hydroxy, or C(O)O—R$^4$;

L is —(CR$^4_2$)$_n$—, —C(O)NR$^4$— or —C(O)NR$^4$CH$_2$—;

each R$^4$ is the same or different and is hydrogen or lower alkyl;

R$^3$ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R$^4$; and n is 1, 2 or 3;

or a pharmaceutically active acid addition salt thereof.

14. The compound of claim 8 having formula I-A5

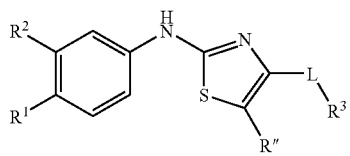

I-A5 wherein
R$^1$ is

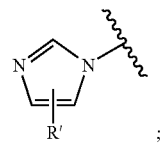

R' is lower alkyl;

R$^2$ is hydrogen, lower alkyl, lower alkoxy, hydroxy, halogen or cyano;

R" is hydrogen, lower alkyl, lower alkyl substituted by halogen or hydroxy, or C(O)O—R$^4$;

L is —(CR$^4_2$)$_n$—, —C(O)NR$^4$— or —C(O)NR$^4$CH$_2$—;

each R$^4$ is the same or different and is hydrogen or lower alkyl;

R$^3$ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R$^4$; and n is 1, 2 or 3;

or a pharmaceutically active acid addition salt thereof.

15. The compound of claim 8 having formula I-A6

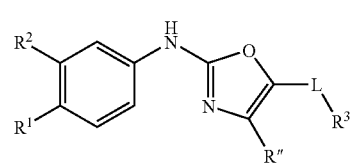

I-A6 wherein
R$^1$ is

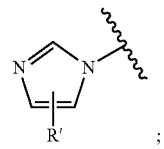

R' is lower alkyl;

R$^2$ is hydrogen, lower alkyl, lower alkoxy, hydroxy, halogen or cyano;

R" is hydrogen, lower alkyl, lower alkyl substituted by halogen or hydroxy, or C(O)O—R$^4$;

L is —(CR$^4_2$)$_n$—, —C(O)NR$^4$— or —C(O)NR$^4$CH$_2$—;

each R$^4$ is the same or different and is hydrogen or lower alkyl;

R$^3$ is lower alkyl, cycloalkyl, or phenyl optionally substituted by one or more R'";

R'" is halogen, cyano, lower alkyl, lower alkyl substituted by halogen or hydroxy, lower alkoxy or C(O)O—R$^4$; and n is 1, 2 or 3;

or a pharmaceutically active acid addition salt thereof.

16. The compound of claim 8 having formula I-A7

I-A7

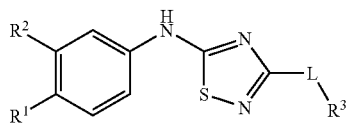

wherein
R¹ is

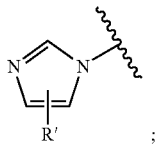

;

R' is lower alkyl;
R² is hydrogen, lower alkyl, lower alkoxy, hydroxy, halogen or cyano;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

17. A compound of claim 8 having formula I-A8

I-A8

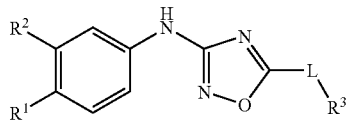

wherein
R¹ is

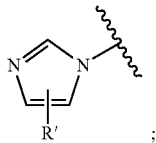

;

R' is lower alkyl;
R² is hydrogen, lower alkyl, lower alkoxy, hydroxy, halogen or cyano;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

18. The compound of claim 8 having formula I-A9

I-A9

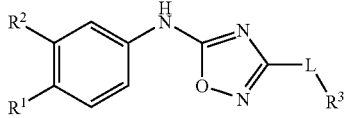

wherein
R¹ is

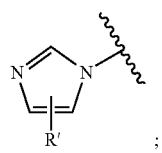

;

R' is lower alkyl;
R² is hydrogen, lower alkyl, lower alkoxy, hydroxy, halogen or cyano;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

19. The compound of claim 8 having formula I-A10

I-A10

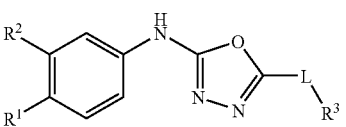

wherein
R¹ is

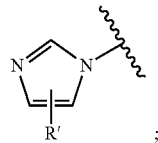

;

R' is lower alkyl;
R² is hydrogen, lower alkyl, lower alkoxy, hydroxy, halogen or cyano;
L is —(CR⁴₂)ₙ—, —C(O)NR⁴— or —C(O)NR⁴CH₂—;
each R⁴ is the same or different and is hydrogen or lower alkyl;
R³ is lower alkyl, cycloalkyl, or phenyl optionally substituted by one or more R'";
R'" is halogen, cyano, lower alkyl, lower alkyl substituted by halogen or hydroxy, lower alkoxy or C(O)O—R⁴; and
n is 1, 2 or 3;
or a pharmaceutically active acid addition salt thereof.

20. A compound of claim 5, wherein $R^1$ is

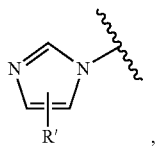

R' is methyl, L is —C(R$^4$)$_2$— and R$^3$ is phenyl optionally substituted by R'''.

21. A compound of claim 8, selected from the group consisting of

5-[1-(4-chloro-benzyl)-1H-[1,2,4]triazol-3-ylamino]-2-(4-methyl-imidazol-1-yl)-benzonitrile;
5-[1-(3-chloro-benzyl)-1H-[1,2,4]triazol-3-ylamino]-2-(4-methyl-imidazol-1-yl)-benzonitrile;
5-[1-(2-chloro-benzyl)-1H-[1,2,4]triazol-3-ylamino]-2-(4-methyl-imidazol-1-yl)-benzonitrile;
5-[1-(4-cyano-benzyl)-1H-[1,2,4]triazol-3-ylamino]-2-(4-methyl-imidazol-1-yl)-benzonitrile;
5-(5-benzyl-[1,2,4]oxadiazol-3-ylamino)-2-(4-methyl-imidazol-1-yl)-benzonitrile;
5-(1-benzyl-1H-pyrazol-3-ylamino)-2-(4-methyl-imidazol-1-yl)-benzonitrile;
2-(4-methyl-imidazol-1-yl)-5-[1-(1-phenyl-ethyl)-1H-[1,2,4]triazol-3-ylamino]-benzonitrile;
5-[1-(4-fluoro-benzyl)-1H-pyrazol-3-ylamino]-2-(4-methyl-imidazol-1-yl)-benzonitrile;
2-(4-methyl-imidazol-1-yl)-5-[1-(3,4,5-trifluoro-benzyl)-1H-[1,2,4]triazol-3-ylamino]-benzonitrile;
5-[5-(2,6-dichloro-benzyl)-[1,2,4]oxadiazol-3-ylamino]-2-(4-methyl-imidazol-1-yl)-benzonitrile; and
5-(1-benzyl-1H-[1,2,4]triazol-3-ylamino)-2-(4-methyl-imidazol-1-yl)-benzonitrile.

22. A compound of claim 8, selected from the group consisting of

5-[1-(2,4-dichloro-benzyl)-1H-[1,2,4]triazol-3-ylamino]-2-(4-methyl-imidazol-1-yl)-benzonitrile;
2-(4-methyl-imidazol-1-yl)-5-[1-(3-trifluoromethyl-benzyl)-1H-[1,2,4]triazol-3-ylamino]-benzonitrile;
5-[1-(4-methyl-benzyl)-1H-[1,2,4]triazol-3-ylamino]-2-(4-methyl-imidazol-1-yl)-benzonitrile;
2-(4-methyl-imidazol-1-yl)-5-[1-(3,4,5-trifluoro-benzyl)-1H-pyrazol-3-ylamino]-benzonitrile;
5-(3-benzyl-[1,2,4]thiadiazol-5-ylamino)-2-(4-methyl-imidazol-1-yl)-benzonitrile;
5-[1-(3-chloro-benzyl)-1H-pyrazol-3-ylamino]-2-(4-methyl-imidazol-1-yl)-benzonitrile;
5-[1-(2,4-dichloro-benzyl)-1H-pyrazol-3-ylamino]-2-(4-methyl-imidazol-1-yl)-benzonitrile;
5-[1-(4-chloro-benzyl)-1H-pyrazol-3-ylamino]-2-(4-methyl-imidazol-1-yl)-benzonitrile;
5-[3-cyano-4-(4-methyl-imidazol-1-yl)-phenylamino]-2-(3,4,5-trifluoro-benzyl)-2H-pyrazole-3-carboxylic acid methyl ester;
5-[5-(1-hydroxy-1-methyl-ethyl)-1-(3,4,5-trifluoro-benzyl)-1H-pyrazol-3-ylamino]-2-(4-methyl-imidazol-1-yl)-benzonitrile; and
1-(3-chloro-benzyl)-1H-[1,2,4]triazol-3-yl]-(4-pyridin-4-yl-phenyl)-amine.

23. A compound of claim 8, selected from the group consisting of

[1-(4-fluoro-benzyl)-1H-pyrazol-3-yl]-[3-methoxy-4-(4-methyl-imidazol-1-yl)-phenyl]-amine;
[1-(4-chloro-benzyl)-1H-pyrazol-3-yl]-[3-methoxy-4-(4-methyl-imidazol-1-yl)-phenyl]-amine;
[1-(4-fluoro-benzyl)-5-methyl-1H-pyrazol-3-yl]-[3-methoxy-4-(4-methyl-imidazol-1-yl)-phenyl]-amine;
[1-(3-chloro-benzyl)-1H-[1,2,4]triazol-3-yl]-[3-methoxy-4-(4-methyl-imidazol-1-yl)-phenyl]-amine;
5-[3-methoxy-4-(4-methyl-imidazol-1-yl)-phenylamino]-2-(3,4,5-trifluoro-benzyl)-2H-pyrazole-3-carboxylic acid methyl ester;
[3-methoxy-4-(4-methyl-imidazol-1-yl)-phenyl]-[1-(3,4,5-trifluoro-benzyl)-1H-[1,2,4]triazol-3-yl]-amine;
2-[5-[3-methoxy-4-(4-methyl-imidazol-1-yl)-phenylamino]-2-(3,4,5-trifluoro-benzyl)-2H-pyrazol-3-yl]-propan-2-ol;
[1-(4-chloro-benzyl)-1H-[1,2,4]triazol-3-yl]-[3-methoxy-4-(4-methyl-imidazol-1-yl)-phenyl]-amine;
[3-methoxy-4-(4-methyl-imidazol-1-yl)-phenyl]-[1-(4-methyl-benzyl)-1H-[1,2,4]triazol-3-yl]-amine;
[3-methoxy-4-(4-methyl-imidazol-1-yl)-phenyl]-[1-(3-trifluoromethyl-benzyl)-1H-[1,2,4]triazol-3-yl]-amine and
[3-methoxy-4-(4-methyl-imidazol-1-yl)-phenyl]-[1-(1-phenyl-ethyl)-1H-[1,2,4]triazol-3-yl]-amine.

24. A pharmaceutical composition comprising a therapeutically effective amount of a compound of formula I-A

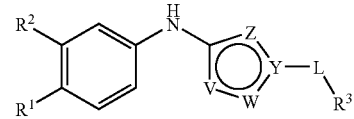

wherein $R^1$ is a five or six membered heteroaryl group, optionally substituted by one or two R', selected from

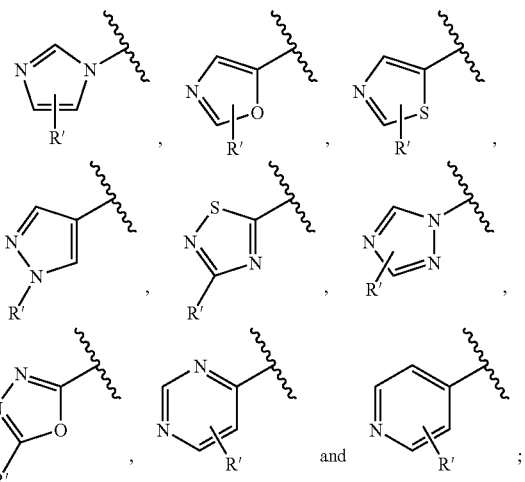

R' is lower alkyl;
$R^2$ is hydrogen, lower alkyl, lower alkoxy, hydroxy, halogen or cyano;
Z is N, C, O or S;
V is N, C(R''), O or S;
W is N, C(R''), O, or S;
Y is N or C;
with the proviso that only one of Z, V or W is O or S;

R'' is hydrogen, lower alkyl, lower alkyl substituted by halogen or hydroxy, or C(O)O—$R^4$;

L is —$(CR^4_2)_n$—, —C(O)$NR^4$— or —C(O)$NR^4CH_2$—;

each $R^4$ is the same or different and is hydrogen or lower alkyl;

$R^3$ is lower alkyl, cycloalkyl, or phenyl optionally substituted by one or more R''';

R''' is halogen, cyano, lower alkyl, lower alkyl substituted by halogen or hydroxy, lower alkoxy or C(O)O—$R^4$; and n is 1, 2 or 3;

or a pharmaceutically active acid addition salt thereof and a pharmaceutically acceptable carrier.

\* \* \* \* \*